United States Patent
Al-Ali et al.

(10) Patent No.: US 12,070,293 B2
(45) Date of Patent: *Aug. 27, 2024

(54) WEARABLE PULSE OXIMETER AND RESPIRATION MONITOR

(71) Applicant: Masimo Corporation, Irvine, CA (US)

(72) Inventors: Ammar Al-Ali, San Juan Capistrano, CA (US); Chad A. DeJong, Los Angeles, CA (US)

(73) Assignee: Masimo Corporation, Irvine, CA (US)

( * ) Notice: Subject to any disclaimer, the term of this patent is extended or adjusted under 35 U.S.C. 154(b) by 19 days.

This patent is subject to a terminal disclaimer.

(21) Appl. No.: 17/525,140

(22) Filed: Nov. 12, 2021

(65) Prior Publication Data

US 2022/0175249 A1    Jun. 9, 2022

Related U.S. Application Data

(63) Continuation of application No. 16/813,551, filed on Mar. 9, 2020, now Pat. No. 11,202,571, which is a
(Continued)

(51) Int. Cl.
*A61B 5/00* (2006.01)
*A61B 5/1455* (2006.01)

(52) U.S. Cl.
CPC .......... *A61B 5/0059* (2013.01); *A61B 5/0015* (2013.01); *A61B 5/14552* (2013.01);
(Continued)

(58) Field of Classification Search
CPC . A61B 5/0059; A61B 5/0015; A61B 5/14552; A61B 5/6824; A61B 5/6828;
(Continued)

(56) References Cited

U.S. PATENT DOCUMENTS

| 3,646,606 A | 2/1972 | Buxton et al. |
| 3,690,313 A | 9/1972 | Weber et al. |

(Continued)

FOREIGN PATENT DOCUMENTS

| CN | 301342850 | 9/2010 |
| CN | 302423595 | 5/2013 |

(Continued)

OTHER PUBLICATIONS

US 8,845,543 B2, 09/2014, Diab et al. (withdrawn)
(Continued)

*Primary Examiner* — Eric F Winakur
*Assistant Examiner* — Abid A Mustansir
(74) *Attorney, Agent, or Firm* — Knobbe, Martens, Olson & Bear, LLP

(57) ABSTRACT

A wireless patient monitoring device can be fully functional stand-alone patient monitoring device capable of various physiological measurements. The patient monitoring device is small and light enough to be comfortably worn on the patient, such as on the patient's wrist or around the neck. The patient monitoring device can have a monitor instrument removably engaging a disposable base. The base can have outlets for connecting to an acoustic respiration sensor and an oximeter sensor. The patient monitoring device can have pogo pin connectors connecting the monitor instrument and the disposable base so that the monitor instrument can receive sensor data from the sensors connected to the disposable base.

16 Claims, 37 Drawing Sheets

Related U.S. Application Data continuation of application No. 15/644,152, filed on Jul. 7, 2017, now Pat. No. 10,617,302.

(60) Provisional application No. 62/463,331, filed on Feb. 24, 2017, provisional application No. 62/359,589, filed on Jul. 7, 2016.

(52) U.S. Cl.
CPC .......... *A61B 5/6824* (2013.01); *A61B 5/6828* (2013.01); *A61B 5/6829* (2013.01); *A61B 5/6831* (2013.01); *A61B 5/742* (2013.01); *A61B 2560/0443* (2013.01)

(58) Field of Classification Search
CPC ..... A61B 5/6829; A61B 5/6831; A61B 5/742; A61B 2560/0443; A61B 5/145
See application file for complete search history.

(56) References Cited

U.S. PATENT DOCUMENTS

| | | |
|---|---|---|
| 3,810,102 A | 5/1974 | Parks, III et al. |
| 3,815,583 A | 6/1974 | Scheidt |
| 3,972,320 A | 8/1976 | Kalman |
| 3,978,849 A | 9/1976 | Geneen |
| 4,108,166 A | 8/1978 | Schmid |
| 4,129,125 A | 12/1978 | Lester et al. |
| 4,226,006 A | 10/1980 | Toyama |
| 4,231,354 A | 11/1980 | Kurtz et al. |
| D265,508 S | 7/1982 | Rusteberg |
| D268,300 S | 3/1983 | Richards |
| 4,589,415 A | 5/1986 | Haaga |
| 4,662,378 A | 5/1987 | Thomis |
| 4,815,172 A | 3/1989 | Ward et al. |
| 4,838,275 A | 6/1989 | Lee |
| 4,852,570 A | 8/1989 | Levine |
| 4,960,128 A | 10/1990 | Gordon et al. |
| 4,964,408 A | 10/1990 | Hink et al. |
| 4,966,154 A | 10/1990 | Cooper et al. |
| 5,041,187 A | 8/1991 | Hink et al. |
| 5,069,213 A | 12/1991 | Hink et al. |
| 5,092,340 A | 3/1992 | Yamaguchi et al. |
| 5,140,519 A | 8/1992 | Friesdorf et al. |
| 5,159,932 A | 11/1992 | Zanetti et al. |
| 5,161,539 A | 11/1992 | Evans et al. |
| 5,163,438 A | 11/1992 | Gordon et al. |
| 5,262,944 A | 11/1993 | Weisner et al. |
| 5,277,189 A | 1/1994 | Jacobs |
| 5,278,627 A | 1/1994 | Aoyagi et al. |
| 5,282,474 A | 2/1994 | Valdes Sosa et al. |
| 5,296,688 A | 3/1994 | Hamilton et al. |
| 5,318,037 A | 6/1994 | Evans et al. |
| 5,319,355 A | 6/1994 | Russek |
| 5,331,549 A | 7/1994 | Crawford, Jr. |
| 5,333,106 A | 7/1994 | Lanpher et al. |
| 5,337,744 A | 8/1994 | Branigan |
| 5,341,805 A | 8/1994 | Stavridi et al. |
| 5,348,008 A | 9/1994 | Bornn et al. |
| 5,358,519 A | 10/1994 | Grandjean |
| D353,195 S | 12/1994 | Savage et al. |
| D353,196 S | 12/1994 | Savage et al. |
| 5,375,599 A | 12/1994 | Schimizu |
| 5,375,604 A | 12/1994 | Kelly |
| 5,377,676 A | 1/1995 | Vari et al. |
| D356,441 S | 3/1995 | Scheller |
| 5,400,794 A | 3/1995 | Gorman |
| D357,982 S | 5/1995 | Dahl et al. |
| 5,416,695 A | 5/1995 | Stutman et al. |
| D359,546 S | 6/1995 | Savage et al. |
| 5,431,170 A | 7/1995 | Mathews |
| 5,434,611 A | 7/1995 | Tamura |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,483,968 A | 1/1996 | Adam et al. |
| 5,490,505 A | 2/1996 | Diab et al. |
| 5,494,041 A | 2/1996 | Wilk |
| 5,494,043 A | 2/1996 | O'Sullivan et al. |
| 5,503,149 A | 4/1996 | Beavin |
| 5,505,202 A | 4/1996 | Mogi et al. |
| 5,533,511 A | 7/1996 | Kaspari et al. |
| 5,534,851 A | 7/1996 | Russek |
| 5,537,289 A | 7/1996 | Dahl |
| 5,544,649 A | 8/1996 | David et al. |
| 5,553,609 A | 9/1996 | Chen et al. |
| 5,558,638 A | 9/1996 | Evers et al. |
| 5,561,275 A | 10/1996 | Savage et al. |
| 5,562,002 A | 10/1996 | Lalin |
| 5,566,676 A | 10/1996 | Rosenfeldt et al. |
| 5,566,678 A | 10/1996 | Rosenfeldt et al. |
| 5,576,952 A | 11/1996 | Stutman et al. |
| 5,579,001 A | 11/1996 | Dempsey et al. |
| 5,590,649 A | 1/1997 | Caro et al. |
| 5,602,924 A | 2/1997 | Durand et al. |
| 5,619,991 A | 4/1997 | Sloane |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,640,967 A | 6/1997 | Fine et al. |
| 5,645,440 A | 7/1997 | Tobler et al. |
| 5,671,914 A | 9/1997 | Kalkhoran et al. |
| 5,685,299 A | 11/1997 | Diab et al. |
| 5,685,314 A | 11/1997 | Geheb et al. |
| 5,687,717 A | 11/1997 | Halpern et al. |
| 5,694,020 A | 12/1997 | Lang |
| 5,724,580 A | 3/1998 | Levin et al. |
| 5,724,983 A | 3/1998 | Selker et al. |
| 5,725,308 A | 3/1998 | Smith et al. |
| 5,726,440 A | 3/1998 | Kalkhoran et al. |
| 5,734,739 A | 3/1998 | Sheehan et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,079 A | 5/1998 | Ludwig et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,772,585 A | 6/1998 | Lavin et al. |
| 5,782,757 A | 7/1998 | Diab et al. |
| 5,782,805 A | 7/1998 | Meinzer |
| 5,785,659 A | 7/1998 | Caro et al. |
| 5,791,347 A | 8/1998 | Flaherty et al. |
| 5,801,637 A | 9/1998 | Lomholt Ole |
| 5,810,734 A | 9/1998 | Caro et al. |
| 5,813,403 A | 9/1998 | Soller et al. |
| 5,822,544 A | 10/1998 | Chaco et al. |
| 5,822,546 A | 10/1998 | George |
| 5,823,950 A | 10/1998 | Diab et al. |
| 5,829,723 A | 11/1998 | Brunner |
| 5,830,131 A | 11/1998 | Caro et al. |
| 5,833,618 A | 11/1998 | Caro et al. |
| 5,855,550 A | 1/1999 | Lai et al. |
| 5,860,919 A | 1/1999 | Kiani-Azarbayjany et al. |
| D406,001 S | 2/1999 | Nemeth |
| 5,876,351 A | 3/1999 | Rohde |
| 5,890,929 A | 4/1999 | Mills et al. |
| 5,904,654 A | 5/1999 | Wohltmann et al. |
| 5,910,139 A | 6/1999 | Cochran et al. |
| 5,919,134 A | 7/1999 | Diab |
| 5,921,920 A | 7/1999 | Marshall et al. |
| 5,924,074 A | 7/1999 | Evans |
| 5,931,160 A | 8/1999 | Gilmore et al. |
| 5,931,791 A | 8/1999 | Saltzstein et al. |
| 5,934,925 A | 8/1999 | Tobler et al. |
| 5,940,182 A | 8/1999 | Lepper, Jr. et al. |
| 5,941,836 A | 8/1999 | Friedman |
| 5,942,986 A | 8/1999 | Shabot et al. |

(56) References Cited

U.S. PATENT DOCUMENTS

| | | |
|---|---|---|
| D415,892 S | 11/1999 | Angus et al. |
| 5,987,343 A | 11/1999 | Kinast |
| 5,987,519 A | 11/1999 | Peifer et al. |
| 5,995,855 A | 11/1999 | Kiani et al. |
| 5,997,343 A | 12/1999 | Mills et al. |
| 6,002,952 A | 12/1999 | Diab et al. |
| 6,006,119 A | 12/1999 | Soller et al. |
| 6,010,937 A | 1/2000 | Karam et al. |
| 6,011,986 A | 1/2000 | Diab et al. |
| 6,014,346 A | 1/2000 | Malone |
| 6,018,673 A | 1/2000 | Chin et al. |
| 6,024,699 A | 2/2000 | Surwit et al. |
| 6,027,452 A | 2/2000 | Flaherty et al. |
| 6,032,678 A | 3/2000 | Rottem |
| 6,035,230 A | 3/2000 | Kang et al. |
| 6,036,642 A | 3/2000 | Diab et al. |
| 6,036,718 A | 3/2000 | Ledford et al. |
| 6,040,578 A | 3/2000 | Malin et al. |
| 6,045,509 A | 4/2000 | Caro et al. |
| 6,045,527 A | 4/2000 | Appelbaum et al. |
| 6,057,758 A | 5/2000 | Dempsey et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,093,146 A | 7/2000 | Filangeri |
| 6,101,478 A | 8/2000 | Brown |
| 6,106,463 A | 8/2000 | Wilk |
| 6,110,522 A | 8/2000 | Lepper, Jr. et al. |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,129,686 A | 10/2000 | Friedman |
| 6,132,218 A | 10/2000 | Benja-Athon |
| 6,139,494 A | 10/2000 | Cairnes |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,167,258 A | 12/2000 | Schmidt et al. |
| D437,058 S | 1/2001 | Gozani |
| 6,168,563 B1 | 1/2001 | Brown |
| 6,171,237 B1 | 1/2001 | Avitall |
| 6,175,752 B1 | 1/2001 | Say et al. |
| 6,183,417 B1 | 2/2001 | Geheb et al. |
| 6,184,521 B1 | 2/2001 | Coffin, IV et al. |
| 6,185,448 B1 | 2/2001 | Borovsky |
| 6,195,576 B1 | 2/2001 | John |
| 6,206,830 B1 | 3/2001 | Diab et al. |
| 6,221,012 B1 | 4/2001 | Maschke et al. |
| 6,224,553 B1 | 5/2001 | Nevo |
| 6,229,856 B1 | 5/2001 | Diab et al. |
| 6,230,142 B1 | 5/2001 | Benigno et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,251,113 B1 | 6/2001 | Appelbaum |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,267,723 B1 | 7/2001 | Matsumura et al. |
| 6,269,262 B1 | 7/2001 | Kandori et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| D449,304 S | 10/2001 | Herath |
| D449,617 S | 10/2001 | Herath |
| 6,301,493 B1 | 10/2001 | Marro et al. |
| 6,304,767 B1 | 10/2001 | Soller et al. |
| 6,308,089 B1 | 10/2001 | von der Ruhr et al. |
| 6,312,378 B1 | 11/2001 | Bardy |
| 6,317,627 B1 | 11/2001 | Ennen et al. |
| 6,319,205 B1 | 11/2001 | Goor et al. |
| 6,321,100 B1 | 11/2001 | Parker |
| 6,322,502 B1 | 11/2001 | Schoenberg et al. |
| 6,322,515 B1 | 11/2001 | Goor et al. |
| D452,495 S | 12/2001 | Murnaghan et al. |
| D452,496 S | 12/2001 | Murnaghan et al. |
| 6,325,761 B1 | 12/2001 | Jay |
| 6,329,139 B1 | 12/2001 | Nova et al. |
| 6,334,065 B1 | 12/2001 | Al-Ali et al. |
| 6,338,039 B1 | 1/2002 | Lonski et al. |
| 6,343,224 B1 | 1/2002 | Parker |
| 6,349,228 B1 | 2/2002 | Kiani et al. |
| 6,352,504 B1 | 3/2002 | Ise |
| 6,354,235 B1 | 3/2002 | Davies |
| 6,360,114 B1 | 3/2002 | Diab et al. |
| 6,363,269 B1 | 3/2002 | Hanna et al. |
| D456,074 S | 4/2002 | McCurry |
| 6,364,834 B1 | 4/2002 | Reuss et al. |
| 6,364,839 B1 | 4/2002 | Little et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,385,476 B1 | 5/2002 | Osadchy et al. |
| 6,385,589 B1 | 5/2002 | Trusheim et al. |
| 6,388,240 B2 | 5/2002 | Schulz et al. |
| 6,397,091 B2 | 5/2002 | Diab et al. |
| 6,407,335 B1 | 6/2002 | Franklin-Lees |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,461,305 B1 | 10/2002 | Schnall |
| 6,463,311 B1 | 10/2002 | Diab |
| 6,470,199 B1 | 10/2002 | Kopotic et al. |
| 6,470,893 B1 | 10/2002 | Boesen |
| 6,487,429 B2 | 11/2002 | Hockersmith et al. |
| 6,488,633 B1 | 12/2002 | Schnall |
| 6,501,975 B2 | 12/2002 | Diab et al. |
| 6,505,059 B1 | 1/2003 | Kollias et al. |
| 6,515,273 B2 | 2/2003 | Al-Ali |
| 6,517,967 B1 | 2/2003 | Shrim et al. |
| 6,519,487 B1 | 2/2003 | Parker |
| 6,524,240 B1 | 2/2003 | Thede |
| 6,525,386 B1 | 2/2003 | Mills et al. |
| 6,526,300 B1 | 2/2003 | Kiani et al. |
| D471,354 S | 3/2003 | Daniels |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,544,173 B2 | 4/2003 | West et al. |
| 6,544,174 B2 | 4/2003 | West et al. |
| 6,551,243 B2 | 4/2003 | Bocionek et al. |
| 6,578,428 B1 | 6/2003 | Dromms et al. |
| 6,580,086 B1 | 6/2003 | Schulz et al. |
| 6,582,393 B2 | 6/2003 | Sage, Jr. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,616,606 B1 | 9/2003 | Peterson et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| D481,537 S | 11/2003 | Vaughn |
| 6,641,533 B2 | 11/2003 | Causey et al. |
| 6,643,530 B2 | 11/2003 | Diab et al. |
| 6,646,556 B1 | 11/2003 | Smith et al. |
| 6,650,917 B2 | 11/2003 | Diab et al. |
| 6,650,939 B2 | 11/2003 | Takpke, II et al. |
| 6,654,624 B2 | 11/2003 | Diab et al. |
| D483,872 S | 12/2003 | Cruz et al. |
| D483,939 S | 12/2003 | Kountz et al. |
| 6,658,276 B2 | 12/2003 | Kiani et al. |

(56) References Cited

U.S. PATENT DOCUMENTS

| | | |
|---|---|---|
| 6,661,161 B1 | 12/2003 | Lanzo et al. |
| 6,663,570 B2 | 12/2003 | Mott et al. |
| 6,671,531 B2 | 12/2003 | Al-Ali |
| 6,678,543 B2 | 1/2004 | Diab et al. |
| 6,684,090 B2 | 1/2004 | Ali et al. |
| 6,684,091 B2 | 1/2004 | Parker |
| 6,694,180 B1 | 2/2004 | Boesen |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,719,694 B2 | 4/2004 | Weng et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,725,086 B2 | 4/2004 | Marinello |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,746,406 B2 | 6/2004 | Lia et al. |
| 6,750,463 B1 | 6/2004 | Riley |
| 6,751,492 B2 | 6/2004 | Ben-haim |
| 6,760,607 B2 | 7/2004 | Al-Ali |
| 6,766,188 B2 | 7/2004 | Soller |
| 6,770,028 B1 | 8/2004 | Ali et al. |
| 6,771,994 B2 | 8/2004 | Kiani et al. |
| 6,783,492 B2 | 8/2004 | Dominguez |
| 6,788,965 B2 | 9/2004 | Ruchti et al. |
| 6,790,178 B1 | 9/2004 | Mault et al. |
| 6,792,300 B1 | 9/2004 | Diab et al. |
| 6,795,724 B2 | 9/2004 | Hogan |
| 6,796,186 B2 | 9/2004 | Lia et al. |
| 6,804,656 B1 | 10/2004 | Rosenfeld |
| 6,807,050 B1 | 10/2004 | Whitehorn et al. |
| 6,813,511 B2 | 11/2004 | Diab et al. |
| 6,816,241 B2 | 11/2004 | Grubisic |
| 6,816,741 B2 | 11/2004 | Diab |
| 6,817,979 B2 | 11/2004 | Nihtila et al. |
| 6,822,564 B2 | 11/2004 | Al-Ali |
| 6,826,419 B2 | 11/2004 | Diab et al. |
| 6,830,711 B2 | 12/2004 | Mills et al. |
| 6,837,848 B2 | 1/2005 | Bonner et al. |
| 6,840,904 B2 | 1/2005 | Goldberg |
| 6,841,535 B2 | 1/2005 | Divita et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,855,112 B2 | 2/2005 | Kao et al. |
| 6,860,266 B2 | 3/2005 | Blike |
| 6,861,639 B2 | 3/2005 | Al-Ali |
| 6,876,931 B2 | 4/2005 | Lorenz et al. |
| 6,897,788 B2 | 5/2005 | Khair et al. |
| 6,898,452 B2 | 5/2005 | Al-Ali et al. |
| 6,907,237 B1 | 6/2005 | Dorenbosch et al. |
| 6,915,149 B2 | 7/2005 | Ben-haim |
| 6,916,289 B2 | 7/2005 | Schnall |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,304 B2 | 9/2005 | Schnall et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| D510,186 S | 10/2005 | Bell |
| 6,952,340 B2 | 10/2005 | Son |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,980,419 B2 | 12/2005 | Smith et al. |
| 6,983,179 B2 | 1/2006 | Ben-haim |
| 6,985,764 B2 | 1/2006 | Mason et al. |
| 6,988,989 B2 | 1/2006 | Weiner et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,997,884 B2 | 2/2006 | Ulmsten |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,004,907 B2 | 2/2006 | Banet et al. |
| 7,015,451 B2 | 3/2006 | Dalke et al. |
| 7,024,233 B2 | 4/2006 | Ali et al. |
| 7,025,729 B2 | 4/2006 | De Chazal et al. |
| 7,027,849 B2 | 4/2006 | Al-Ali |
| 7,030,749 B2 | 4/2006 | Al-Ali |
| 7,033,761 B2 | 4/2006 | Shafer |
| 7,035,686 B2 | 4/2006 | Hogan |
| 7,039,449 B2 | 5/2006 | Al-Ali |
| 7,041,060 B2 | 5/2006 | Flaherty et al. |
| 7,044,918 B2 | 5/2006 | Diab |
| 7,044,930 B2 | 5/2006 | Stromberg |
| 7,048,687 B1 | 5/2006 | Reuss et al. |
| 7,063,666 B2 | 6/2006 | Weng et al. |
| 7,067,893 B2 | 6/2006 | Mills et al. |
| 7,079,035 B2 | 7/2006 | Bock et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,029 S | 9/2006 | Sekine |
| D529,283 S | 10/2006 | Vivar et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,179,228 B2 | 2/2007 | Banet |
| 7,186,966 B2 | 3/2007 | Al-Ali |
| 7,188,621 B2 | 3/2007 | DeVries et al. |
| 7,190,261 B2 | 3/2007 | Al-Ali |
| 7,208,119 B1 | 4/2007 | Kurtock et al. |
| 7,215,984 B2 | 5/2007 | Diab et al. |
| 7,215,986 B2 | 5/2007 | Diab et al. |
| 7,221,971 B2 | 5/2007 | Diab et al. |
| 7,225,006 B2 | 5/2007 | Al-Ali et al. |
| 7,225,007 B2 | 5/2007 | Al-Ali et al. |
| RE39,672 E | 6/2007 | Shehada et al. |
| 7,229,415 B2 | 6/2007 | Schwartz |
| 7,238,159 B2 | 7/2007 | Banet et al. |
| 7,239,905 B2 | 7/2007 | Kiani-Azarbayjany et al. |
| 7,241,287 B2 | 7/2007 | Shehada et al. |
| 7,244,251 B2 | 7/2007 | Shehada et al. |
| 7,245,373 B2 | 7/2007 | Soller et al. |
| 7,245,953 B1 | 7/2007 | Parker |
| 7,252,659 B2 | 8/2007 | Shehada et al. |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,256,708 B2 | 8/2007 | Rosenfeld |
| 7,261,697 B2 | 8/2007 | Berstein |
| 7,264,616 B2 | 9/2007 | Shehada et al. |
| 7,267,671 B2 | 9/2007 | Shehada et al. |
| 7,268,859 B2 | 9/2007 | Sage, Jr. et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,285,090 B2 | 10/2007 | Stivoric |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,298,938 B2 | 11/2007 | Johnston |
| 7,307,543 B2 | 12/2007 | Rosenfeld |
| 7,313,423 B2 | 12/2007 | Griffin et al. |
| 7,314,446 B2 | 1/2008 | Byrd et al. |
| 7,315,825 B2 | 1/2008 | Rosenfeld |
| 7,321,862 B2 | 1/2008 | Rosenfeld |
| 7,322,971 B2 | 1/2008 | Shehada et al. |

(56) References Cited

U.S. PATENT DOCUMENTS

| | | |
|---|---|---|
| 7,328,053 B1 | 2/2008 | Diab et al. |
| 7,332,784 B2 | 2/2008 | Mills et al. |
| 7,336,187 B2 | 2/2008 | Hubbard, Jr. et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,178 B2 | 4/2008 | Ziel et al. |
| 7,356,365 B2 | 4/2008 | Schurman |
| 7,361,155 B2 | 4/2008 | Sage, Jr. et al. |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,378,975 B1 | 5/2008 | Smith et al. |
| 7,382,247 B2 | 6/2008 | Welch et al. |
| 7,383,070 B2 | 6/2008 | Diab et al. |
| 7,390,299 B2 | 6/2008 | Weiner et al. |
| 7,395,158 B2 | 7/2008 | Monfre et al. |
| 7,395,216 B2 | 7/2008 | Rosenfeld |
| 7,396,330 B2 | 7/2008 | Banet et al. |
| 7,411,509 B2 | 8/2008 | Rosenfeld |
| 7,413,546 B2 | 8/2008 | Agutter et al. |
| 7,415,297 B2 | 8/2008 | Al-Ali et al. |
| 7,419,483 B2 | 9/2008 | Shehada |
| 7,428,432 B2 | 9/2008 | Ali et al. |
| 7,433,827 B2 | 10/2008 | Rosenfeld |
| 7,438,683 B2 | 10/2008 | Al-Ali et al. |
| 7,439,856 B2 | 10/2008 | Weiner et al. |
| 7,440,787 B2 | 10/2008 | Diab |
| 7,454,240 B2 | 11/2008 | Diab et al. |
| 7,454,359 B2 | 11/2008 | Rosenfeld |
| 7,454,360 B2 | 11/2008 | Rosenfeld |
| D582,043 S | 12/2008 | Koike et al. |
| 7,462,151 B2 | 12/2008 | Childre et al. |
| 7,467,002 B2 | 12/2008 | Weber et al. |
| 7,467,094 B2 | 12/2008 | Rosenfeld |
| 7,469,157 B2 | 12/2008 | Diab et al. |
| 7,471,969 B2 | 12/2008 | Diab et al. |
| 7,471,971 B2 | 12/2008 | Diab et al. |
| 7,475,019 B2 | 1/2009 | Rosenfeld |
| 7,481,772 B2 | 1/2009 | Banet |
| 7,483,729 B2 | 1/2009 | Al-Ali et al. |
| 7,483,730 B2 | 1/2009 | Diab et al. |
| 7,489,250 B2 | 2/2009 | Bock et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,497,828 B1 | 3/2009 | Wilk et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,515,043 B2 | 4/2009 | Welch et al. |
| 7,515,044 B2 | 4/2009 | Welch et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,532,919 B2 | 5/2009 | Soyemi et al. |
| 7,549,961 B1 | 6/2009 | Hwang |
| 7,551,717 B2 | 6/2009 | Tome et al. |
| D596,635 S | 7/2009 | Owens et al. |
| D597,093 S | 7/2009 | Neu et al. |
| 7,559,520 B2 | 7/2009 | Quijano et al. |
| 7,563,110 B2 | 7/2009 | Al-Ali et al. |
| 7,577,475 B2 | 8/2009 | Consentino et al. |
| 7,588,558 B2 | 9/2009 | Sage, Jr. et al. |
| 7,590,950 B2 | 9/2009 | Collins et al. |
| 7,593,230 B2 | 9/2009 | Abul-Haj et al. |
| 7,596,398 B2 | 9/2009 | Al-Ali et al. |
| 7,597,665 B2 | 10/2009 | Wilk et al. |
| 7,606,608 B2 | 10/2009 | Blank et al. |
| 7,612,999 B2 | 11/2009 | Clark et al. |
| 7,616,303 B2 | 11/2009 | Yang et al. |
| 7,618,375 B2 | 11/2009 | Flaherty et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,639,145 B2 | 12/2009 | Lawson et al. |
| 7,640,140 B2 | 12/2009 | Ruchti et al. |
| 7,647,083 B2 | 1/2010 | Al-Ali et al. |
| 7,650,291 B2 | 1/2010 | Rosenfeld |
| D609,193 S | 2/2010 | Al-Ali et al. |
| 7,654,966 B2 | 2/2010 | Westinskow et al. |
| 7,658,716 B2 | 2/2010 | Banet et al. |
| 7,661,976 B2 | 2/2010 | Ma |
| 7,684,845 B2 | 3/2010 | Juan |
| 7,689,437 B1 | 3/2010 | Teller et al. |
| RE41,236 E | 4/2010 | Seely |
| D614,305 S | 4/2010 | Al-Ali et al. |
| 7,693,697 B2 | 4/2010 | Westinskow et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,722,542 B2 | 5/2010 | Lia et al. |
| 7,729,733 B2 | 6/2010 | Al-Ali et al. |
| 7,734,320 B2 | 6/2010 | Al-Ali |
| 7,736,318 B2 | 6/2010 | Consentino et al. |
| 7,740,590 B2 | 6/2010 | Bernstein |
| 7,761,127 B2 | 7/2010 | Al-Ali et al. |
| 7,761,128 B2 | 7/2010 | Al-Ali et al. |
| 7,763,420 B2 | 7/2010 | Strizker et al. |
| 7,764,982 B2 | 7/2010 | Dalke et al. |
| D621,515 S | 8/2010 | Chua et al. |
| D621,516 S | 8/2010 | Kiani et al. |
| 7,766,818 B2 | 8/2010 | Iketani et al. |
| 7,774,060 B2 | 8/2010 | Westenskow et al. |
| 7,778,851 B2 | 8/2010 | Schoenberg et al. |
| 7,791,155 B2 | 9/2010 | Diab |
| 7,794,407 B2 | 9/2010 | Rothenberg |
| 7,801,581 B2 | 9/2010 | Diab |
| 7,803,120 B2 | 9/2010 | Banet et al. |
| 7,806,830 B2 | 10/2010 | Bernstein |
| 7,820,184 B2 | 10/2010 | Strizker et al. |
| 7,822,452 B2 | 10/2010 | Schurman et al. |
| RE41,912 E | 11/2010 | Parker |
| 7,831,450 B2 | 11/2010 | Schoenberg |
| 7,841,986 B2 | 11/2010 | He et al. |
| 7,844,313 B2 | 11/2010 | Kiani et al. |
| 7,844,314 B2 | 11/2010 | Al-Ali |
| 7,844,315 B2 | 11/2010 | Al-Ali |
| D628,795 S | 12/2010 | Sanders |
| D628,797 S | 12/2010 | Kalbach |
| 7,848,935 B2 | 12/2010 | Gotlib |
| 7,858,322 B2 | 12/2010 | Tymianski et al. |
| 7,865,222 B2 | 1/2011 | Weber et al. |
| 7,865,232 B1 | 1/2011 | Krishnaswamy et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,881,892 B2 | 2/2011 | Soyemi et al. |
| 7,884,314 B2 | 2/2011 | Hamada |
| 7,890,156 B2 | 2/2011 | Ooi et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,914,514 B2 | 3/2011 | Calderon |
| 7,919,713 B2 | 4/2011 | Al-Ali et al. |
| 7,937,128 B2 | 5/2011 | Al-Ali |

(56) References Cited

U.S. PATENT DOCUMENTS

| | | |
|---|---|---|
| 7,937,129 B2 | 5/2011 | Mason et al. |
| 7,937,130 B2 | 5/2011 | Diab et al. |
| 7,941,199 B2 | 5/2011 | Kiani |
| 7,942,691 B1 | 5/2011 | McSweyn |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,963,927 B2 | 6/2011 | Kelleher et al. |
| 7,967,749 B2 | 6/2011 | Hutchinson et al. |
| 7,976,472 B2 | 7/2011 | Kiani |
| 7,988,637 B2 | 8/2011 | Diab |
| 7,988,639 B2 | 8/2011 | Starks |
| 7,990,382 B2 | 8/2011 | Kiani |
| 7,991,446 B2 | 8/2011 | Ali et al. |
| 7,991,463 B2 | 8/2011 | Kelleher et al. |
| 7,991,625 B2 | 8/2011 | Rosenfeld |
| 7,993,275 B2 | 8/2011 | Banet et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,027,846 B2 | 9/2011 | Schoenberg |
| 8,028,701 B2 | 10/2011 | Al-Ali et al. |
| 8,029,765 B2 | 10/2011 | Bellott et al. |
| 8,033,996 B2 | 10/2011 | Behar |
| 8,036,727 B2 | 10/2011 | Schurman et al. |
| 8,036,728 B2 | 10/2011 | Diab et al. |
| 8,036,736 B2 | 10/2011 | Snyder et al. |
| 8,038,625 B2 | 10/2011 | Afonso et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| 8,068,104 B2 | 11/2011 | Rampersad |
| 8,073,707 B2 | 12/2011 | Teller et al. |
| D652,379 S | 1/2012 | Vandiver |
| 8,094,013 B1 | 1/2012 | Lee et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| D659,836 S | 5/2012 | Bensch et al. |
| 8,170,887 B2 | 5/2012 | Rosenfeld |
| 8,175,672 B2 | 5/2012 | Parker |
| 8,175,895 B2 | 5/2012 | Rosenfeld |
| 8,180,420 B2 | 5/2012 | Diab et al. |
| 8,180,440 B2 | 5/2012 | McCombie et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,200,308 B2 | 6/2012 | Zhang et al. |
| 8,200,321 B2 | 6/2012 | McCombie et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,206,312 B2 | 6/2012 | Farquhar |
| 8,214,007 B2 | 7/2012 | Baker et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,235,907 B2 | 8/2012 | Wilk et al. |
| 8,239,010 B2 | 8/2012 | Banet et al. |
| 8,239,780 B2 | 8/2012 | Manetta et al. |
| 8,241,213 B2 | 8/2012 | Lynn et al. |
| 8,244,325 B2 | 8/2012 | Al-Ali et al. |
| 8,249,815 B2 | 8/2012 | Taylor |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| D669,375 S | 10/2012 | Kao et al. |
| 8,280,473 B2 | 10/2012 | Al-Ali |
| 8,294,588 B2 | 10/2012 | Fisher et al. |
| 8,294,716 B2 | 10/2012 | Lord et al. |
| 8,295,521 B2 | 10/2012 | Chan et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,311,747 B2 | 11/2012 | Taylor |
| 8,311,748 B2 | 11/2012 | Taylor et al. |
| 8,315,683 B2 | 11/2012 | Al-Ali et al. |
| 8,315,812 B2 | 11/2012 | Taylor |
| 8,315,813 B2 | 11/2012 | Taylor et al. |
| 8,315,814 B2 | 11/2012 | Taylor et al. |
| 8,321,004 B2 | 11/2012 | Moon et al. |
| 8,321,150 B2 | 11/2012 | Taylor |
| RE43,860 E | 12/2012 | Parker |
| 8,326,649 B2 | 12/2012 | Rosenfeld |
| 8,328,793 B2 | 12/2012 | Birkenbach |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,360,936 B2 | 1/2013 | Dibenedetto et al. |
| 8,364,223 B2 | 1/2013 | Al-Ali et al. |
| 8,364,226 B2 | 1/2013 | Diab et al. |
| 8,364,250 B2 | 1/2013 | Moon et al. |
| 8,374,665 B2 | 2/2013 | Lamego |
| 8,385,995 B2 | 2/2013 | Al-Ali et al. |
| 8,385,996 B2 | 2/2013 | Smith et al. |
| D677,792 S | 3/2013 | Vandiver |
| D679,018 S | 3/2013 | Fullerton et al. |
| 8,388,353 B2 | 3/2013 | Kiani et al. |
| 8,399,822 B2 | 3/2013 | Al-Ali |
| 8,401,602 B2 | 3/2013 | Kiani |
| 8,401,874 B2 | 3/2013 | Rosenfeld |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,419,649 B2 | 4/2013 | Banet et al. |
| 8,423,106 B2 | 4/2013 | Lamego et al. |
| 8,428,967 B2 | 4/2013 | Olsen et al. |
| 8,430,817 B1 | 4/2013 | Al-Ali et al. |
| D682,835 S | 5/2013 | Daniel |
| 8,437,824 B2 | 5/2013 | Moon et al. |
| 8,437,825 B2 | 5/2013 | Dalvi et al. |
| 8,442,607 B2 | 5/2013 | Banet et al. |
| 8,449,469 B2 | 5/2013 | Banet et al. |
| D683,960 S | 6/2013 | Robbins et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| D685,189 S | 7/2013 | Adelman et al. |
| 8,475,370 B2 | 7/2013 | McCombie et al. |
| 8,483,787 B2 | 7/2013 | Al-Ali et al. |
| 8,485,448 B2 | 7/2013 | Maizlin et al. |
| 8,489,167 B2 | 7/2013 | Buxton |
| 8,489,364 B2 | 7/2013 | Weber et al. |
| 8,498,684 B2 | 7/2013 | Weber et al. |
| 8,504,128 B2 | 8/2013 | Blank et al. |
| 8,506,480 B2 | 8/2013 | Banet et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,527,038 B2 | 9/2013 | Moon et al. |
| 8,529,301 B2 | 9/2013 | Al-Ali et al. |
| 8,532,727 B2 | 9/2013 | Ali et al. |
| 8,532,728 B2 | 9/2013 | Diab et al. |

(56) References Cited

U.S. PATENT DOCUMENTS

| | | |
|---|---|---|
| D692,145 S | 10/2013 | Al-Ali et al. |
| 8,545,417 B2 | 10/2013 | Banet et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,554,297 B2 | 10/2013 | Moon et al. |
| 8,560,032 B2 | 10/2013 | Al-Ali et al. |
| 8,560,034 B1 | 10/2013 | Diab et al. |
| 8,565,847 B2 | 10/2013 | Buxton et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,574,161 B2 | 11/2013 | Banet et al. |
| 8,577,431 B2 | 11/2013 | Lamego et al. |
| 8,578,082 B2 | 11/2013 | Medina et al. |
| 8,579,813 B2 | 11/2013 | Causey |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,588,924 B2 | 11/2013 | Dion |
| 8,591,411 B2 | 11/2013 | Banet et al. |
| 8,594,776 B2 | 11/2013 | McCombie et al. |
| 8,597,287 B2 | 12/2013 | Benamou et al. |
| 8,600,467 B2 | 12/2013 | Al-Ali et al. |
| 8,600,777 B2 | 12/2013 | Schoenberg |
| 8,602,997 B2 | 12/2013 | Banet et al. |
| 8,606,342 B2 | 12/2013 | Diab |
| 8,620,678 B2 | 12/2013 | Gotlib |
| D697,626 S | 1/2014 | Laplante et al. |
| 8,622,922 B2 | 1/2014 | Banet et al. |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,672,854 B2 | 3/2014 | McCombie et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| D703,671 S | 4/2014 | Hackett et al. |
| 8,688,183 B2 | 4/2014 | Bruinsma et al. |
| 8,690,771 B2 | 4/2014 | Wekell et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,727,977 B2 | 5/2014 | Banet et al. |
| 8,738,118 B2 | 5/2014 | Moon et al. |
| D706,752 S | 6/2014 | Myung et al. |
| 8,740,792 B1 | 6/2014 | Kiani et al. |
| 8,740,802 B2 | 6/2014 | Banet et al. |
| 8,740,807 B2 | 6/2014 | Banet et al. |
| 8,747,330 B2 | 6/2014 | Banet et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,758,045 B2 | 6/2014 | McSweyn |
| 8,761,850 B2 | 6/2014 | Lamego |
| D709,846 S | 7/2014 | Oswaks |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,808,188 B2 | 8/2014 | Banet et al. |
| 8,818,477 B2 | 8/2014 | Soller |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| D715,667 S | 10/2014 | Shigeno et al. |
| 8,852,094 B2 | 10/2014 | Al-Ali et al. |
| 8,852,994 B2 | 10/2014 | Wojtczuk et al. |
| 8,866,620 B2 | 10/2014 | Amir |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,873,035 B2 | 10/2014 | Yang et al. |
| D717,309 S | 11/2014 | Govindarajan |
| 8,878,888 B2 | 11/2014 | Rosenfeld |
| 8,886,271 B2 | 11/2014 | Kiani et al. |
| 8,888,539 B2 | 11/2014 | Al-Ali et al. |
| 8,888,700 B2 | 11/2014 | Banet et al. |
| 8,888,708 B2 | 11/2014 | Diab et al. |
| 8,892,180 B2 | 11/2014 | Weber et al. |
| 8,897,847 B2 | 11/2014 | Al-Ali |
| D719,668 S | 12/2014 | Cien et al. |
| D719,860 S | 12/2014 | Just et al. |
| 8,907,287 B2 | 12/2014 | Vanderpohl |
| 8,909,310 B2 | 12/2014 | Lamego et al. |
| 8,909,330 B2 | 12/2014 | McCombie et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,951,248 B2 | 2/2015 | Messerly et al. |
| 8,956,292 B2 | 2/2015 | Wekell et al. |
| 8,956,293 B2 | 2/2015 | McCombie et al. |
| 8,956,294 B2 | 2/2015 | McCombie et al. |
| 8,965,471 B2 | 2/2015 | Lamego |
| 8,979,765 B2 | 3/2015 | Banet et al. |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| D728,230 S | 5/2015 | Oas |
| 9,028,429 B2 | 5/2015 | Telfort et al. |
| 9,037,207 B2 | 5/2015 | Al-Ali et al. |
| 9,055,928 B2 | 6/2015 | McCombie et al. |
| 9,057,689 B2 | 6/2015 | Soller |
| 9,060,721 B2 | 6/2015 | Reichgott et al. |
| 9,066,666 B2 | 6/2015 | Kiani |
| 9,066,680 B1 | 6/2015 | Al-Ali et al. |
| D733,598 S | 7/2015 | Just et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,291 B2 | 8/2015 | Soller |
| 9,095,316 B2 | 8/2015 | Welch et al. |
| 9,104,789 B2 | 8/2015 | Gross et al. |
| 9,106,038 B2 | 8/2015 | Telfort et al. |
| 9,107,625 B2 | 8/2015 | Telfort et al. |

(56) References Cited

U.S. PATENT DOCUMENTS

| | | |
|---|---|---|
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| D741,865 S | 10/2015 | Sundermeyer et al. |
| 9,149,192 B2 | 10/2015 | Banet et al. |
| 9,149,228 B2 | 10/2015 | Kinast |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,700 B2 | 10/2015 | Banet et al. |
| 9,161,713 B2 | 10/2015 | Al-Ali et al. |
| 9,167,995 B2 | 10/2015 | Lamego et al. |
| D744,109 S | 11/2015 | Yoneta et al. |
| 9,173,593 B2 | 11/2015 | Banet et al. |
| 9,173,594 B2 | 11/2015 | Banet et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| D745,167 S | 12/2015 | Canas et al. |
| 9,211,072 B2 | 12/2015 | Kiani |
| 9,211,095 B1 | 12/2015 | Al-Ali |
| 9,215,986 B2 | 12/2015 | Banet et al. |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,248,299 B2 | 2/2016 | Toy et al. |
| 9,259,185 B2 | 2/2016 | Abdul-Hafiz et al. |
| 9,262,586 B2 | 2/2016 | Steiger et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,915 B2 | 4/2016 | McCombie et al. |
| 9,307,928 B1 | 4/2016 | Al-Ali et al. |
| 9,318,840 B2 | 4/2016 | Siev et al. |
| 9,323,894 B2 | 4/2016 | Kiani |
| D755,183 S | 5/2016 | Patel et al. |
| D755,392 S | 5/2016 | Hwang et al. |
| 9,326,712 B1 | 5/2016 | Kiani |
| 9,333,316 B2 | 5/2016 | Kiani |
| 9,339,209 B2 | 5/2016 | Banet et al. |
| 9,339,211 B2 | 5/2016 | Banet et al. |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,158 B2 | 6/2016 | Banet et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,380,952 B2 | 7/2016 | Banet et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| D765,083 S | 8/2016 | Breitweiser et al. |
| 9,408,542 B1 | 8/2016 | Kinast et al. |
| 9,408,573 B2 | 8/2016 | Welch et al. |
| 9,436,645 B2 | 9/2016 | Al-Ali et al. |
| 9,439,574 B2 | 9/2016 | McCombie et al. |
| 9,443,059 B2 | 9/2016 | Grubis |
| 9,445,759 B1 | 9/2016 | Lamego et al. |
| D769,973 S | 10/2016 | Benoni |
| 9,466,919 B2 | 10/2016 | Kiani et al. |
| 9,474,474 B2 | 10/2016 | Lamego et al. |
| D771,057 S | 11/2016 | Wurts et al. |
| 9,480,422 B2 | 11/2016 | Al-Ali |
| 9,480,435 B2 | 11/2016 | Olsen |
| 9,480,846 B2 | 11/2016 | Strother et al. |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,529,762 B2 | 12/2016 | Gisler et al. |
| D776,664 S | 1/2017 | Hendrick |
| D776,916 S | 1/2017 | Yeruva et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| D782,483 S | 3/2017 | Patel et al. |
| 9,591,975 B2 | 3/2017 | Dalvi et al. |
| D783,170 S | 4/2017 | Carreon et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,706,964 B2 | 7/2017 | Ferber et al. |
| D794,807 S | 8/2017 | Kranz et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| D803,841 S | 11/2017 | Kim et al. |
| D803,842 S | 11/2017 | Daniel |
| 9,808,188 B1 | 11/2017 | Perea et al. |
| 9,814,418 B2 | 11/2017 | Weber et al. |
| 9,820,691 B2 | 11/2017 | Kiani |
| D804,413 S | 12/2017 | McSweyn et al. |
| 9,833,152 B2 | 12/2017 | Kiani et al. |
| 9,833,180 B2 | 12/2017 | Shakespeare et al. |

(56) References Cited

U.S. PATENT DOCUMENTS

| | | |
|---|---|---|
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali |
| 9,848,807 B2 | 12/2017 | Lamego |
| D808,641 S | 1/2018 | Clover et al. |
| D809,147 S | 1/2018 | Coonahan et al. |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,866,255 B1 | 1/2018 | Ketter-Muldrow |
| 9,867,578 B2 | 1/2018 | Al-Ali et al. |
| 9,872,481 B2 | 1/2018 | Goldfain |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,883,800 B2 | 2/2018 | Pekander |
| 9,891,079 B2 | 2/2018 | Dalvi |
| 9,895,107 B2 | 2/2018 | Al-Ali et al. |
| D812,229 S | 3/2018 | Al-Siddiq |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali et al. |
| 9,973,534 B2 | 5/2018 | Mahaffey et al. |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| D829,574 S | 10/2018 | Mane et al. |
| D831,462 S | 10/2018 | McSweyn et al. |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,726 B2 | 11/2018 | Al-Ali et al. |
| 10,123,729 B2 | 11/2018 | Dyell et al. |
| 10,130,289 B2 | 11/2018 | Al-Ali et al. |
| 10,130,291 B2 | 11/2018 | Schurman et al. |
| 10,130,306 B2 | 11/2018 | Katra et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Kiani et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,215 B2 | 3/2019 | Cohrs et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,271,748 B2 | 4/2019 | Al-Ali |
| 10,278,626 B2 | 5/2019 | Schurman et al. |
| 10,278,648 B2 | 5/2019 | Al-Ali et al. |
| 10,279,247 B2 | 5/2019 | Kiani |
| 10,292,628 B1 | 5/2019 | Poeze et al. |
| 10,292,657 B2 | 5/2019 | Abdul-Hafiz et al. |
| 10,292,664 B2 | 5/2019 | Al-Ali |
| 10,299,708 B1 | 5/2019 | Poeze et al. |
| 10,299,709 B2 | 5/2019 | Perea et al. |
| 10,299,720 B2 | 5/2019 | Brown et al. |
| 10,305,775 B2 | 5/2019 | Lamego et al. |
| D850,628 S | 6/2019 | De Hoog et al. |
| 10,307,111 B2 | 6/2019 | Muhsin et al. |
| 10,325,681 B2 | 6/2019 | Sampath et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,335,033 B2 | 7/2019 | Al-Ali |
| 10,335,068 B2 | 7/2019 | Poeze et al. |
| 10,335,072 B2 | 7/2019 | Al-Ali et al. |
| 10,342,470 B2 | 7/2019 | Al-Ali et al. |
| 10,342,487 B2 | 7/2019 | Al-Ali et al. |
| 10,342,497 B2 | 7/2019 | Al-Ali et al. |
| 10,349,895 B2 | 7/2019 | Telfort et al. |
| 10,349,898 B2 | 7/2019 | Al-Ali et al. |
| 10,354,504 B2 | 7/2019 | Kiani et al. |
| 10,357,206 B2 | 7/2019 | Weber et al. |
| 10,357,209 B2 | 7/2019 | Al-Ali |
| 10,366,787 B2 | 7/2019 | Sampath et al. |
| 10,368,787 B2 | 8/2019 | Reichgott et al. |
| 10,374,350 B2 | 8/2019 | Nakazono et al. |
| 10,376,190 B1 | 8/2019 | Poeze et al. |
| 10,376,191 B1 | 8/2019 | Poeze et al. |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| 10,398,320 B2 | 9/2019 | Kiani et al. |
| 10,405,804 B2 | 9/2019 | Al-Ali |
| 10,413,666 B2 | 9/2019 | Al-Ali et al. |
| 10,420,493 B2 | 9/2019 | Al-Ali et al. |
| D864,120 S | 10/2019 | Forrest et al. |
| 10,433,776 B2 | 10/2019 | Al-Ali |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| D874,657 S | 2/2020 | Bailey et al. |
| 10,555,678 B2 | 2/2020 | Dalvi et al. |
| 10,560,532 B2 | 2/2020 | Yang et al. |
| 10,568,553 B2 | 2/2020 | O'Neil et al. |
| RE47,882 E | 3/2020 | Al-Ali |

(56) References Cited

U.S. PATENT DOCUMENTS

| | | |
|---|---|---|
| 10,608,817 B2 | 3/2020 | Haider et al. |
| D880,477 S | 4/2020 | Forrest et al. |
| D881,889 S | 4/2020 | Wang et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| 10,638,982 B2 | 5/2020 | Ferber et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,736,552 B2 | 8/2020 | Ferber et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,842,395 B2 | 11/2020 | Schnall et al. |
| 10,849,554 B2 | 12/2020 | Shreim et al. |
| 10,856,750 B2 | 12/2020 | Indorf et al. |
| D906,970 S | 1/2021 | Forrest et al. |
| D908,213 S | 1/2021 | Abdul-Hafiz et al. |
| D910,623 S | 2/2021 | Cueto et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D916,705 S | 4/2021 | Liao |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| D933,951 S | 10/2021 | Cardentey |
| 11,145,408 B2 | 10/2021 | Sampath et al. |
| 11,147,518 B1 | 10/2021 | Al-Ali et al. |
| 11,179,107 B2 | 11/2021 | Chae et al. |
| 11,185,262 B2 | 11/2021 | Al-Ali et al. |
| 11,191,484 B2 | 12/2021 | Kiani et al. |
| 11,201,500 B2 | 12/2021 | Partovi et al. |
| 11,202,571 B2 | 12/2021 | Al-Ali et al. |
| D944,520 S | 3/2022 | Akana et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,259,753 B2 | 3/2022 | Ferber et al. |
| 11,260,238 B2 | 3/2022 | Finch et al. |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| D967,625 S | 10/2022 | Akana et al. |
| 11,457,703 B2 | 10/2022 | Calder |
| 11,457,733 B2 | 10/2022 | Gallup et al. |
| 11,464,410 B2 | 10/2022 | Muhsin |
| D968,410 S | 11/2022 | Zhang et al. |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 11,755,879 B2 | 9/2023 | Pascanu et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| 11,872,156 B2 | 1/2024 | Telfort et al. |
| 11,879,960 B2 | 1/2024 | Ranasinghe et al. |
| 2001/0011355 A1 | 8/2001 | Kawai |
| 2001/0031922 A1 | 10/2001 | Weng et al. |
| 2001/0034477 A1 | 10/2001 | Mansfield et al. |
| 2001/0039483 A1 | 11/2001 | Brand et al. |
| 2001/0046366 A1 | 11/2001 | Susskind |
| 2002/0010401 A1 | 1/2002 | Bushmakin et al. |
| 2002/0045836 A1 | 4/2002 | Alkawwas |
| 2002/0052311 A1 | 5/2002 | Solomon et al. |
| 2002/0058864 A1 | 5/2002 | Mansfield et al. |
| 2002/0063690 A1 | 5/2002 | Chung et al. |
| 2002/0072681 A1 | 6/2002 | Schnall |
| 2002/0133080 A1 | 9/2002 | Apruzzese et al. |
| 2002/0140675 A1 | 10/2002 | Ali et al. |
| 2002/0169439 A1 | 11/2002 | Flaherty |
| 2002/0177758 A1 | 11/2002 | Schoenberg |
| 2002/0198445 A1 | 12/2002 | Dominguez et al. |
| 2003/0004423 A1 | 1/2003 | Levie et al. |
| 2003/0013975 A1 | 1/2003 | Kiani |
| 2003/0018243 A1 | 1/2003 | Gerhardt et al. |
| 2003/0027326 A1 | 2/2003 | Ulmsten et al. |
| 2003/0052787 A1 | 3/2003 | Zerhusen et al. |
| 2003/0058838 A1 | 3/2003 | Wengrovitz |
| 2003/0144582 A1 | 7/2003 | Cohen et al. |
| 2003/0156288 A1 | 8/2003 | Barnum et al. |
| 2003/0158466 A1 | 8/2003 | Lynn et al. |
| 2003/0212312 A1 | 11/2003 | Coffin, IV et al. |
| 2003/0216670 A1 | 11/2003 | Beggs |
| 2004/0013647 A1 | 1/2004 | Solomon et al. |

(56) References Cited

U.S. PATENT DOCUMENTS

| | | |
|---|---|---|
| 2004/0073095 A1 | 4/2004 | Causey et al. |
| 2004/0090742 A1 | 5/2004 | Son et al. |
| 2004/0106163 A1 | 6/2004 | Workman, Jr. et al. |
| 2004/0116787 A1 | 6/2004 | Schnall |
| 2004/0122787 A1 | 6/2004 | Avinash et al. |
| 2004/0126007 A1 | 7/2004 | Ziel et al. |
| 2004/0139571 A1 | 7/2004 | Chang et al. |
| 2004/0147818 A1 | 7/2004 | Levy et al. |
| 2004/0152957 A1 | 8/2004 | Stivoric et al. |
| 2004/0179332 A1 | 9/2004 | Smith et al. |
| 2004/0186357 A1 | 9/2004 | Soderberg et al. |
| 2004/0215085 A1 | 10/2004 | Schnall |
| 2004/0230118 A1 | 11/2004 | Shehada et al. |
| 2004/0230132 A1 | 11/2004 | Shehada et al. |
| 2004/0230179 A1 | 11/2004 | Shehada et al. |
| 2004/0243017 A1 | 12/2004 | Causevic |
| 2004/0249670 A1 | 12/2004 | Noguchi et al. |
| 2004/0254431 A1 | 12/2004 | Shehada et al. |
| 2004/0254432 A1 | 12/2004 | Shehada et al. |
| 2004/0267103 A1 | 12/2004 | Li et al. |
| 2005/0005710 A1 | 1/2005 | Sage, Jr. |
| 2005/0009926 A1 | 1/2005 | Kreye et al. |
| 2005/0020918 A1 | 1/2005 | Wilk et al. |
| 2005/0038332 A1 | 2/2005 | Saidara et al. |
| 2005/0038680 A1 | 2/2005 | McMahon |
| 2005/0055276 A1 | 3/2005 | Kiani et al. |
| 2005/0065417 A1 | 3/2005 | Al Ali et al. |
| 2005/0080336 A1 | 4/2005 | Byrd et al. |
| 2005/0096542 A1 | 5/2005 | Weng et al. |
| 2005/0113653 A1 | 5/2005 | Fox et al. |
| 2005/0124864 A1 | 6/2005 | Mack et al. |
| 2005/0125256 A1 | 6/2005 | Schoenberg |
| 2005/0148882 A1 | 7/2005 | Banet et al. |
| 2005/0164933 A1 | 7/2005 | Tymianski et al. |
| 2005/0191294 A1 | 9/2005 | Arap et al. |
| 2005/0208648 A1 | 9/2005 | Sage, Jr. et al. |
| 2005/0209518 A1 | 9/2005 | Sage, Jr. et al. |
| 2005/0228244 A1 | 10/2005 | Banet |
| 2005/0228299 A1 | 10/2005 | Banet |
| 2005/0234317 A1 | 10/2005 | Kiani |
| 2005/0242946 A1 | 11/2005 | Hubbard, Jr. et al. |
| 2005/0245831 A1 | 11/2005 | Banet |
| 2005/0245839 A1 | 11/2005 | Stivoric et al. |
| 2005/0261594 A1 | 11/2005 | Banet |
| 2005/0261598 A1 | 11/2005 | Banet et al. |
| 2005/0268401 A1 | 12/2005 | Dixon et al. |
| 2005/0277872 A1 | 12/2005 | Colby et al. |
| 2006/0009697 A1 | 1/2006 | Banet et al. |
| 2006/0009698 A1 | 1/2006 | Banet et al. |
| 2006/0049936 A1 | 3/2006 | Collins, Jr. et al. |
| 2006/0058647 A1 | 3/2006 | Strommer et al. |
| 2006/0073719 A1 | 4/2006 | Kiani |
| 2006/0084878 A1 | 4/2006 | Banet et al. |
| 2006/0085952 A1 | 4/2006 | Kaneko et al. |
| 2006/0089543 A1 | 4/2006 | Kim et al. |
| 2006/0094936 A1 | 5/2006 | Russ |
| 2006/0104824 A1 | 5/2006 | Schnall |
| 2006/0149393 A1 | 7/2006 | Calderon |
| 2006/0155175 A1 | 7/2006 | Ogino et al. |
| 2006/0161054 A1 | 7/2006 | Reuss et al. |
| 2006/0189871 A1 | 8/2006 | Al-Ali et al. |
| 2006/0200009 A1 | 9/2006 | Wekell et al. |
| 2006/0217684 A1 | 9/2006 | Shehada et al. |
| 2006/0217685 A1 | 9/2006 | Shehada et al. |
| 2006/0224413 A1 | 10/2006 | Kim et al. |
| 2006/0235300 A1 | 10/2006 | Weng et al. |
| 2006/0253042 A1 | 11/2006 | Stahmann et al. |
| 2007/0000490 A1 | 1/2007 | DeVries et al. |
| 2007/0002533 A1 | 1/2007 | Kogan et al. |
| 2007/0021675 A1 | 1/2007 | Childre et al. |
| 2007/0027368 A1 | 2/2007 | Collins et al. |
| 2007/0032733 A1 | 2/2007 | Burton et al. |
| 2007/0038050 A1 | 2/2007 | Sarussi |
| 2007/0055116 A1 | 3/2007 | Clark et al. |
| 2007/0055544 A1 | 3/2007 | Jung et al. |
| 2007/0060798 A1 | 3/2007 | Krupnik et al. |
| 2007/0073116 A1 | 3/2007 | Kiani et al. |
| 2007/0088406 A1 | 4/2007 | Bennett et al. |
| 2007/0096897 A1 | 5/2007 | Weiner |
| 2007/0100222 A1 | 5/2007 | Mastrototaro et al. |
| 2007/0118399 A1 | 5/2007 | Avinash et al. |
| 2007/0140475 A1 | 6/2007 | Kurtock et al. |
| 2007/0142715 A1 | 6/2007 | Banet et al. |
| 2007/0156033 A1 | 7/2007 | Causey et al. |
| 2007/0157285 A1 | 7/2007 | Frank et al. |
| 2007/0159332 A1 | 7/2007 | Koblasz |
| 2007/0163589 A1 | 7/2007 | DeVries et al. |
| 2007/0180140 A1 | 8/2007 | Welch et al. |
| 2007/0185390 A1 | 8/2007 | Perkins et al. |
| 2007/0185393 A1 | 8/2007 | Zhou et al. |
| 2007/0232941 A1 | 10/2007 | Rabinovich |
| 2007/0244377 A1 | 10/2007 | Cozad et al. |
| 2007/0244724 A1 | 10/2007 | Pendergast et al. |
| 2007/0250286 A1 | 10/2007 | Duncan et al. |
| 2007/0255114 A1 | 11/2007 | Ackermann et al. |
| 2007/0255116 A1 | 11/2007 | Mehta et al. |
| 2007/0255250 A1 | 11/2007 | Moberg |
| 2007/0276261 A1 | 11/2007 | Banet et al. |
| 2007/0276262 A1 | 11/2007 | Banet et al. |
| 2007/0276632 A1 | 11/2007 | Banet et al. |
| 2007/0282478 A1 | 12/2007 | Al-Ali et al. |
| 2007/0287898 A1 | 12/2007 | Lee et al. |
| 2008/0000479 A1 | 1/2008 | Elaz et al. |
| 2008/0003200 A1 | 1/2008 | Arap et al. |
| 2008/0021854 A1 | 1/2008 | Jung et al. |
| 2008/0033661 A1 | 2/2008 | Syroid et al. |
| 2008/0039701 A1 | 2/2008 | Ali et al. |
| 2008/0051670 A1 | 2/2008 | Banet et al. |
| 2008/0053438 A1 | 3/2008 | DeVries et al. |
| 2008/0058614 A1 | 3/2008 | Banet et al. |
| 2008/0058657 A1 | 3/2008 | Schwartz et al. |
| 2008/0064965 A1 | 3/2008 | Jay et al. |
| 2008/0077024 A1 | 3/2008 | Schnall |
| 2008/0077026 A1 | 3/2008 | Banet et al. |
| 2008/0082004 A1 | 4/2008 | Banet et al. |
| 2008/0090626 A1 | 4/2008 | Griffin et al. |
| 2008/0091089 A1 | 4/2008 | Guillory et al. |
| 2008/0091090 A1 | 4/2008 | Guillory et al. |
| 2008/0091471 A1 | 4/2008 | Michon et al. |
| 2008/0094228 A1 | 4/2008 | Welch et al. |
| 2008/0097167 A1 | 4/2008 | Yudkovitch et al. |
| 2008/0099366 A1 | 5/2008 | Niemiec et al. |
| 2008/0103375 A1 | 5/2008 | Kiani |
| 2008/0108884 A1 | 5/2008 | Al-Ali et al. |
| 2008/0114220 A1 | 5/2008 | Banet et al. |
| 2008/0119412 A1 | 5/2008 | Tymianski et al. |
| 2008/0138278 A1 | 6/2008 | Scherz et al. |
| 2008/0139354 A1 | 6/2008 | Bell et al. |
| 2008/0169922 A1 | 7/2008 | Issokson |
| 2008/0171919 A1 | 7/2008 | Stivoric et al. |
| 2008/0188795 A1 | 8/2008 | Katz et al. |
| 2008/0194918 A1 | 8/2008 | Kulik et al. |
| 2008/0208912 A1 | 8/2008 | Garibaldi |
| 2008/0221396 A1 | 9/2008 | Garces et al. |
| 2008/0221399 A1 | 9/2008 | Zhou et al. |
| 2008/0221418 A1 | 9/2008 | Al-Ali et al. |
| 2008/0221461 A1 | 9/2008 | Zhou et al. |
| 2008/0228077 A1 | 9/2008 | Wilk et al. |
| 2008/0275309 A1 | 11/2008 | Stivoric et al. |
| 2008/0281167 A1 | 11/2008 | Soderberg et al. |
| 2008/0281168 A1 | 11/2008 | Gibson et al. |
| 2008/0281181 A1 | 11/2008 | Manzione et al. |
| 2008/0287751 A1 | 11/2008 | Stivoric et al. |
| 2008/0292172 A1 | 11/2008 | Assmann et al. |
| 2008/0300020 A1 | 12/2008 | Nishizawa et al. |
| 2008/0312518 A1 | 12/2008 | Jina et al. |
| 2008/0312542 A1 | 12/2008 | Banet et al. |
| 2008/0319275 A1 | 12/2008 | Chiu et al. |
| 2008/0319327 A1 | 12/2008 | Banet et al. |
| 2008/0319354 A1 | 12/2008 | Bell et al. |
| 2009/0005651 A1 | 1/2009 | Ward et al. |
| 2009/0018409 A1 | 1/2009 | Banet et al. |
| 2009/0018422 A1 | 1/2009 | Banet et al. |
| 2009/0018453 A1 | 1/2009 | Banet et al. |

(56) References Cited

U.S. PATENT DOCUMENTS

| | | |
|---|---|---|
| 2009/0018808 A1 | 1/2009 | Bronstein et al. |
| 2009/0024008 A1 | 1/2009 | Brunner et al. |
| 2009/0036759 A1 | 2/2009 | Ault et al. |
| 2009/0043172 A1 | 2/2009 | Zagorchev et al. |
| 2009/0052623 A1 | 2/2009 | Tome et al. |
| 2009/0054735 A1 | 2/2009 | Higgins et al. |
| 2009/0054743 A1 | 2/2009 | Stewart |
| 2009/0062682 A1 | 3/2009 | Bland et al. |
| 2009/0069642 A1 | 3/2009 | Gao et al. |
| 2009/0069868 A1 | 3/2009 | Bengtsson et al. |
| 2009/0093687 A1 | 4/2009 | Telfort et al. |
| 2009/0095926 A1 | 4/2009 | MacNeish, III |
| 2009/0099480 A1 | 4/2009 | Salgo et al. |
| 2009/0112072 A1 | 4/2009 | Banet et al. |
| 2009/0118628 A1 | 5/2009 | Zhou et al. |
| 2009/0119330 A1 | 5/2009 | Sampath et al. |
| 2009/0119843 A1 | 5/2009 | Rodgers et al. |
| 2009/0124867 A1 | 5/2009 | Hirsch et al. |
| 2009/0131759 A1 | 5/2009 | Sims et al. |
| 2009/0143832 A1 | 6/2009 | Saba |
| 2009/0157058 A1 | 6/2009 | Ferren et al. |
| 2009/0171170 A1 | 7/2009 | Li et al. |
| 2009/0171225 A1 | 7/2009 | Gadodia et al. |
| 2009/0177090 A1 | 7/2009 | Grunwald et al. |
| 2009/0182287 A1 | 7/2009 | Kassab |
| 2009/0226372 A1 | 9/2009 | Ruoslahti et al. |
| 2009/0247924 A1 | 10/2009 | Harima et al. |
| 2009/0247984 A1 | 10/2009 | Lamego et al. |
| 2009/0264778 A1 | 10/2009 | Markowitz et al. |
| 2009/0275813 A1 | 11/2009 | Davis |
| 2009/0275844 A1 | 11/2009 | Al-Ali |
| 2009/0281462 A1 | 11/2009 | Heliot et al. |
| 2009/0299157 A1 | 12/2009 | Telfort et al. |
| 2009/0309755 A1 | 12/2009 | Williamson et al. |
| 2009/0322540 A1 | 12/2009 | Richardson et al. |
| 2010/0004518 A1 | 1/2010 | Vo et al. |
| 2010/0030040 A1 | 2/2010 | Poeze et al. |
| 2010/0030094 A1 | 2/2010 | Lundback |
| 2010/0036209 A1 | 2/2010 | Ferren et al. |
| 2010/0056886 A1 | 3/2010 | Hurtubise et al. |
| 2010/0069725 A1 | 3/2010 | Al-Ali |
| 2010/0099964 A1 | 4/2010 | O'Reilly et al. |
| 2010/0125217 A1 | 5/2010 | Kuo et al. |
| 2010/0130875 A1 | 5/2010 | Banet et al. |
| 2010/0144627 A1 | 6/2010 | Vitek et al. |
| 2010/0160794 A1 | 6/2010 | Banet et al. |
| 2010/0160795 A1 | 6/2010 | Banet et al. |
| 2010/0160796 A1 | 6/2010 | Banet et al. |
| 2010/0160797 A1 | 6/2010 | Banet et al. |
| 2010/0160798 A1 | 6/2010 | Banet et al. |
| 2010/0168536 A1 | 7/2010 | Banet et al. |
| 2010/0168589 A1 | 7/2010 | Banet et al. |
| 2010/0185101 A1 | 7/2010 | Sakai et al. |
| 2010/0198622 A1 | 8/2010 | Gajic et al. |
| 2010/0210958 A1 | 8/2010 | Manwaring et al. |
| 2010/0234718 A1 | 9/2010 | Sampath et al. |
| 2010/0261979 A1 | 10/2010 | Al-Ali et al. |
| 2010/0261982 A1 | 10/2010 | Noury et al. |
| 2010/0270257 A1 | 10/2010 | Wachman et al. |
| 2010/0298650 A1 | 11/2010 | Moon et al. |
| 2010/0298651 A1 | 11/2010 | Moon et al. |
| 2010/0298652 A1 | 11/2010 | McCombie et al. |
| 2010/0298653 A1 | 11/2010 | McCombie et al. |
| 2010/0298654 A1 | 11/2010 | McCombie et al. |
| 2010/0298655 A1 | 11/2010 | McCombie et al. |
| 2010/0298656 A1 | 11/2010 | McCombie et al. |
| 2010/0298657 A1 | 11/2010 | McCombie et al. |
| 2010/0298658 A1 | 11/2010 | McCombie et al. |
| 2010/0298659 A1 | 11/2010 | Mccombie et al. |
| 2010/0298660 A1 | 11/2010 | McCombie et al. |
| 2010/0298661 A1 | 11/2010 | Mccombie et al. |
| 2010/0298742 A1 | 11/2010 | Perlman et al. |
| 2010/0305412 A1 | 12/2010 | Darrah et al. |
| 2010/0312103 A1 | 12/2010 | Gorek et al. |
| 2010/0317936 A1 | 12/2010 | Al-Ali et al. |
| 2010/0317951 A1 | 12/2010 | Rutkowski et al. |
| 2010/0324384 A1 | 12/2010 | Moon et al. |
| 2010/0324385 A1 | 12/2010 | Moon et al. |
| 2010/0324386 A1 | 12/2010 | Moon et al. |
| 2010/0324387 A1 | 12/2010 | Moon et al. |
| 2010/0324388 A1 | 12/2010 | Moon et al. |
| 2010/0324389 A1 | 12/2010 | Moon et al. |
| 2011/0001605 A1 | 1/2011 | Kiani et al. |
| 2011/0004079 A1 | 1/2011 | Al-Ali et al. |
| 2011/0021930 A1 | 1/2011 | Mazzeo et al. |
| 2011/0023130 A1 | 1/2011 | Gudgel et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0046495 A1 | 2/2011 | Osypka |
| 2011/0066051 A1 | 3/2011 | Moon et al. |
| 2011/0077473 A1 | 3/2011 | Lisogurski |
| 2011/0077488 A1 | 3/2011 | Buxton et al. |
| 2011/0078596 A1 | 3/2011 | Rawlins et al. |
| 2011/0080294 A1 | 4/2011 | Tanishima et al. |
| 2011/0082711 A1 | 4/2011 | Poeze et al. |
| 2011/0087081 A1 | 4/2011 | Kiani et al. |
| 2011/0087083 A1 | 4/2011 | Poeze et al. |
| 2011/0087084 A1 | 4/2011 | Jeong et al. |
| 2011/0087117 A1 | 4/2011 | Tremper et al. |
| 2011/0087756 A1 | 4/2011 | Biondi |
| 2011/0092831 A1 | 4/2011 | Herscovivi-Cohen et al. |
| 2011/0092857 A1 | 4/2011 | Herscovivi-Cohen et al. |
| 2011/0098583 A1 | 4/2011 | Pandia et al. |
| 2011/0105854 A1 | 5/2011 | Kiani et al. |
| 2011/0105956 A1 | 5/2011 | Hirth |
| 2011/0118561 A1 | 5/2011 | Tari et al. |
| 2011/0118573 A1 | 5/2011 | Mckenna |
| 2011/0125060 A1 | 5/2011 | Telfort et al. |
| 2011/0137297 A1 | 6/2011 | Kiani et al. |
| 2011/0152629 A1 | 6/2011 | Eaton et al. |
| 2011/0172498 A1 | 7/2011 | Olsen et al. |
| 2011/0172967 A1 | 7/2011 | Al-Ali et al. |
| 2011/0184252 A1 | 7/2011 | Archer et al. |
| 2011/0184253 A1 | 7/2011 | Archer et al. |
| 2011/0208015 A1 | 8/2011 | Welch et al. |
| 2011/0208018 A1 | 8/2011 | Kiani |
| 2011/0208073 A1 | 8/2011 | Matsukawa et al. |
| 2011/0209915 A1 | 9/2011 | Telfort et al. |
| 2011/0212090 A1 | 9/2011 | Pedersen et al. |
| 2011/0213212 A1 | 9/2011 | Al-Ali |
| 2011/0213271 A1 | 9/2011 | Telfort et al. |
| 2011/0224498 A1 | 9/2011 | Banet et al. |
| 2011/0224499 A1 | 9/2011 | Banet et al. |
| 2011/0224500 A1 | 9/2011 | Banet et al. |
| 2011/0224506 A1 | 9/2011 | Moon et al. |
| 2011/0224507 A1 | 9/2011 | Banet et al. |
| 2011/0224508 A1 | 9/2011 | Moon et al. |
| 2011/0224556 A1 | 9/2011 | Moon et al. |
| 2011/0224557 A1 | 9/2011 | Banet et al. |
| 2011/0224564 A1 | 9/2011 | Moon et al. |
| 2011/0230733 A1 | 9/2011 | Al-Ali |
| 2011/0237911 A1 | 9/2011 | Lamego et al. |
| 2011/0237969 A1 | 9/2011 | Eckerbom et al. |
| 2011/0257489 A1 | 10/2011 | Banet et al. |
| 2011/0257544 A1 | 10/2011 | Kaasinen et al. |
| 2011/0257551 A1 | 10/2011 | Banet et al. |
| 2011/0257552 A1 | 10/2011 | Banet et al. |
| 2011/0257553 A1 | 10/2011 | Banet et al. |
| 2011/0257554 A1 | 10/2011 | Banet et al. |
| 2011/0257555 A1 | 10/2011 | Banet et al. |
| 2011/0263950 A1 | 10/2011 | Larson et al. |
| 2011/0288383 A1 | 11/2011 | Diab |
| 2011/0288421 A1 | 11/2011 | Banet et al. |
| 2011/0295094 A1 | 12/2011 | Doyle et al. |
| 2011/0301444 A1 | 12/2011 | Al-Ali |
| 2012/0004579 A1 | 1/2012 | Luo et al. |
| 2012/0029300 A1 | 2/2012 | Paquet |
| 2012/0029304 A1 | 2/2012 | Medina et al. |
| 2012/0029879 A1 | 2/2012 | Sing et al. |
| 2012/0041316 A1 | 2/2012 | Al Ali et al. |
| 2012/0046557 A1 | 2/2012 | Kiani |
| 2012/0059230 A1 | 3/2012 | Teller et al. |
| 2012/0059267 A1 | 3/2012 | Lamego et al. |

(56) References Cited

U.S. PATENT DOCUMENTS

| | | |
|---|---|---|
| 2012/0071771 A1 | 3/2012 | Behar |
| 2012/0075464 A1 | 3/2012 | Derenne et al. |
| 2012/0088984 A1 | 4/2012 | Al-Ali et al. |
| 2012/0095778 A1 | 4/2012 | Gross et al. |
| 2012/0101353 A1 | 4/2012 | Reggiardo et al. |
| 2012/0108983 A1 | 5/2012 | Banet et al. |
| 2012/0116175 A1 | 5/2012 | Al-Ali et al. |
| 2012/0123231 A1 | 5/2012 | O'Reilly |
| 2012/0123799 A1 | 5/2012 | Nolen et al. |
| 2012/0132717 A1 | 5/2012 | Maizlin et al. |
| 2012/0136221 A1 | 5/2012 | Killen et al. |
| 2012/0157806 A1 | 6/2012 | Stelger |
| 2012/0165629 A1 | 6/2012 | Merritt et al. |
| 2012/0165630 A1 | 6/2012 | Knight et al. |
| 2012/0179006 A1 | 7/2012 | Jansen et al. |
| 2012/0179011 A1 | 7/2012 | Moon et al. |
| 2012/0184120 A1 | 7/2012 | Basta et al. |
| 2012/0190949 A1 | 7/2012 | McCombie et al. |
| 2012/0197619 A1 | 8/2012 | Namer Yelin et al. |
| 2012/0203078 A1 | 8/2012 | Sze et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0226160 A1 | 9/2012 | Kudoh |
| 2012/0227739 A1 | 9/2012 | Kiani |
| 2012/0239434 A1 | 9/2012 | Breslow et al. |
| 2012/0242501 A1 | 9/2012 | Tran et al. |
| 2012/0265039 A1 | 10/2012 | Kiani |
| 2012/0282583 A1 | 11/2012 | Thaler et al. |
| 2012/0283524 A1 | 11/2012 | Kiani et al. |
| 2012/0284053 A1 | 11/2012 | Rosenfeld |
| 2012/0286955 A1 | 11/2012 | Welch et al. |
| 2012/0294801 A1 | 11/2012 | Scherz et al. |
| 2012/0296174 A1 | 11/2012 | McCombie |
| 2012/0296178 A1 | 11/2012 | Lamego et al. |
| 2012/0302894 A1 | 11/2012 | Diab et al. |
| 2012/0303476 A1 | 11/2012 | Krzyzanowski et al. |
| 2012/0319816 A1 | 12/2012 | Al-Ali |
| 2012/0330112 A1 | 12/2012 | Lamego et al. |
| 2013/0006131 A1 | 1/2013 | Narayan et al. |
| 2013/0006151 A1 | 1/2013 | Main et al. |
| 2013/0023775 A1 | 1/2013 | Lamego et al. |
| 2013/0035603 A1 | 2/2013 | Jarausch et al. |
| 2013/0041591 A1 | 2/2013 | Lamego |
| 2013/0045685 A1 | 2/2013 | Kiani |
| 2013/0046197 A1 | 2/2013 | Dlugos et al. |
| 2013/0046204 A1 | 2/2013 | Lamego et al. |
| 2013/0060108 A1 | 3/2013 | Schurman et al. |
| 2013/0060147 A1 | 3/2013 | Welch et al. |
| 2013/0079610 A1 | 3/2013 | Al-Ali |
| 2013/0092805 A1 | 4/2013 | Funk et al. |
| 2013/0096405 A1 | 4/2013 | Garfio |
| 2013/0096936 A1 | 4/2013 | Sampath et al. |
| 2013/0109929 A1 | 5/2013 | Menzel |
| 2013/0109935 A1 | 5/2013 | Al-Ali et al. |
| 2013/0109937 A1 | 5/2013 | Banet et al. |
| 2013/0116515 A1 | 5/2013 | Banet et al. |
| 2013/0123616 A1 | 5/2013 | Merritt et al. |
| 2013/0162433 A1 | 6/2013 | Muhsin et al. |
| 2013/0178749 A1 | 7/2013 | Lamego |
| 2013/0190581 A1 | 7/2013 | Al-Ali et al. |
| 2013/0197328 A1 | 8/2013 | Diab et al. |
| 2013/0197364 A1 | 8/2013 | Han |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0261494 A1 | 10/2013 | Bloom et al. |
| 2013/0262730 A1 | 10/2013 | Al-Ali et al. |
| 2013/0267804 A1 | 10/2013 | Al-Ali |
| 2013/0274571 A1 | 10/2013 | Diab et al. |
| 2013/0274572 A1 | 10/2013 | Al-Ali et al. |
| 2013/0279109 A1 | 10/2013 | Lindblad et al. |
| 2013/0296672 A1 | 11/2013 | O'Neil et al. |
| 2013/0296713 A1 | 11/2013 | Al-Ali et al. |
| 2013/0297330 A1 | 11/2013 | Kamen et al. |
| 2013/0317327 A1 | 11/2013 | Al-Ali et al. |
| 2013/0317370 A1 | 11/2013 | Dalvi et al. |
| 2013/0317393 A1 | 11/2013 | Weiss et al. |
| 2013/0324804 A1 | 12/2013 | McKeown et al. |
| 2013/0324808 A1 | 12/2013 | Al-Ali et al. |
| 2013/0324817 A1 | 12/2013 | Diab |
| 2013/0331036 A1 | 12/2013 | Baker et al. |
| 2013/0331660 A1 | 12/2013 | Al-Ali et al. |
| 2013/0331670 A1 | 12/2013 | Kiani |
| 2013/0338461 A1 | 12/2013 | Lamego et al. |
| 2013/0340176 A1 | 12/2013 | Stevens et al. |
| 2013/0345921 A1 | 12/2013 | Al-Ali et al. |
| 2014/0005502 A1 | 1/2014 | Klap et al. |
| 2014/0012100 A1 | 1/2014 | Al-Ali et al. |
| 2014/0022081 A1 | 1/2014 | Ribble et al. |
| 2014/0025010 A1 | 1/2014 | Stroup et al. |
| 2014/0025306 A1 | 1/2014 | Weber et al. |
| 2014/0031650 A1 | 1/2014 | Weber et al. |
| 2014/0034353 A1 | 2/2014 | Al-Ali et al. |
| 2014/0046674 A1 | 2/2014 | Rosenfeld |
| 2014/0051952 A1 | 2/2014 | Reichgott et al. |
| 2014/0051953 A1 | 2/2014 | Lamego et al. |
| 2014/0051954 A1 | 2/2014 | Al-Ali et al. |
| 2014/0058230 A1 | 2/2014 | Abdul-Hafiz et al. |
| 2014/0066783 A1 | 3/2014 | Kiani et al. |
| 2014/0073167 A1 | 3/2014 | Al-Ali et al. |
| 2014/0077956 A1 | 3/2014 | Sampath et al. |
| 2014/0081097 A1 | 3/2014 | Al-Ali et al. |
| 2014/0081099 A1 | 3/2014 | Banet et al. |
| 2014/0081100 A1 | 3/2014 | Muhsin et al. |
| 2014/0081175 A1 | 3/2014 | Telfort |
| 2014/0088385 A1 | 3/2014 | Moon et al. |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0125495 A1 | 5/2014 | Al-Ali |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142399 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0142445 A1 | 5/2014 | Banet et al. |
| 2014/0152673 A1 | 6/2014 | Lynn et al. |
| 2014/0155712 A1 | 6/2014 | Lamego et al. |
| 2014/0163344 A1 | 6/2014 | Al-Ali |
| 2014/0163393 A1 | 6/2014 | McCombie et al. |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0188516 A1 | 7/2014 | Kamen |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0200415 A1 | 7/2014 | McCombie et al. |
| 2014/0200420 A1 | 7/2014 | Al-Ali |
| 2014/0200422 A1 | 7/2014 | Weber et al. |
| 2014/0206963 A1 | 7/2014 | Al-Ali |
| 2014/0213864 A1 | 7/2014 | Abdul-Hafiz et al. |
| 2014/0235964 A1 | 8/2014 | Banet et al. |
| 2014/0243627 A1 | 8/2014 | Diab et al. |
| 2014/0249431 A1 | 9/2014 | Banet et al. |
| 2014/0249432 A1 | 9/2014 | Banet et al. |
| 2014/0249433 A1 | 9/2014 | Banet et al. |
| 2014/0249434 A1 | 9/2014 | Banet et al. |
| 2014/0249435 A1 | 9/2014 | Banet et al. |
| 2014/0249440 A1 | 9/2014 | Banet et al. |
| 2014/0249441 A1 | 9/2014 | Banet et al. |
| 2014/0249442 A1 | 9/2014 | Banet et al. |
| 2014/0257056 A1 | 9/2014 | Moon et al. |

(56) References Cited

U.S. PATENT DOCUMENTS

| | | |
|---|---|---|
| 2014/0257057 A1 | 9/2014 | Reis Cunha et al. |
| 2014/0266787 A1 | 9/2014 | Tran |
| 2014/0266790 A1 | 9/2014 | Al-Ali et al. |
| 2014/0275808 A1 | 9/2014 | Poeze et al. |
| 2014/0275816 A1 | 9/2014 | Sandmore |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0276115 A1 | 9/2014 | Dalvi et al. |
| 2014/0276145 A1 | 9/2014 | Banet et al. |
| 2014/0276175 A1 | 9/2014 | Banet et al. |
| 2014/0288400 A1 | 9/2014 | Diab et al. |
| 2014/0296664 A1 | 10/2014 | Bruinsma et al. |
| 2014/0301893 A1 | 10/2014 | Stroup et al. |
| 2014/0303520 A1 | 10/2014 | Telfort et al. |
| 2014/0309506 A1 | 10/2014 | Lamego et al. |
| 2014/0309559 A1 | 10/2014 | Telfort et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0336517 A1 | 11/2014 | Schnall et al. |
| 2014/0343436 A1 | 11/2014 | Kiani |
| 2014/0343889 A1 | 11/2014 | Ben Shalom et al. |
| 2014/0357966 A1 | 12/2014 | Al-Ali et al. |
| 2014/0371548 A1 | 12/2014 | Al-Ali et al. |
| 2014/0371632 A1 | 12/2014 | Al-Ali et al. |
| 2014/0378784 A1 | 12/2014 | Kiani et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0018650 A1 | 1/2015 | Al-Ali et al. |
| 2015/0025406 A1 | 1/2015 | Al-Ali |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0051462 A1 | 2/2015 | Olsen |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0094618 A1 | 4/2015 | Russell et al. |
| 2015/0097701 A1 | 4/2015 | Muhsin et al. |
| 2015/0099950 A1 | 4/2015 | Al-Ali et al. |
| 2015/0099951 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0133755 A1 | 5/2015 | Smith et al. |
| 2015/0140863 A1 | 5/2015 | Al-Ali et al. |
| 2015/0141781 A1 | 5/2015 | Weber et al. |
| 2015/0164437 A1 | 6/2015 | McCombie et al. |
| 2015/0165312 A1 | 6/2015 | Kiani |
| 2015/0196237 A1 | 7/2015 | Lamego |
| 2015/0196249 A1 | 7/2015 | Brown et al. |
| 2015/0201874 A1 | 7/2015 | Diab |
| 2015/0208966 A1 | 7/2015 | Al-Ali |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0282708 A1 | 10/2015 | Schlottau et al. |
| 2015/0282717 A1 | 10/2015 | McCombie et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366472 A1 | 12/2015 | Kiani |
| 2015/0366507 A1 | 12/2015 | Blank et al. |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0022224 A1 | 1/2016 | Banet et al. |
| 2016/0029932 A1 | 2/2016 | Al-Ali |
| 2016/0029933 A1 | 2/2016 | Al-Ali et al. |
| 2016/0045118 A1 | 2/2016 | Kiani |
| 2016/0045163 A1 | 2/2016 | Weisner et al. |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Al-Ali et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0073967 A1 | 3/2016 | Lamego et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0106366 A1 | 4/2016 | Banet et al. |
| 2016/0113527 A1 | 4/2016 | Al-Ali |
| 2016/0143546 A1 | 5/2016 | McCombie et al. |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0166188 A1 | 6/2016 | Bruinsma et al. |
| 2016/0166210 A1 | 6/2016 | Al-Ali |
| 2016/0183836 A1 | 6/2016 | Muuranto et al. |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0321420 A1 | 11/2016 | Klee et al. |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007190 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0027456 A1 | 2/2017 | Kinast et al. |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali |
| 2017/0055905 A1* | 3/2017 | Cohrs .................. A61B 5/681 |
| 2017/0079594 A1 | 3/2017 | Telfort et al. |
| 2017/0086723 A1 | 3/2017 | Al-Ali et al. |
| 2017/0119252 A1 | 5/2017 | Kim et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |

(56) References Cited

U.S. PATENT DOCUMENTS

| | | |
|---|---|---|
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0202490 A1 | 7/2017 | Al-Ali et al. |
| 2017/0224231 A1 | 8/2017 | Al-Ali |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311891 A1 | 11/2017 | Kiani et al. |
| 2017/0332976 A1 | 11/2017 | Al-Ali |
| 2017/0332980 A1 | 11/2017 | Fifield et al. |
| 2018/0069776 A1 | 3/2018 | Lamego et al. |
| 2018/0097373 A1 | 4/2018 | McSweyn et al. |
| 2018/0103874 A1 | 4/2018 | Lee et al. |
| 2018/0110478 A1 | 4/2018 | Al-Ali |
| 2018/0116575 A1 | 5/2018 | Perea et al. |
| 2018/0130325 A1 | 5/2018 | Kiani et al. |
| 2018/0161499 A1 | 6/2018 | Al-Ali et al. |
| 2018/0174679 A1 | 6/2018 | Sampath et al. |
| 2018/0174680 A1 | 6/2018 | Sampath et al. |
| 2018/0192955 A1 | 7/2018 | Al-Ali et al. |
| 2018/0199871 A1 | 7/2018 | Pauley et al. |
| 2018/0213583 A1 | 7/2018 | Al-Ali |
| 2018/0214031 A1 | 8/2018 | Kiani et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0256113 A1 | 9/2018 | Weber et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2019/0015023 A1 | 1/2019 | Monfre |
| 2019/0021638 A1 | 1/2019 | Al-Ali et al. |
| 2019/0090748 A1 | 3/2019 | Al-Ali |
| 2019/0117070 A1 | 4/2019 | Muhsin et al. |
| 2019/0200941 A1 | 7/2019 | Chandran et al. |
| 2019/0239787 A1 | 8/2019 | Pauley et al. |
| 2019/0320906 A1 | 10/2019 | Olsen |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0021930 A1 | 1/2020 | Iswanto et al. |
| 2020/0060869 A1 | 2/2020 | Telfort et al. |
| 2020/0085321 A1 | 3/2020 | Hatch |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0251501 A1 | 8/2021 | Moon et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0125377 A1 | 4/2022 | Mendes-Roter et al. |
| 2022/0148724 A1 | 5/2022 | Pasternak et al. |
| 2022/0151521 A1 | 5/2022 | Krishnamani et al. |
| 2022/0211323 A1 | 7/2022 | Schnall |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0331065 A1 | 10/2022 | Shah et al. |
| 2022/0346724 A1 | 11/2022 | Ferber et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |

FOREIGN PATENT DOCUMENTS

| | | |
|---|---|---|
| CN | 108370502 | 8/2018 |
| EM | 001198584-0059 | 6/2010 |
| EP | 0735499 | 10/1996 |
| EP | 0 880 936 | 12/1998 |
| EP | 2335569 | 6/2011 |
| EP | 2766834 | 8/2014 |
| EP | 2811894 | 12/2014 |
| EP | 2 901 921 | 8/2015 |
| JP | H08-080288 | 3/1996 |
| JP | H10-336064 | 12/1998 |
| JP | 2002-513602 | 5/2002 |
| JP | 2002-165764 | 6/2002 |

(56) References Cited

FOREIGN PATENT DOCUMENTS

| | | |
|---|---|---|
| JP | 2002-172096 | 6/2002 |
| JP | 2002-542493 | 12/2002 |
| JP | 2004-337605 | 12/2004 |
| JP | 2005-218036 | 8/2005 |
| JP | 2005-295375 | 10/2005 |
| JP | 2007-021213 | 2/2007 |
| JP | 2007-095365 | 4/2007 |
| JP | 2007-174051 | 7/2007 |
| JP | 2008-126017 | 6/2008 |
| JP | 2008-519635 | 6/2008 |
| JP | 2008-541045 | 11/2008 |
| JP | 2009-017959 | 1/2009 |
| JP | 2009-207836 | 9/2009 |
| JP | 2010-503134 | 1/2010 |
| JP | 2010-524510 | 7/2010 |
| JP | 2011-519607 | 7/2011 |
| JP | 2011-152261 | 8/2011 |
| JP | 2014-533997 | 12/2014 |
| JP | 2016-538015 | 12/2016 |
| JP | 2017-506121 | 3/2017 |
| JP | D1605226 | 5/2018 |
| JP | D1614787 | 10/2018 |
| JP | D1665851 | 4/2019 |
| TW | D169966 | 8/2015 |
| TW | D182804 | 5/2017 |
| TW | D126452 | 12/2018 |
| TW | D207721 | 10/2020 |
| WO | WO 98/004182 | 2/1998 |
| WO | WO 98/029790 | 7/1998 |
| WO | WO 99/013766 | 3/1999 |
| WO | WO 99/056613 | 11/1999 |
| WO | WO 00/063713 | 10/2000 |
| WO | WO 00/074551 | 12/2000 |
| WO | WO 01/064101 | 9/2001 |
| WO | WO 2004/056266 | 7/2004 |
| WO | WO 2004/059551 | 7/2004 |
| WO | WO 2006/051461 | 5/2006 |
| WO | WO 2011/001302 | 1/2011 |
| WO | WO 2011/002904 | 1/2011 |
| WO | WO 2011/025549 | 3/2011 |
| WO | WO 2012/112891 | 8/2012 |
| WO | WO 2013/056160 | 4/2013 |
| WO | WO 2013/119982 | 8/2013 |
| WO | WO 2013/184283 | 12/2013 |
| WO | WO 2015/054665 | 4/2015 |
| WO | WO 2017/040700 | 3/2017 |
| WO | WO 2020/077149 | 4/2020 |
| WO | WO 2023/132952 | 7/2023 |

OTHER PUBLICATIONS

US 2022/0192529 A1, 06/2022, Al-Ali et al. (withdrawn)
ADInstruments: "Human NIBP Controller Owner's Guide Human NIBP Owner's Guide", Jan. 1, 2014, XP055673095, Retrieved from the Internet: http://cdn.adinstruments.com/adi-web/manuals/human-nibp-OG.pdf [retrieved on Mar. 3, 2020), p. 16; figures 2-4, pp. 90.
International Preliminary Report on Patentability and Written Opinion received in PCT Application No. PCT/US2019/055722, dated Apr. 22, 2021.
International Preliminary Report on Patentability and Written Opinion received in PCT Application No. PCT/US2021/031625, dated Nov. 24, 2022.
International Search Report and Written Opinion received in PCT Application No. PCT/US2019/055722, dated Mar. 23, 2020.
International Search Report and Written Opinion received in PCT Application No. PCT/US2021/031625, dated Aug. 25, 2021.
International Search Report and Written Opinion received in PCT Application No. PCT/US2022/053988 on Jun. 26, 2023.
Masimo Sleep™, posted at masimopersonalhealth.com, no posting date, retrieved Nov. 17, 2021, online, https://www.masimopersonalhealth.com/pages/masimo-sleep (Year: 2021).
Notice of Allowance received in Taiwan Patent Office Application No. 108302030, dated Aug. 14, 2020 in 6 pages.
Notice of Allowance received in Taiwan Patent Office Application No. 108302035, dated Mar. 13, 2020 in 6 pages.
Notice of Allowance received in Taiwan Patent Office Application No. 108302046, dated Mar. 18, 2020 in 6 pages.
Notice of Allowance received in Taiwan Patent Office Application No. 109301079, dated Jul. 8, 2020 in 6 pages.
Notice of Allowance received in Taiwan Patent Office Application No. 109301080, dated Jul. 7, 2020 in 6 pages.
Notice of Allowance received in Taiwan Patent Office Application No. 109301129, dated Jul. 8, 2020 in 6 pages.
Notice of Allowance received in Taiwan Patent Office Application No. 109301130, dated Jul. 8, 2020 in 6 pages.
Notice of Allowance received in Taiwan Patent Office Application No. 109303055, dated Jan. 21, 2021 in 6 pages.
Notice of Allowance received in Taiwan Patent Office Application No. 109303056, dated Jan. 21, 2021 in 6 pages.
Notice of Allowance received in Taiwan Patent Office Application No. 109303057, dated Jan. 21, 2021 in 6 pages.
Patil et al., "Telemonitoring Physiological Parameters of a Patient from a Distance by Near Field Communication Mobile", 2014 Fourth International Conference on Advanced Computing & Communication Technologies, pp. 345-348.
PCT Invitation to Pay Additional Search Fees issued in application No. PCT/US2019/055722 on Jan. 30, 2020.
PCT Invitation to Pay Additional Search Fees issued in application No. PCT/US2022/053988 on May 4, 2023.
"Radius PPG™ Tetherless Pulse Oximetry", masimo.com, site visited Mar. 18, 2022: https://www.masimo.com/products/sensors/radius-ppg/, pp. 2.
Wayback Machine search for "Masimo Sleep™", first found Sep. 24, 2020, retrieved Nov. 17, 2021, online, https://web.archive.org/web/20200924015943/https://www.masimopersonalhealth.com/pages/masimo-sleep (Year: 2020), pp. 8.
Yongwu, Shi, "Research progress of wearable medical devices", Medical Equipment, Mar. 2018, vol. 31, No. 5, pp. 3.
U.S. Appl. No. 12/973,392, filed Dec. 20, 2010, Kiani et al.
U.S. Appl. No. 29/537,221, filed Aug. 24, 2015, Al-Ali et al.
Aminian et al., "Spatio-Temporal Parameters of Gait Measured by an Ambulatory System Using Miniature Gyroscopes", Journal of Biomechanics, 2002, vol. 35, pp. 689-699.
Anliker et al., "Amon: A Wearable Multiparameter Medical Monitoring and Alert System", IEEE Transactions on Information Technology in Biomedicine, vol. 8, No. 4, Dec. 2004, pp. 415-427.
Asada et al., "Mobile Monitoring with Wearable Photoplethysmographic Biosensors", IEEE Engineering in Medicine and Biology Magazine, May/Jun. 2003, pp. 28-40.
Ayello et al., "How and Why to Do Pressure Ulcer Risk Assessment", Advances in Skin & Wound Care, May/Jun. 2002, vol. 15, No. 3., pp. 125-133.
Bergstrom et al., "A Prospective Study of Pressure Sore Risk Among Institutionalized Elderly", Journal of the American Geriatrics Society, Aug. 1992, vol. 40, No. 8, pp. 747-758.
Bourke et al., "Evaluation of a Threshold-Based Tri-Axial Accelerometer Fall Detection Algoithm", Gait & Posture, vol. 26, 2007, pp. 194-199.
Campo et al., "Wireless Fall Sensor with GPS Location for Monitoring the Elderly", 30th Annual International IEEE EMBS Conference Vancouver, British Columbia, Canada, Aug. 20-24, 2008, pp. 498-501.
Caporusso et al., "A Pervasive Solution for Risk Awareness in the Context of Fall Prevention", Pervasive Health, 2009, pp. 8.
Capuano et at. "Remote Telemetry—New Twists for Old Technology." Nursing Management. vol. 26, No. 7. Jul. 1995.
Chen et al., "In-Bed Fibre Optic Breathing and Movement Sensor for Non-Intrusive Monitoring", Proceedings of SPIE vol. 7173, 2009, pp. 6.
Chen et al., "Wearable Sensors for Reliable Fall Detection", Proceedings of the 2005 IEEE Engineering in Medicine and Biology 27th Annual Conference, Shanghai, China, Sep. 1-4, 2005, pp. 3551-3554.
Degen et al., "Speedy: A Fall Detector in a Wrist Watch", Proceedings of the Seventh IEEE International Symposium on Wearable Computers (ISWC'03), 2003, pp. 184-187.

(56) References Cited

OTHER PUBLICATIONS

Dhillon et al., "Towards the Prevention of Pressure Ulcers with a Wearable Patient Posture Monitor Based on Adaptive Accelerometer Alignment", 34th Annual International Conference of the IEEE EMBS, San Diego, CA, Aug. 28-Sep. 1, 2012, pp. 4513-4516.
Di Rienzo et al., "MagIC System: a New Textile-BasedWearable Device for Biological Signal Monitoring. Applicability in Daily Life and Clinical Setting", Proceedings of the 2005 IEEE Engineering in Medicine and Biology 27th Annual Conference Shanghai, China, Sep. 1-4, 2005, pp. 7167-7169.
Dinh et al, "A Fall and Near-Fall Assessment and Evaluation System", The Open Biomedical Engineering Journal, 2009, vol. 3, pp. 1-7.
Elmer-Dewitt, Philip, Apple's iWatch: The killer apps may be in hospitals, not health clubs, Fortune.com, Feb. 3, 2014, http://fortune.com/2014/02/03/apples-iwatch-the-killer-apps-may-be-in-hospitals-not-health-clubs/, in 4 pages.
Giansanti et al., "Assessment of Fall-Risk by Means of a Neural Network Based on Parameters Assessed by a Wearable Device During Posturography", Medical Engineering & Physics, vol. 30, 2008, pp. 367-372.
Giansanti, Daniele, "Investigation of Fall-Risk Using a Wearable Device with Accelerometers and Rate Gyroscopes", Institute of Physics Publishing, Physiological Measurement, vol. 27, 2006, pp. 1081-1090.
Grundy et al. "Telemedicine in Critical Care: An Experiment in Health Care Delivery." Oct. 1977.
Grundy et al. "Telemedicine in Critical Care: Problems in design, implementation and assessment." vol. 10, No. 7. Jul. 1982.
Gunningberg et al., "Improved Quality and Comprehensiveness in Nursing Documentation of Pressure Ulcers after Implementing an Electronic Health Record in Hospital Care", Journal of Clinical Nursing, 2009, vol. 18, pp. 1557-1564.
Harada et al., "Portable Orientation Estimation Device Based on Accelerometers, Magnetometers and Gyroscope Sensors for Sensor Network", IEEE Conference on Multisensor Fusion and Integration for Intelligent Systems 2003, 2003, pp. 191-196.
Hwang et al., "Development of Novel Algorithm and Real-time Monitoring Ambulatory System Using Bluetooth Module for Fall Detection in the Elderly", Proceedings of the 26th Annual International Conference of the IEEE EMBS, Sep. 1-5, 2004, pp. 2204-2207.
Kärki et al., "Pressure Mapping System for Physiological Measurements", XVIII Imeko World Congress, Metrology for a Sustainable Development, Sep. 17 - 22, 2006, Rio de Janeiro, Brazil, pp. 5.
Li et al., "Accurate, Fast Fall Detection Using Gyroscopes and Accelerometer-Derived Posture Information", Conference Paper, Sixth International Workshop on Wearable and Implantable Body Sensor Networks, BSN 2009, Berkeley, CA, USA, Jun. 3-5, 2009, pp. 6.
Lindemann et al., "Evaluation of a Fall Detector Based on Accelerometers: A Pilot Study", Medical & Biological Engineering & Computing, vol. 43, 2005, pp. 548-551.
Linder-Ganz et al., "Real-Time Continuous Monitoring of Sub-Dermal Tissue Stresses Under the Ischial Tuberosities in Individuals with Spinal Cord Injury", Proceedings of the ASME 2008 Summer Bioengineering Conference (SBC2008), Jun. 25-29, 2008, Marriott Resort, Marco Island, Florida, pp. 2.
Luo et al., "A Dynamic Motion Pattern Analysis Approach to Fall Detection", 2004 IEEE International Workshop on Biomedical Circuits & Systems, Dec. 1-3, 2004, pp. S2.1-5-S2.1-8.
Masimo, "Radius-7—The Power of Masimo's Breakthrough Measurements in a Patient-worn Monitor," 2015, in 2 pages.

Mathie et al., "A System for Monitoring Posture and Physical Activity Using Accelerometers", Engineering in Medicine and Biology Society, 2001. Proceedings of the 23rd Annual International Conference of the IEEE, Oct. 25-28, 2001, pp. 3654-3657.
McInerney, Joan A., "Reducing Hospital-Acquired Pressure Ulcer Prevalence Through a Focused Prevention Program", Advances in Skin & Wound Care, vol. 21, No. 2, Feb. 2008, pp. 75-78.
Merbitz et al., "Wheelchair Push-ups: Measuring Pressure Relief Frequency", Archives of Physical Medicine and Rehabilitation, vol. 66, No. 7, Jul. 1985, pp. 433-438.
Narayanan et al., "Falls Management: Detection and Prevention, Using a Waist-Mounted Triaxial Accelerometer", Proceedings of the 29th Annual International Conference of the IEEE EMBS Cité Internationale, Lyon, France, Aug. 23-26, 2007, pp. 4037-4040.
Noury, Norbert, "A Smart Sensor for the Remote Follow Up of Activity and Fall Detection of the Elderly", 2nd Annual International IEEE-EMBS Special Topic Conference on Microtechnologies in Medicine & Biology, May 2-4, 2002, pp. 314-317.
Nyan et al., "A Wearable System for Pre-Impact Fall Detection", Journal of Biomechanics, vol. 41, 2008, pp. 3475-3481.
Nyan et al., "Garment-Based Detection of Falls and Activities of Daily Living Using 3-Axis MEMS Accelerometer", Institute of Physics Publishing, International MEMS Conference 2006, Journal of Physics: Conference Series 34, 2006, pp. 1059-1067.
O'Donovan et al., "A Context Aware Wireless Body Area Network", Pervasive Health, 2009, pp. 8.
Pérolle et al., "Automatic Fall Detection and Activity Monitoring for Elderly", Jan. 2007, pp. 6.
Philips, "Small, lightweight, and cableless—Philips Mobile CL cuffs, sensors, and accessories" brochure, 2013, in 2 pages.
Po et al., "Overview of MEMSWear II—Incorporating MEMS Technology Into Smart Shirt for Geriatric Care", Institute of Physics Publishing, International MEMS Conference 2006, Journal of Physics: Conference Series 34, 2006, pp. 1079-1085.
Prado et al., "Distributed Intelligent Architecture for Falling Detection and Physical Activity Analysis in the Elderly", Proceedings of the Second Joint EMBS/BMES Conference, Oct. 23-26, 2002, pp. 1910-1911.
Rithalia et al., "Quantification of Pressure Relief Using Interface Pressure and Tissue Perfusion in Alternating Pressure Air Mattresses", Archives of Physical Medicine and Rehabilitation, vol. 81, Oct. 2000, pp. 1364-1369.
Rysavy, "Making the Call with Two-Way Paging", Network Computing, Published Jan. 15, 1997, www.rysavy.com/Articles/twoway.htm.
Sakai et al., "Continuous Monitoring of Interface Pressure Distribution in Intensive Care Patients for Pressure Ulcer Prevention", Journal of Advanced Nursing, vol. 65, No. 4, 2009, pp. 809-817.
Spillman Jr., et al., "A 'Smart' Bed for Non-Intrusive Monitoring of Patient Physiological Factors", Measurement Science and Technology, Aug. 2004, vol. 15, No. 8, pp. 1614-1620.
Wachter, S. Blake; Journal of the American Medical Informatics Association; The Employment of an Iterative Design Process to Develop a Pulmonary Graphical Display; vol. 10, No. 4, Jul./Aug. 2003; pp. 363-372.
Webster, John G., "A Pressure Mat for Preventing Pressure Sores", IEEE Engineering in Medicine & Biology Society 11th Annual International Conference, 1989, pp. 2.
Williams et al., "A Remote Electronic Monitoring System for the Prevention of Pressure Sores", Proceedings of the 19th International Conference, IEEE/EMBS Oct. 30-Nov. 2, 1997, Chicago, IL, pp. 1076-1079.
Wu et al., "Portable Preimpact Fall Detector With Inertial Sensors", IEEE Transactions on Neural Systems and Rehabilitation Engineering, vol. 16, No. 2, Apr. 2008, pp. 178-183.

\* cited by examiner

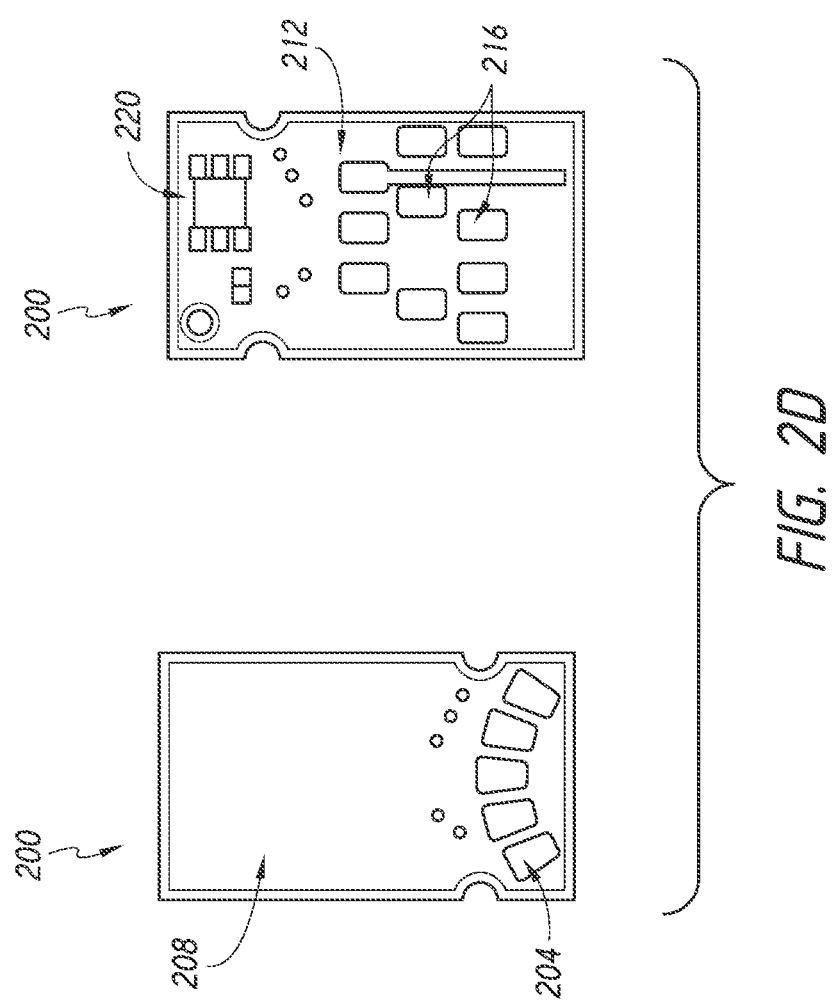

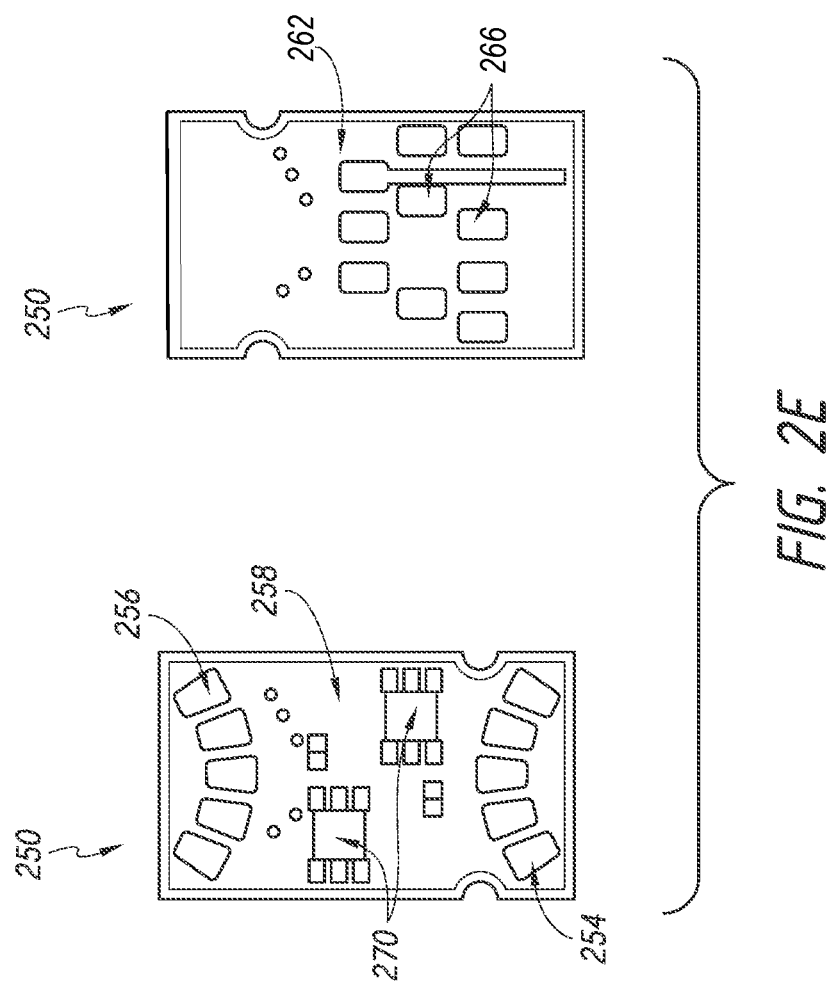

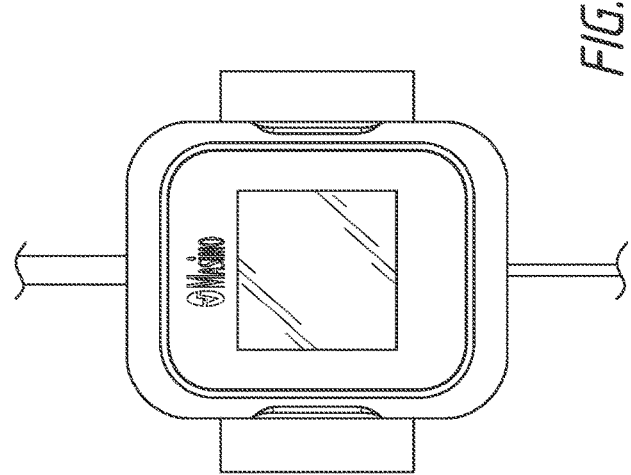
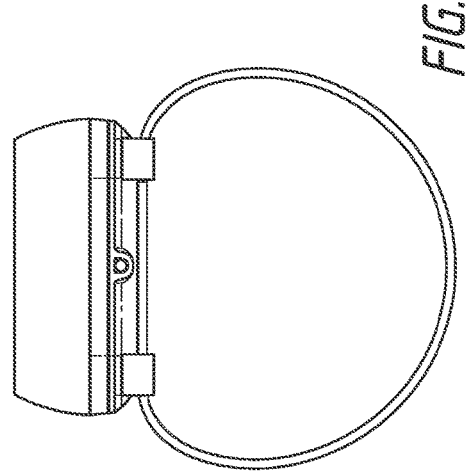
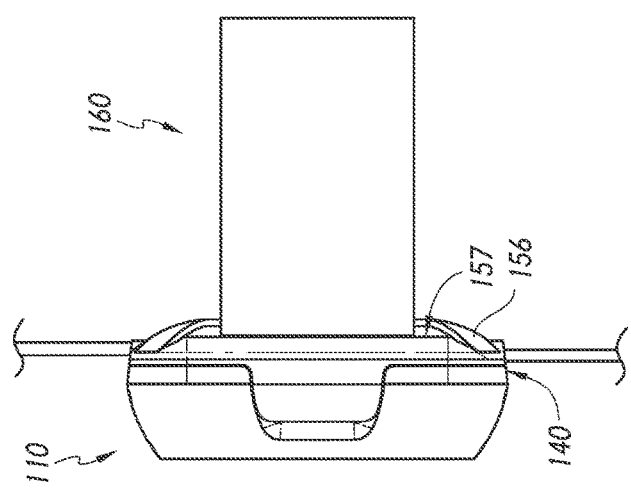
FIG. 3A
FIG. 3B
FIG. 3C

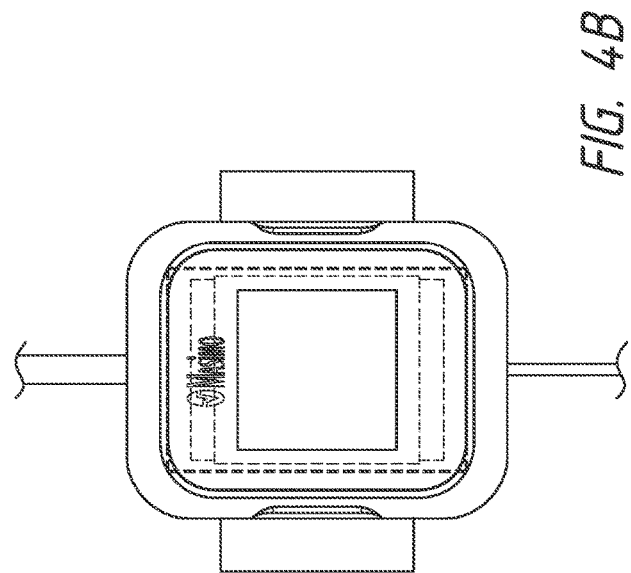
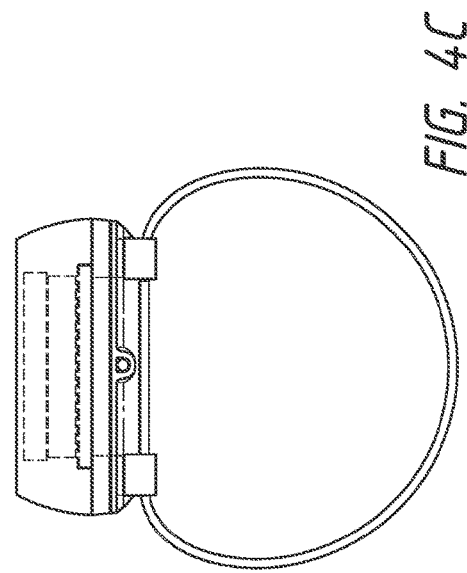
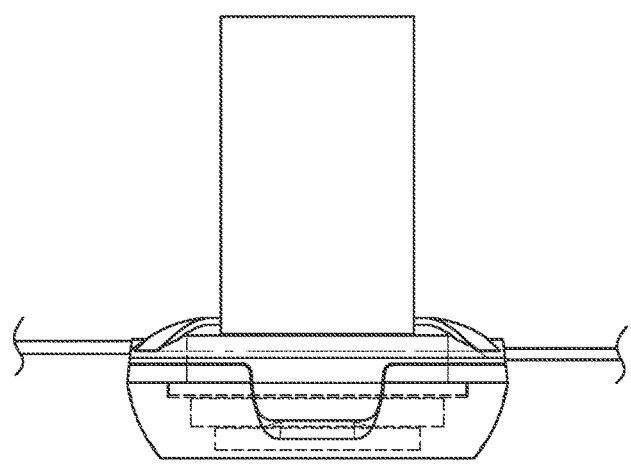

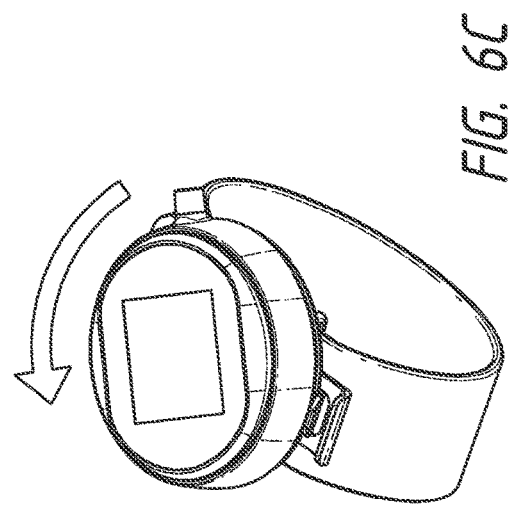
FIG. 6B
FIG. 6C
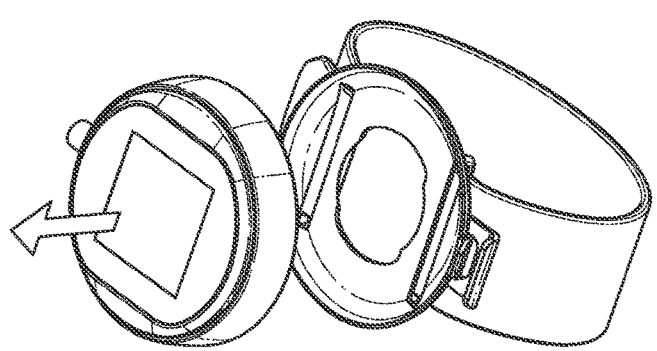
FIG. 6E
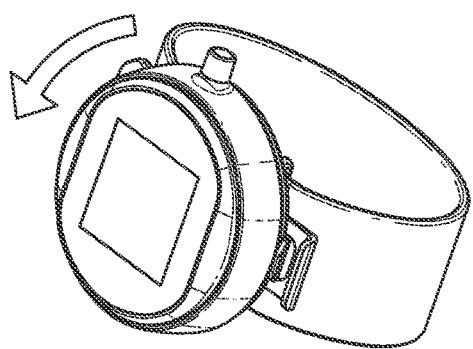
FIG. 6D
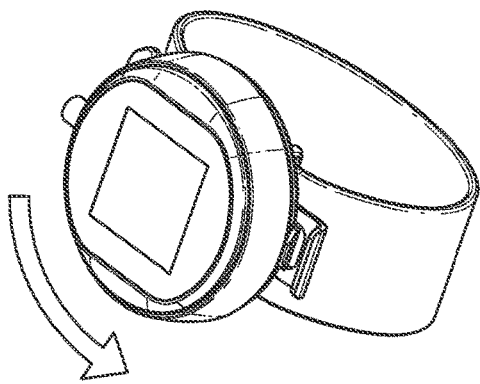

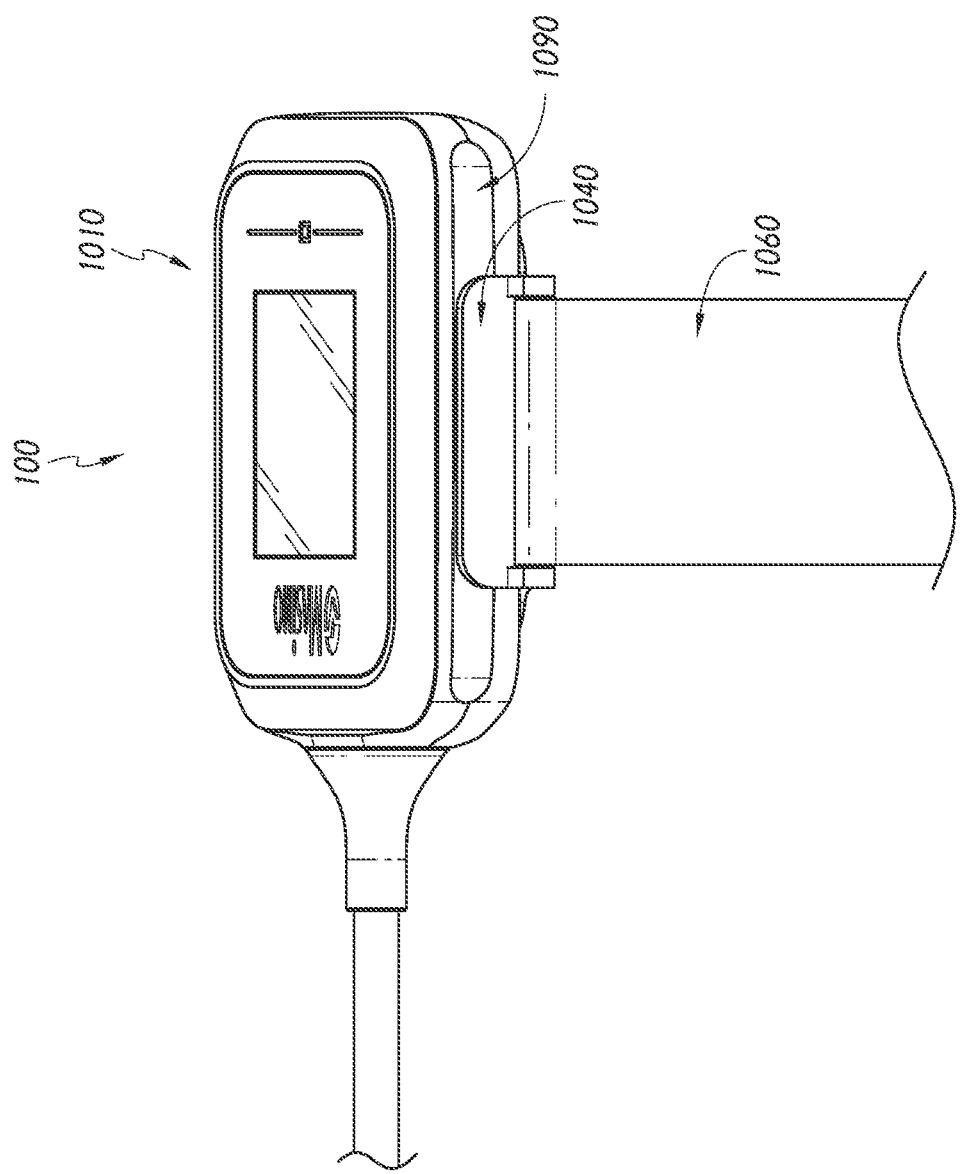

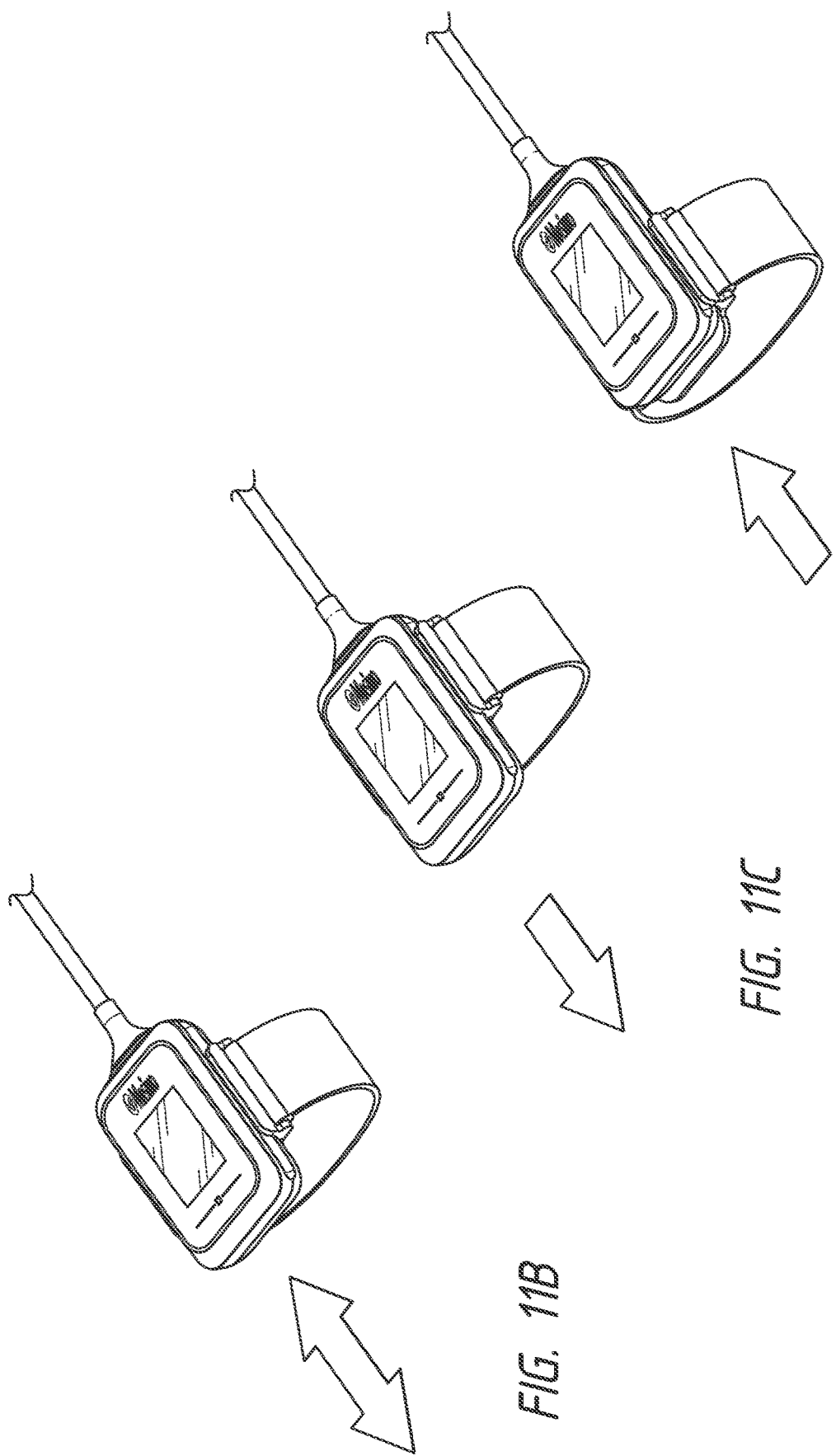

WEARABLE PULSE OXIMETER AND RESPIRATION MONITOR

CROSS-REFERENCE TO RELATED APPLICATIONS

This application is a continuation of U.S. patent application Ser. No. 16/813,551, filed Mar. 9, 2020, titled WEARABLE PULSE OXIMETER AND RESPIRATION MONITOR, which is a continuation of U.S. patent application Ser. No. 15/644,152, filed Jul. 7, 2017, titled WEARABLE PULSE OXIMETER AND RESPIRATION MONITOR, now issued as U.S. Pat. No. 10,617,302, which claims the benefit of U.S. Provisional Application No. 62/359,589, filed Jul. 7, 2016, titled WEARABLE PULSE OXIMETER AND RESPIRATION MONITOR; and U.S. Provisional Application No. 62/463,331, filed Feb. 24, 2017, titled WEARABLE PULSE OXIMETER AND RESPIRATION MONITOR. Each of the foregoing applications is hereby incorporated by reference herein in its entirety.

FIELD OF DISCLOSURE

In general, the present disclosure relates to a wearable patient monitoring device, and methods and apparatuses for monitoring a patient's physiological information using the device. More specifically, the present disclosure relates to the connection of physiological sensors to instruments responsive to signals from the sensors.

BACKGROUND

Hospitals, nursing homes, and other patient care facilities typically include patient monitoring devices at one or more bedsides in the facility. Patient monitoring devices generally include sensors, processing equipment, and displays for obtaining and analyzing a medical patient's physiological parameters such as blood oxygen saturation level, respiratory rate, pulse, and a myriad of other parameters, such as those monitored on commercially available patient monitors from Masimo Corporation of Irvine, California Clinicians, including doctors, nurses, and other medical personnel, use the physiological parameters and trends of those parameters obtained from patient monitors to diagnose illnesses and to prescribe treatments. Clinicians also use the physiological parameters to monitor patients during various clinical situations to determine whether to increase the level of medical care given to patients.

In an embodiment, the patient monitoring devices include a pulse oximeter. Pulse oximetry is a widely accepted noninvasive procedure for measuring the oxygen saturation level of arterial blood, an indicator of a person's oxygen supply. A typical pulse oximetry system utilizes an optical sensor clipped onto a fingertip to measure a relative volume of oxygenated hemoglobin in pulsatile arterial blood flowing within, for example, the fingertip, foot, ear, forehead, or other measurement sites. The oximeter can, in various embodiments, calculate oxygen saturation ($SpO_2$), pulse rate, a plethysmograph waveform, perfusion index (PI), pleth variability index (PVI), methemoglobin (MetHb), carboxyhemoglobin (CoHb), total hemoglobin (tHb), glucose, and/or otherwise, and the oximeter can display on one or more monitors the foregoing parameters individually, in groups, in trends, as combinations, or as an overall wellness or other index. An example of such an oximeter, which can utilize an optical sensor described herein, are described in U.S. application Ser. No. 13/762,270, filed Feb. 7, 2013, titled "Wireless Patient Monitoring Device," U.S. application Ser. No. 14/834,169, filed Aug. 24, 2015, titled "Wireless Patient Monitoring Device," and U.S. application Ser. No. 14/511,974, filed Oct. 10, 2014, titled "Patient Position Detection System," the disclosures of which are hereby incorporated by reference in their entirety.

The patient monitoring devices can also communicate with an acoustic sensor comprising an acoustic transducer, such as a piezoelectric element. The acoustic sensor can detect respiratory and other biological sounds of a patient and provide signals reflecting these sounds to a patient monitor. An example of such an acoustic sensor, which can implement any of the acoustic sensing functions described herein, is described in U.S. application Ser. No. 12/643,939, filed Dec. 21, 2009, titled "Acoustic Sensor Assembly," and in U.S. Application No. 61/313,645, filed Mar. 12, 2010, titled "Acoustic Respiratory Monitoring Sensor Having Multiple Sensing Elements," the disclosures of which are hereby incorporated by reference in their entirety. An example of such an acoustic sensor is also described in U.S. application Ser. Nos. 13/762,270, 14/834,169, and 14/511,974 referenced above.

SUMMARY OF THE DISCLOSURE

In the present disclosure, one or more sensors can be connected to a wireless monitor configured to receive the sensor data, process the data to determine any number of a myriad of physiological parameters, and wirelessly transmit the sensor data or the physiological parameters responsive to the sensor data to a bedside monitor. The bedside monitor can be configured to output the physiological parameters, communication channel, and/or communication status. An example of methods and apparatuses for wirelessly monitoring a patient's physiological information is described in U.S. application Ser. Nos. 13/762,270, 14/834,169, and 14/511,974 referenced above.

Durable and disposable sensors are often used for the patient monitoring devices. These sensors can have connectors which allow detachment from a monitor instrument or a cable. One example of the connectors can include the use of pogo pins on a pin end and a plurality of electrical contacts on a surface of a sensor end. The pin end can have a plurality of retractable electrical connectors or pogo pins extending through pin holes on a printed circuit board. The plurality of electrical contacts on the sensor end are configured to engage contact tips of the plurality of pogo pins when the pin end comes into close proximity with the sensor end. An example of the pogo pin connectors is described in U.S. application Ser. No. 15/017,349, filed Feb. 5, 2016, titled "Pogo Pin Connector," which is expressly bodily incorporated in its entirety and is part of this disclosure.

One aspect of the disclosure is a wireless patient monitoring device for measuring one or more parameters that can be secured to a wrist of the patient. The wireless patient monitoring device can include a monitor instrument, a base, and a strap. The monitor instrument can removably mechanically and electrically engage the base. In some embodiments, the monitor instrument can have a display screen. The base can have a strap connector for engaging a strap that can be worn on the patient's wrist. The base can have an outlet on a first end configured to be connected to a first sensor. In some embodiments, the base can also have an outlet on a second end configured to be connected to a second sensor. The first end can be opposite the second end along a length of the base. The base can have a plurality of electrical contacts on an anterior surface. The plurality of electrical contacts can be configured to contact a plurality of pogo pins extending from a posterior surface of the monitor instrument. The contact between the electrical contacts and the pogo pins can electrically connect the monitor instrument to the sensors that are coupled to the base. The monitor instrument can then receive data from one or both sensors, it can process the data to determine responsive parameters/measurements and/or can transmit the data and calculated parameter information wirelessly to a bedside monitor. In some embodiments, one of the sensors is configured to be connected to the base and can comprise a noninvasive optical sensor of the type used in pulse oximetry. In some embodiments, one of the sensors is configured to be connected to the base and can comprise a non-invasive acoustic sensor of the type used in breath sounds monitoring to determine respiration rate and/or cardiac parameters.

A patient monitoring device configured to be removably secured to a patient and responsive to one or more physiological parameters of the patient can comprise a reusable monitor instrument configured to transmit wireless information to a remote patient monitor and having a plurality of electrical connectors extending from a surface of the monitor instrument; and a disposable portion including (a) at least one non-invasive physiological sensor comprising one of an optical sensor and an acoustic sensor, (b) a base having (i) an electrical connector configured to connect to the at least one physiological sensor, the at least one physiological sensor including its own sensor attachment mechanism separate from the disposable portion, said sensor attachment mechanism configured to removably secure said at least one physiological sensor to a measurement site on said patient, and (ii) a plurality of electrical contacts on a surface, the electrical connector including electronics operably connecting the at least one physiological sensor to the plurality of electrical contacts, the monitor instrument configured to removably mechanically engage the base, the electrical connectors configured to electrically contact the electrical contacts, and (c) an attachment mechanism configured for removably securing the base to the patient, wherein the monitor instrument can be responsive to signals from the at least one physiological sensor, said signals responsive to physiological parameters of the patient. The base can further comprise a second electrical connector configured to connect to a second non-invasive physiological sensor. The physiological sensor can comprise the optical sensor. The physiological sensor can comprise the acoustic sensor. The monitor instrument can comprise a display screen. The plurality of electrical connectors can comprise pogo pins. The device can further comprise one or more cable management mechanisms on the reusable monitor instrument or the base, the one or more cable management mechanisms configured to secure sensor cables.

A patient monitoring device configured to be removably secured to a patient and responsive to one or more physiological parameters of the patient can comprise a reusable monitor instrument configured to transmit wireless information to a remote patient monitor and having a plurality of electrical connectors extending from a surface of the monitor instrument; and a disposable portion including (a) at least two non-invasive physiological sensors, each sensor including a sensor positioner configured to position the sensor with respect to a measurement site on said patient, (b) a base having (i) at least first and second electrical connectors configured to connect to the at least two physiological sensors respectively, and (ii) a plurality of electrical contacts on a surface, the electrical connectors including electronics operably connecting the at least two physiological sensors to the plurality of electrical contacts, the monitor instrument configured to removably mechanically engage the base, the electrical connectors configured to electrically contact the electrical contacts, and (c) an attachment mechanism configured for removably securing the base to the patient, wherein the monitor instrument can be responsive to signals from the at least two physiological sensors, said signals responsive to physiological parameters of the patient. The attachment member can comprise a band configured to be removably secured onto the patient's arm, wrist, leg, or ankle. The attachment member can comprise a cord configured to be worn around the patient's neck. The at least first and second electrical connectors can be positioned on the same side of the base. At least first and second electrical connectors can be configured to removably connect the at least two physiological sensors such that the at least first and second electrical connectors can be exchanged. The plurality of electrical connectors can comprise pogo pins. The device can further comprise one or more cable management mechanisms on the reusable monitor instrument or the base, the one or more cable management mechanisms configured to secure sensor cables.

A patient monitoring device configured to be removably secured to a patient and responsive to one or more physiological parameters of the patient can comprise a reusable monitor instrument configured to transmit wireless information to a remote patient monitor and having at least one electrical connector extending from a surface of the monitor instrument, the at least one electrical connector including electronics configured for operably connecting to at least one physiological sensor; and a disposable portion including a base and an attachment mechanism configured for removably securing the base to the patient, the monitor instrument configured to removably mechanically engage the base, wherein the monitor instrument can be responsive to signals from the at least one physiological sensor, said signals responsive to physiological parameters of the patient. The attachment member can comprise a band configured to be removably secured onto the patient's arm, wrist, leg, or ankle. The attachment member can comprise a cord configured to be worn around the patient's neck. The device can further comprise one or more cable management mechanisms on the reusable monitor instrument or the base, the one or more cable management mechanisms configured to secure sensor cables.

BRIEF DESCRIPTION OF THE DRAWINGS

Various embodiments will be described hereinafter with reference to the accompanying drawings. These embodiments are illustrated and described by example only, and are not intended to limit the scope of the disclosure. In the drawings, similar elements have similar reference numerals.

FIGS. 1G-1I various perspective views of illustrate an embodiment of a wireless patient monitoring device connected to two physiological sensors.

FIGS. 2D-E illustrates front and back views of embodiments of pads or printed circuit boards ("PCBs") having a plurality of electrical contacts for use in an embodiment of the wireless patient monitoring device.

FIGS. 3A-C illustrate left, front and bottom views of an embodiment of the wireless patient monitoring device.

FIGS. 4A-C illustrate left, front and bottom views of the embodiment of the wireless patient monitoring device of FIGS. 3A-C with internal structures shown in broken lines.

FIGS. 6B-E illustrate steps for disassembling a monitor instrument from a base of the embodiment of the wireless patient monitoring device of FIGS. 5A-D.

DETAILED DESCRIPTION

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below.

In clinical settings, medical sensors are often attached to patients to monitor physiological parameters of the patients. Some examples of medical sensors include, but are not limited to, blood oxygen sensors, such as pulse oximetry sensors, acoustic respiratory sensors, EEGs, ECGs, blood pressure sensors, sedation state sensors, etc. Typically, each sensor attached to a patient is connected to a bedside monitoring device with a cable. The cables limit the patient's freedom of movement and impede a care provider's access to the patient. The cables connecting the patient to the bedside monitoring device also make it more difficult to move the patient from room to room or switch to different bedside monitors.

Figure 1A:
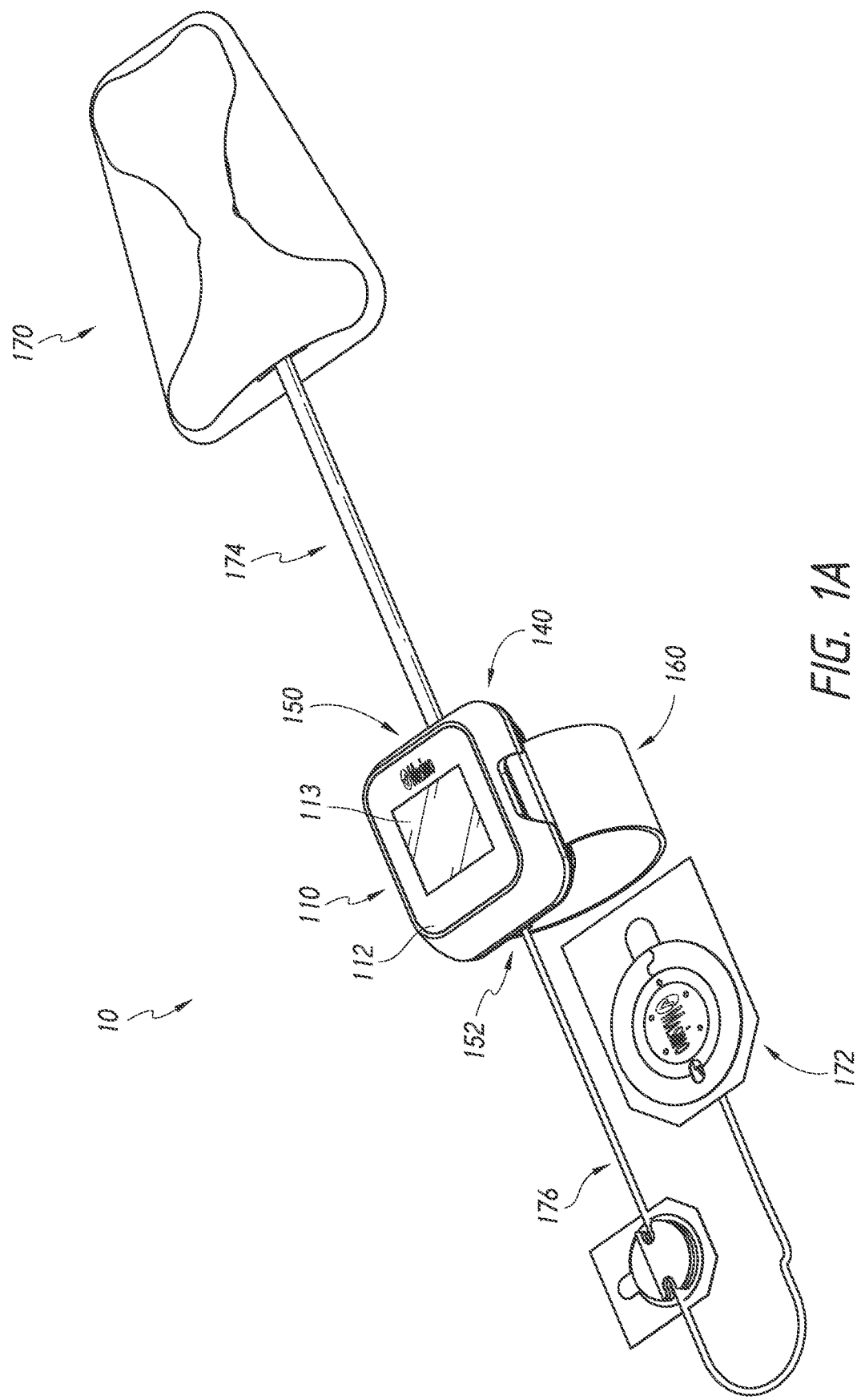
FIGS. 1A-C illustrate perspective and front views of an embodiment of a wireless patient monitoring device connected to two physiological sensors.
Figure 1B:
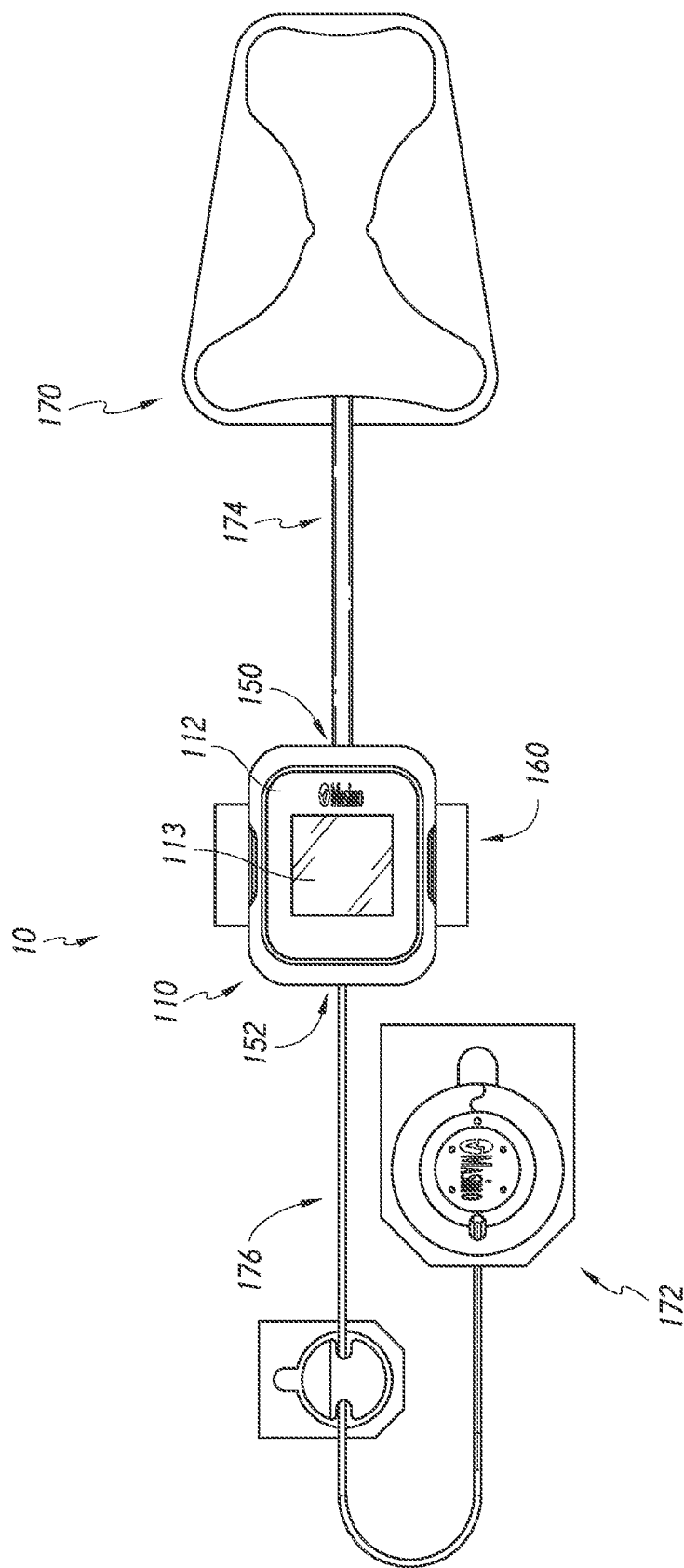

This disclosure describes embodiments of wireless patient monitoring devices that are coupled to one or more sensors and worn by a patient. FIGS. 1A-B illustrate an embodiment of the wireless patient monitoring device 10. The wireless patient monitoring device 10 can have a monitor instrument 110, a base 140, and a strap 160. The monitor instrument 110 can be reusable. The base 140 and/or the strap 160 can be disposable.

The monitor instrument 110 can include a wireless transceiver capable of transmitting data using any of a variety of wireless technologies, such as Wi-Fi (802.11x), Bluetooth (802.15.2), Zigbee (802.15.4), cellular telephony, infrared, RFID, satellite transmission, proprietary protocols, combinations of the same, and the like. The monitor instrument 110 can also include processing capabilities. The monitor instrument 110 can include a hardware processor. The monitor instrument can include a printed circuit board (PCB). In some embodiments, the monitor instrument 100 can have a battery. In some embodiments, the battery can be built inside the monitor instrument 110 and rechargeable. For example, the battery can be recharged when the monitor instrument 100 is placed on a charging dock. In other embodiments, the battery can be replaceable. The monitor instrument 100 can transmit sensor data obtained from sensors to a remote patient monitor (not shown). For example, the remote patient monitor can be a bedside monitor. By transmitting the sensor data wirelessly, the patient monitoring device 10 can advantageously replace some or all cables that connect patients to the bedside monitor. Detailed methods and apparatuses of wirelessly transmitting sensor data to bedside monitoring devices are described in U.S. application Ser. Nos. 13/762,270, 14/834,169, and 14/511,974 referenced above.

An artisan will recognize from the disclosure herein that the device 10 can include additional and/or alternative features and functions. For example, the device 10 can advantageously upload its data to a cloud-based computing platform or data storage platform where the device manufacturer can manage the data, a caregiver, caregiver facility or insurance provider can access the data, or the like. Also, while shown as a device for attachment to the wrist or appendages of non-infants, the device can attach to an ankle of an infant or neonate where the optical sensor is attached to the foot. Other embodiments can use an ear or nose optical sensor, or can combine a nose optical sensor and an acoustic sensor. Still additional embodiments can secure to the head or other site on the body, can include position sensors, fall detection algorithms, patient turn protocols and algorithms or the like.

Figure 2A:
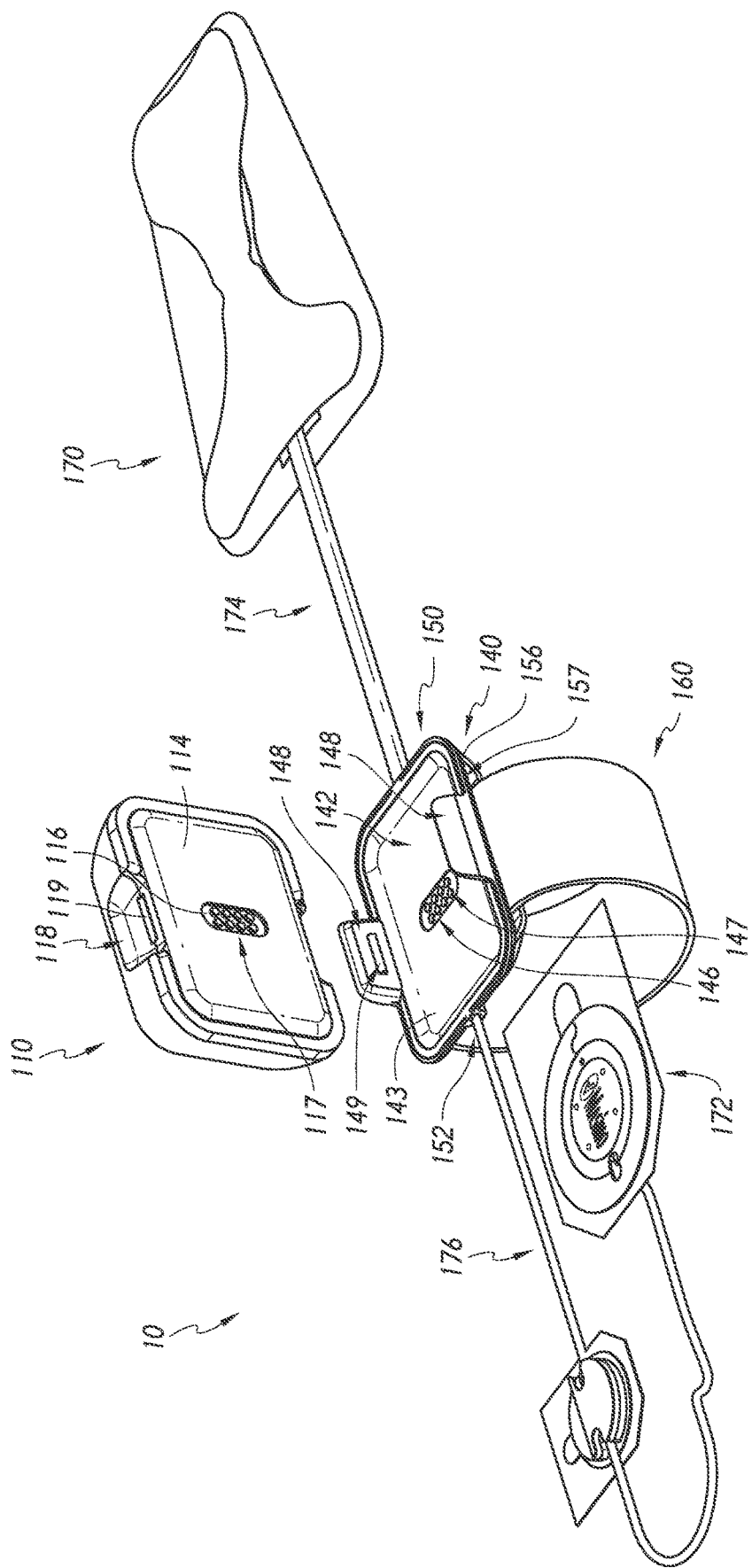
FIGS. 2A-C illustrate partially exploded views of the embodiment of the wireless patient monitoring device of FIGS. 1A-B connected to two physiological sensors.
Figure 2B:
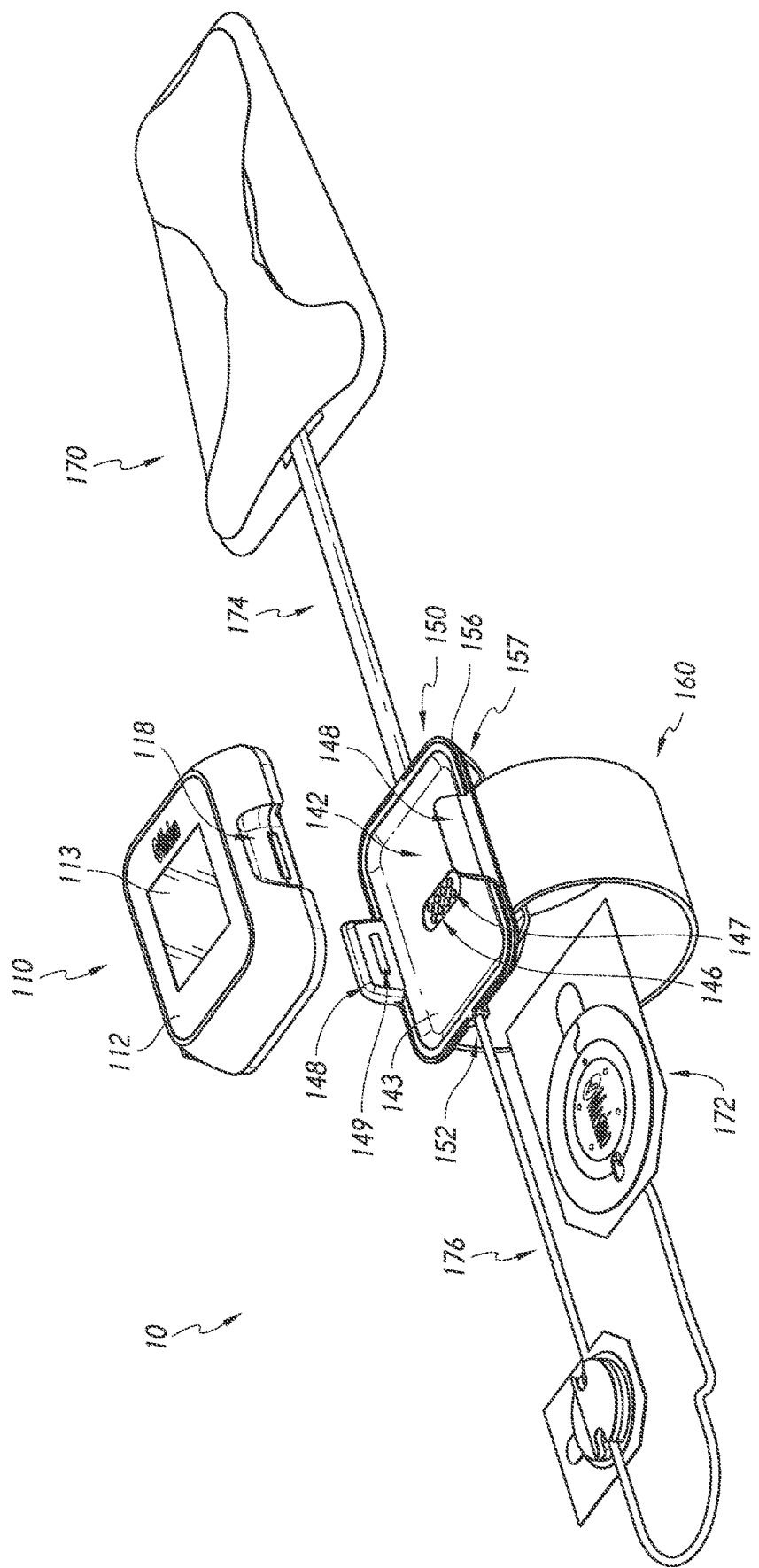
Figure 2C:
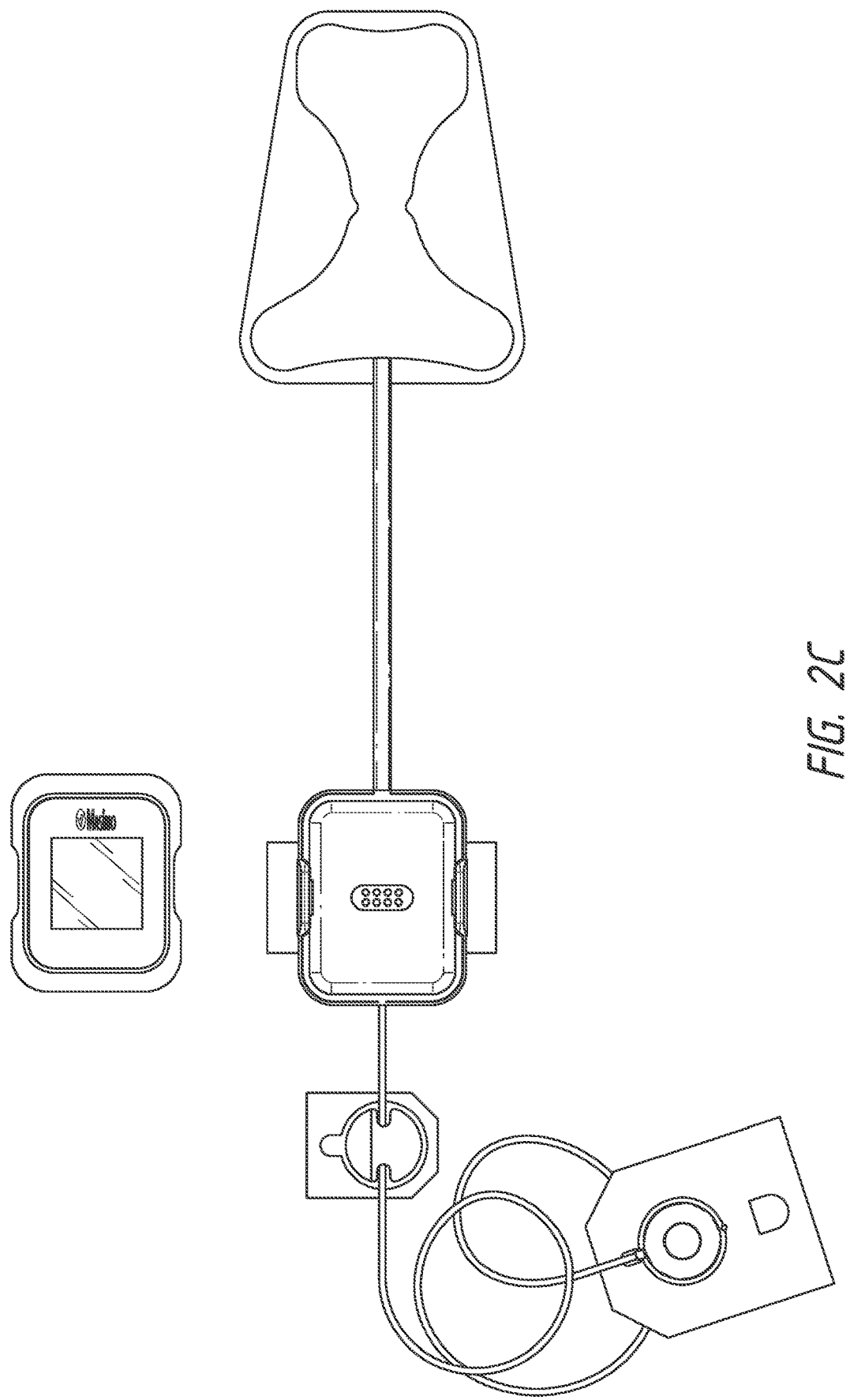

As shown in FIGS. 2A-B, the monitor instrument 110 can be detachable from the base 140. The monitor instrument 110 can have a substantially rectangular shape with an anterior surface 112 and a posterior surface 114. The anterior surface 112 faces away from the base 140. The posterior surface 114 faces toward the base 140. In some embodiments, the monitor instrument 110 can have a length of about 50-70 cm. In some embodiments, the monitor instrument 110 can have a width of about 40-60 cm. The anterior and posterior surfaces 112, 114 can be substantially flat and have a small thickness between the anterior and posterior surfaces 112, 114. The shape, size, and/or weight of the monitor instrument 110 can advantageously resemble a shape size, and/or weight of a watch and be suitable for being worn on the wrist of the patient. The shape size, and/or weight of the monitor instrument 110 are not limiting; however, in an embodiment, the size and weight are approximate that of a wrist watch. For example and not by way of limitation, the monitor instrument can have a circular outer shape as shown in FIGS. 5A-D, or a square outer shape as shown in FIG. 5F. In the illustrated embodiments, the anterior surface 112 can have a display screen 113 for displaying messages and/or physiological parameters for the patient and/or care providers.

As shown in FIG. 2A, the posterior surface 114 of the monitor instrument 110 can include a cover 116 having a group of pogo pin holes. One end of a plurality of pogo pins 117 can protrude from the pogo pin holes of the cover 116. Another end of the pogo pins can form an electrical connection with the PCB inside the monitor instrument 110 to establish an electrical connection between the PCB inside the monitor instrument 110 and one or more sensors, which will be described in more details below. More details of the pogo pins are described in U.S. application Ser. No. 15/017,349 referenced above. In the illustrated embodiment, the plurality of pogo pins 117 is arranged in two rows. A person of ordinary skill in the art will appreciate from the disclosure herein that the configuration of the plurality of pogo pins is not limiting. Additionally, although FIG. 2A shows one cover 116 with a plurality of pogo pins 117 in a center of the posterior surface 114, the number and/or locations of covers with a plurality of pogo pins are not limiting. For example and not by way of limitation, the posterior surface 114 of the monitor instrument 110 can have two covers with pogo pins on opposite ends of the posterior surface 114 along its length or width. In another example, the posterior surface 114 of the monitor instrument 110 can have one cover with pogo pins on each of four corners of the substantially rectangular posterior surface 114.

With continued reference to FIGS. 2A-2B, the base 140 can be made from disposable material(s). Disposability advantageously provides a more sterile environment for patients. That is, in an embodiment, the portions of the device that can come in contact with a patient, such as sensors 170, 172, the strap 160, and the base 140, can be single use items, while the relatively expensive processing components of the monitor instrument 110 can be sanitized, sterilized or the like, and reused. For example and not by way of limitation, the base 140 can be made from plastic materials. The base 140 can have an outer shape corresponding to the outer shape of the monitor instrument 110. As shown in FIGS. 2A-B, the base 140 has a substantially rectangular shape with an anterior surface 142 and a posterior surface 144 (shown in FIG. 2F). The anterior surface 142 faces toward the monitor instrument 110. The posterior surface 144 faces away from the monitor instrument 110 and toward the patient wearing the device. The anterior 142 and posterior 144 surfaces can be substantially flat and have a small thickness between the anterior 142 and posterior 144 surfaces. The shape and size of the base 140 are not limiting. The anterior surface 142 of the base 140 can have a recessed flat surface 143 configured to accommodate the posterior surface 114 of the monitor instrument 110. As shown in FIGS. 1A-B and 2A-B, the monitor instrument 110 can removably engage the anterior surface 142 of the base 140. In the illustrated embodiment, the base 140 can have two tabs 148 configured to clip onto or otherwise mechanically and removably mate with two recesses 118 on the monitor instrument 110. The tab 148 can have a protrusion 149 configured to fit into an indent 119 on the recess 118 of the monitor instrument 110. Other methods of removably coupling the monitor instrument 110 and the base 140 can include a magnet, a clip, a band, a snap fit, a friction fit, twist and secure, slide and secure, or otherwise, and are not limiting.

Figure 1C:
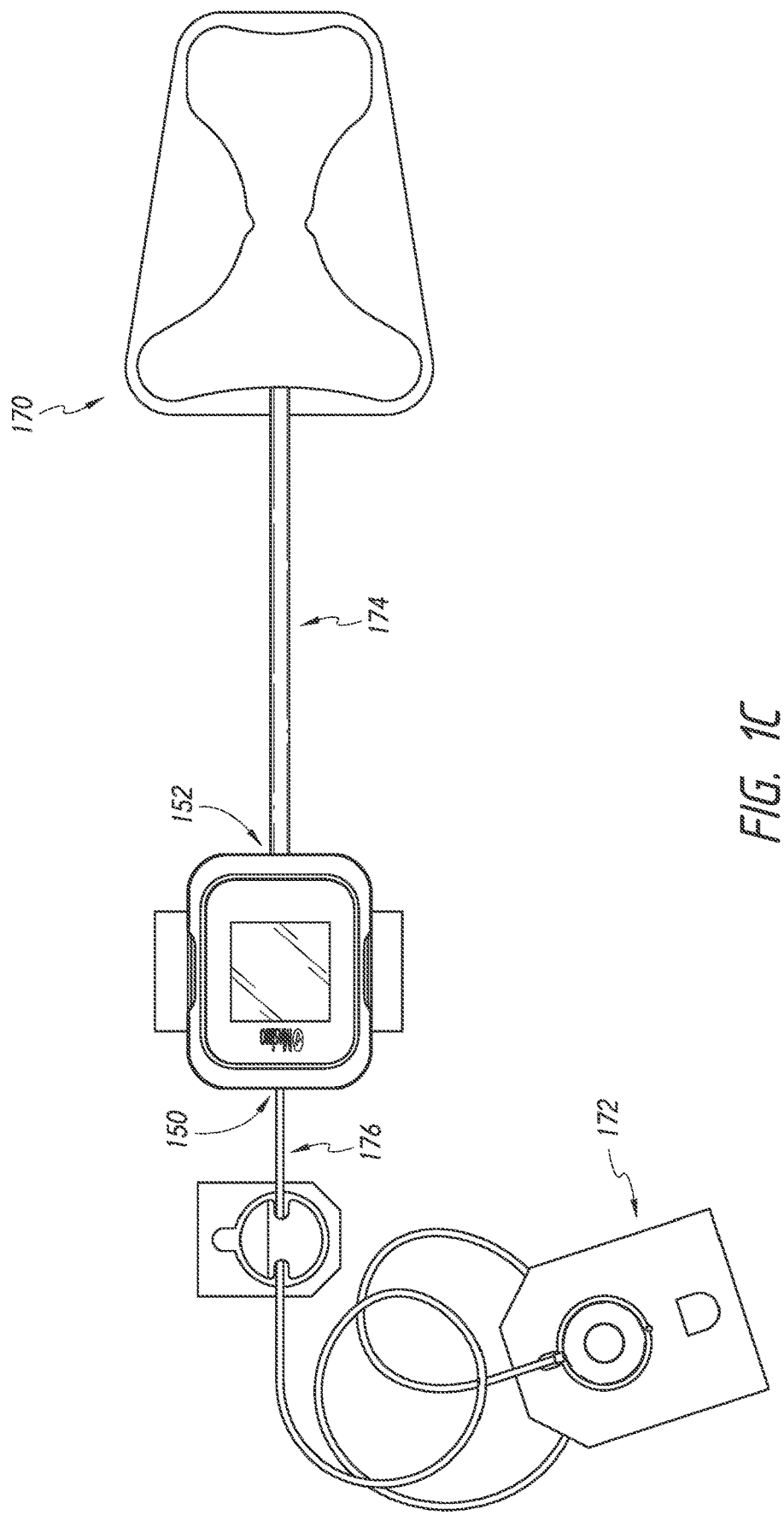

The base 140 can include one or more outlets for accommodating one or more sensor cables extending out of and away from the base 140. As shown in FIGS. 1A-C and 2A-B, the base 140 can include a first outlet 150 on a first end of the base 140 and a second outlet 152 on a second end of the base 140. In the illustrated embodiment, the second end can be opposite the first end along a length of the base 140. A first cable 174 of first sensor 170 can extend away from the base 140 via the first outlet 150. A second cable 176 of a second sensor 172 can extend away from the base 140 via the second outlet 152. Disposing outlets on opposite ends of the base 140 can advantageously prevent cluttering and tangling of the sensor cables. In the illustrated embodiment, the first sensor 170 can comprise an SpO$_2$ sensor and the second sensor 172 can comprise a respiratory rate sensor. Types of sensor that can connect to the base 140 are not limiting. In some embodiments, the base 140 can include only one outlet configured for any type of physiological sensor. In some embodiments, the cable(s) of the one or two sensors can be permanently connected to the outlets of the base. The base and the sensors can be both disposable. As shown in FIGS. 1B and 1C, locations of the first and second sensors 170, 172 can be exchangeable so that the first sensor 170 is connected from the side of the second outlet 152 and the second sensor 172 is connected from the side of the first outlet 150.

FIGS. 1D-1I illustrate embodiments of the wireless patient monitoring device 10 having the first and second outlets 150, 152 on the same end of the base 140. Some or all of remaining features of the wireless patient monitoring device 10 in FIG. 1D-1I can have the same structural details as the wireless patient monitoring device described above. In addition, features of the patient monitoring device 10 in FIGS. 1D-1I can be incorporated into features of patient monitoring device illustrated in the subsequent figures and described below and features of the patient monitoring device illustrated in the subsequent figures and described below can be incorporated into features of patient monitoring device 10 as illustrated in FIGS. 1D-1I. In these embodiments, the first and second cables 174, 176 of the first and second sensors 170, 172, respectively, can extend from the first and second outlets, 150, 152 on the same end of the base 140. As shown in FIGS. 1D-1I, the first cable 174 can be positioned approximately 180° relative to a direction the outlet 150 faces so that when the device 10 is worn by the user, the first and second sensors 170, 172 can be located on opposite ends of the base 140. A skilled artisan will recognize that either one of the first and second cables 174, 176 can be positioned approximately 180° relative to a direction that the outlets 150, 152 face to make the first and second sensors 170, 172 on the opposite ends of the base 140. A skilled artisan will also recognize that either one or both of the first and second cables 174, 176 can be positioned in a direction about 90°, about 180°, or about 270°, or any other angles, relative to a direction that the outlets 150, 152 face, depending on the desired locations of the sensors. A skilled artisan will appreciate from the disclosure herein that one or more outlets can be positioned anywhere along a perimeter of the wireless patient monitoring device, or on any surface of the wireless patient monitoring device, or on any surface or sides of the base 140. If two or more outlets are positioned on one side or surface of the patient monitoring device 10 or base 140, the two or more outlets can be spread out based on, for example, desired positioning of the sensors. In some embodiments, the base 140 and the one or more sensors can be unitary such that the base and the one or more sensors can be a single disposable part.

Figure 12:
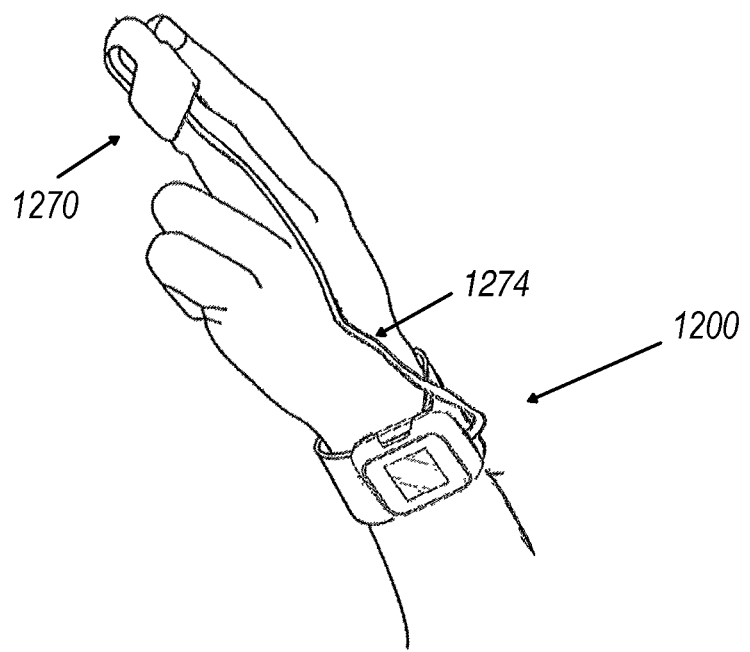
FIG. 12 illustrates a patient wearing an example wireless patient monitoring device.
Figure 13:
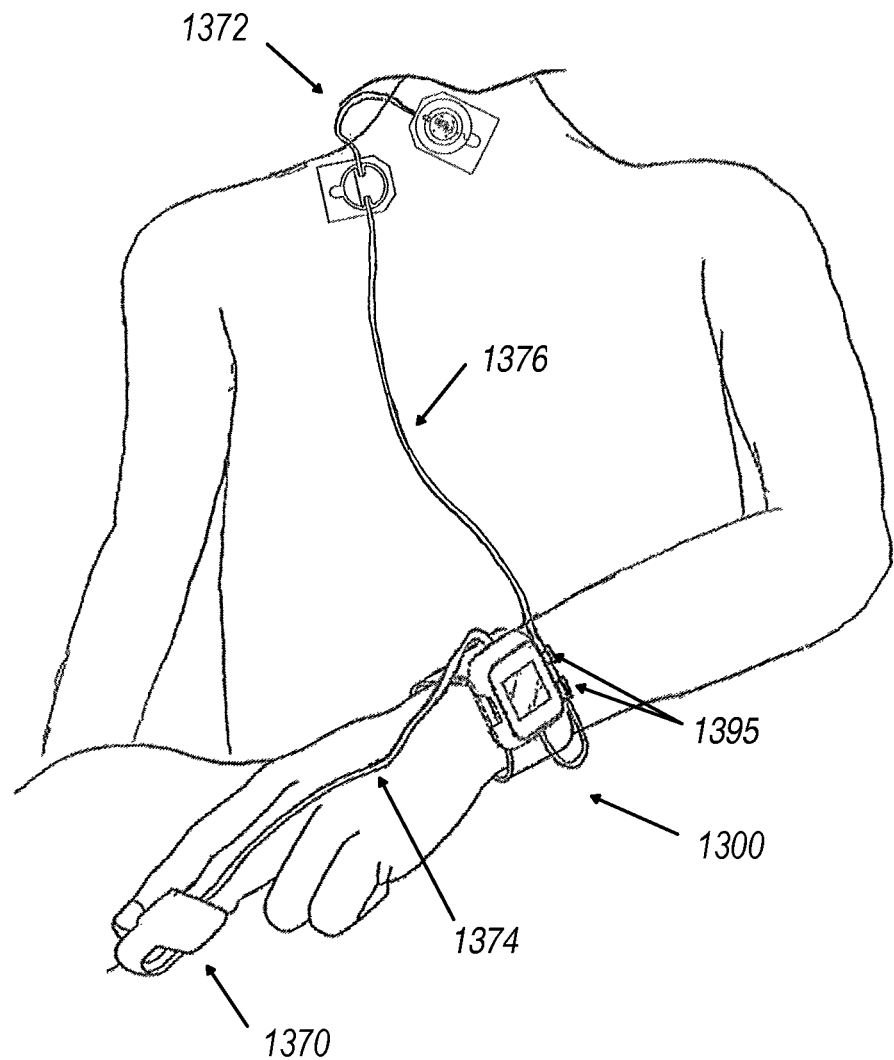
FIG. 13 illustrates a patient wearing an example wireless patient monitoring device.

To maintain the first sensor 170 on the opposite side of the base 140 from the second sensor 172, a cable management system, for example, a cord snapping feature 195 can be used to retain the cable 174 after it is positioned approximately 180° relative to the direction the outlet 150 faces. In the illustrated embodiment, the cable management system 195 can retain a portion of the first cable 174 by a snap fit, although methods of retaining the cable are not limiting. In addition to maintaining the position of the first sensor 170, the cable management system 195 can allow a length of the first cable 174 relative to the base 140 to be adjusted to prevent the first cable 174 from dangling about the patient's wrist or arm. A skilled artisan will recognize from the disclosure herein a wide range of mechanical mating or other mechanisms for positioning and managing the positions of the cables. FIG. 12 illustrates a patient wearing an example wireless patient monitoring device 1200 on the patient's wrist. In the illustrated embodiment, the device 1200 is connected to one sensor 1270. The sensor 1270 can be a pulse oximeter sensor and the patient can wear the sensor 1270 on the patient's fingertip, with the sensor cable or flex-circuit 1274 extending between the device 1200 and the sensor 1270. The device 1200 can include a cable management system described herein to retain a portion of the cable or flex-circuit 1274 and allow a length of the cable or flex-circuit 1274 to be adjustable. FIG. 13 illustrates a patient wearing an example wireless patient monitoring device 1300 on the patient's wrist. In the illustrated embodiment, the device 1300 is connected to a first sensor 1370 and a second sensor 1372. The first sensor 1370 can be a pulse oximeter sensor and the patient can wear the first sensor 1370 on the patient's fingertip. The second sensor 1372 can be an acoustic sensor and the patient can wear the second sensor 1372 near or around the patient's neck. As shown in FIG. 13, a cable management system 1395 can retain a portion of the sensor cable 1376 connecting the second sensor 1372 and the device 1300 and allow a length of the cable 1376 to be adjustable. The device 1300 can further include a cable management system described herein to retain a portion of the cable or flex-circuit 1374 connecting the first sensor 1370 and the device 1300, and allow a length of the cable or flex-circuit 1374 to be adjustable.

Figure 1D:
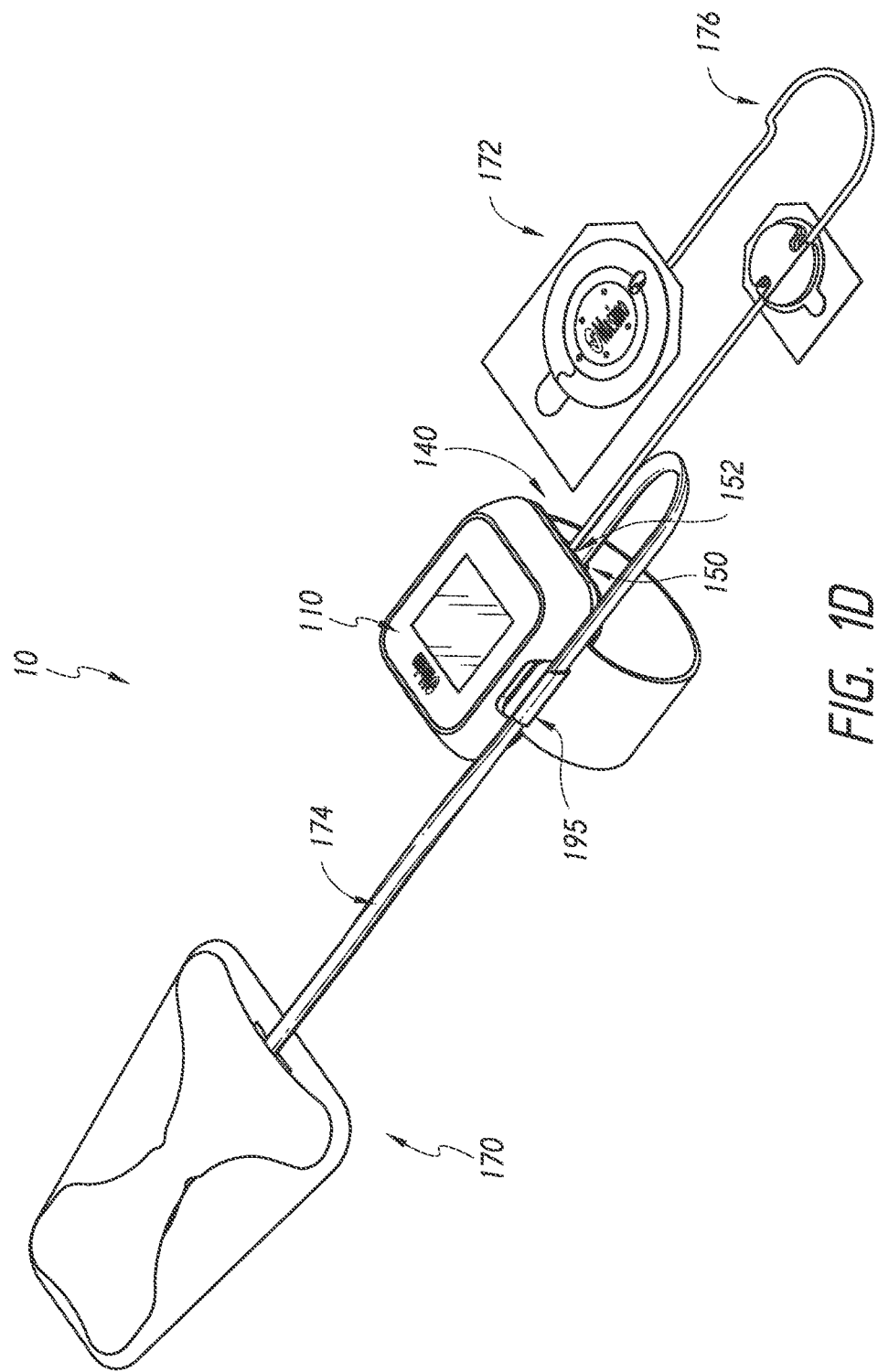
FIGS. 1D-1F illustrate various perspective views of an embodiment of a wireless patient monitoring device connected to two physiological sensors.
Figure 1E:
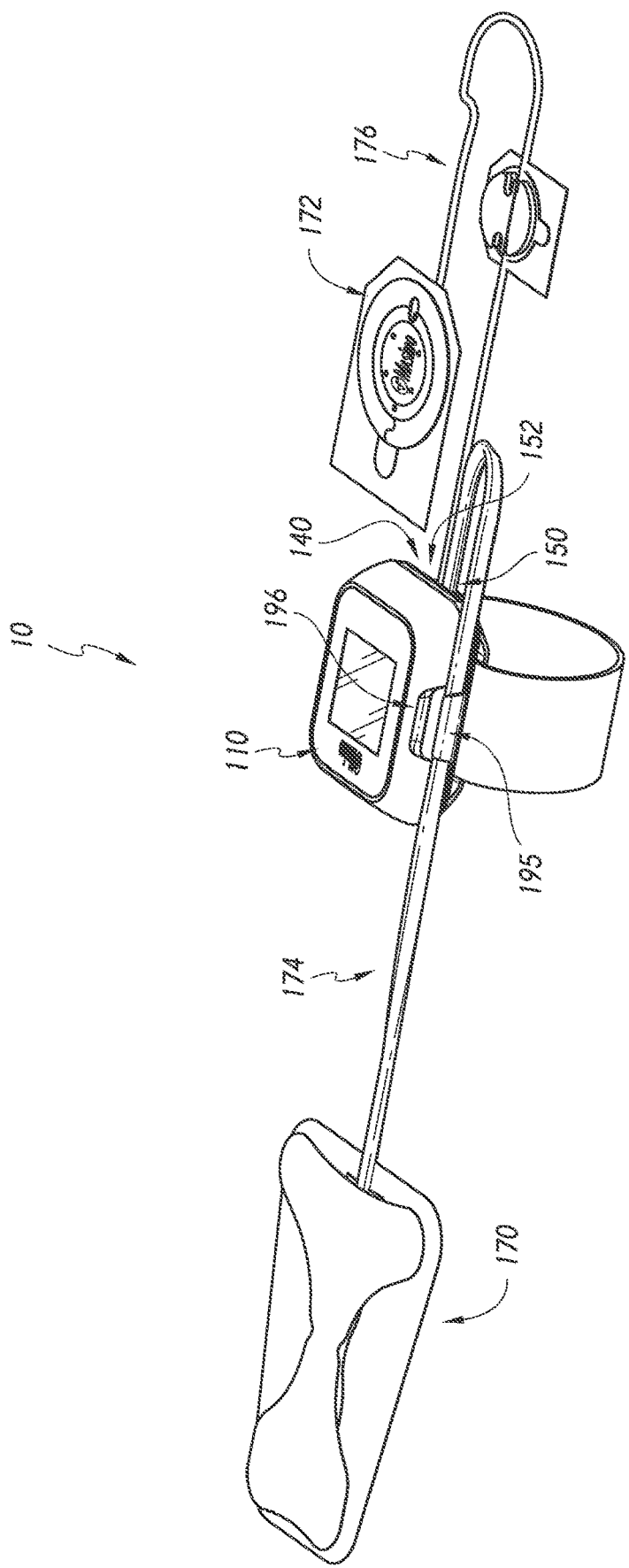
Figure 1F:
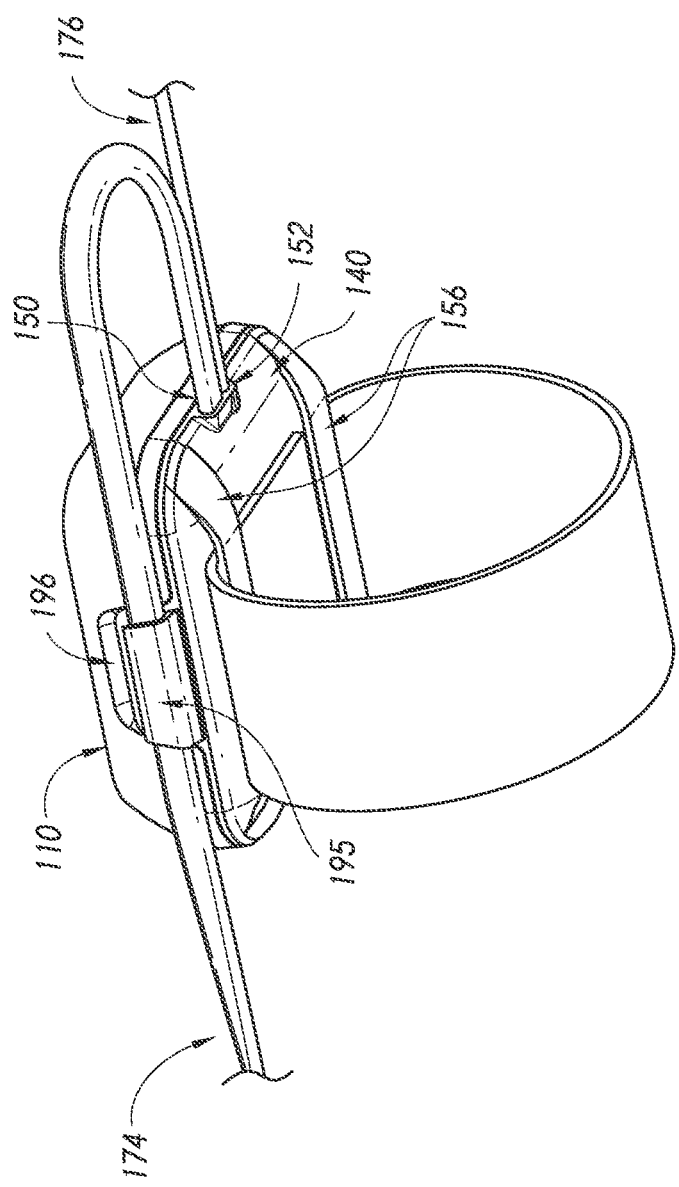
Figure 1G:
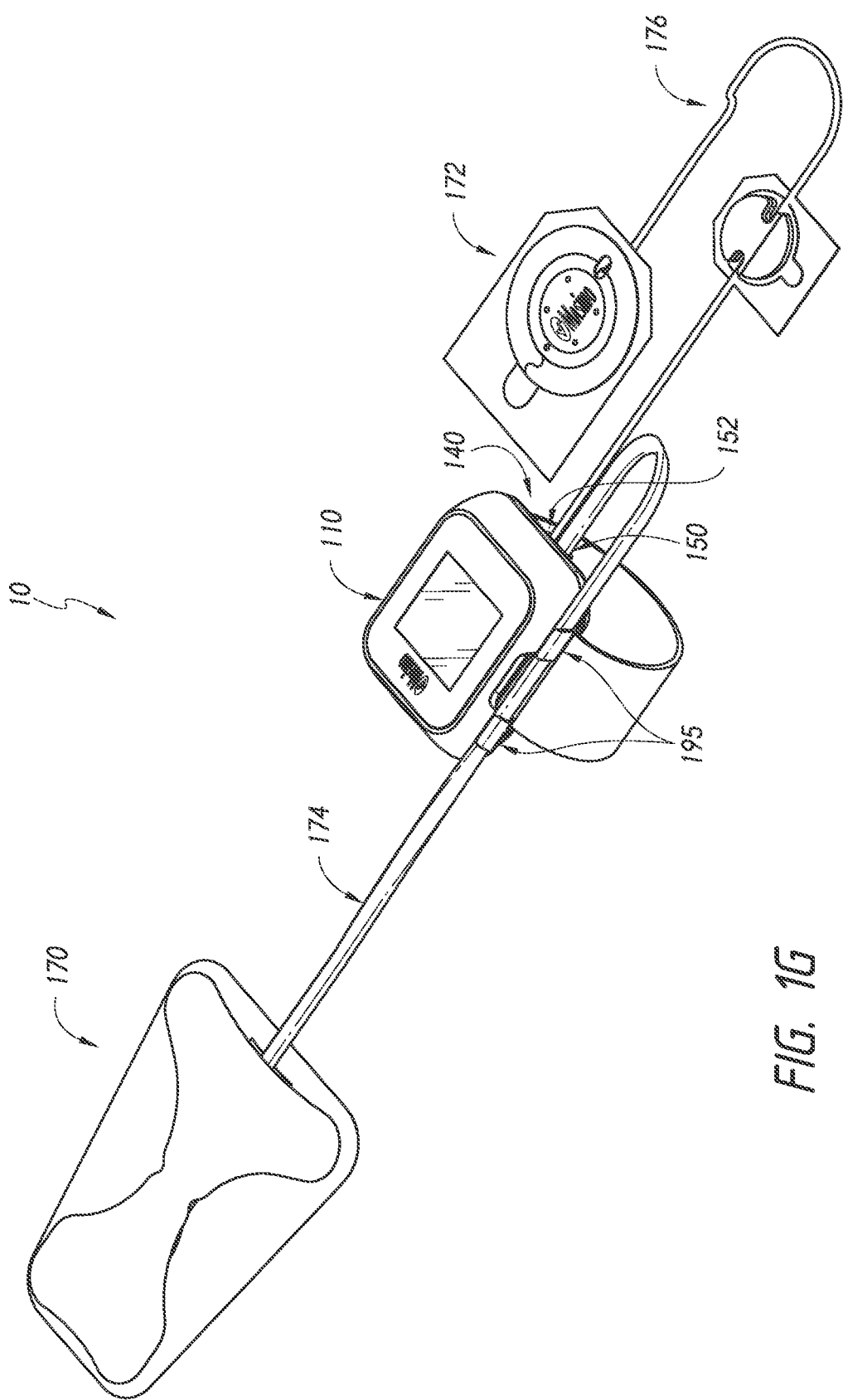
Figure 1H:
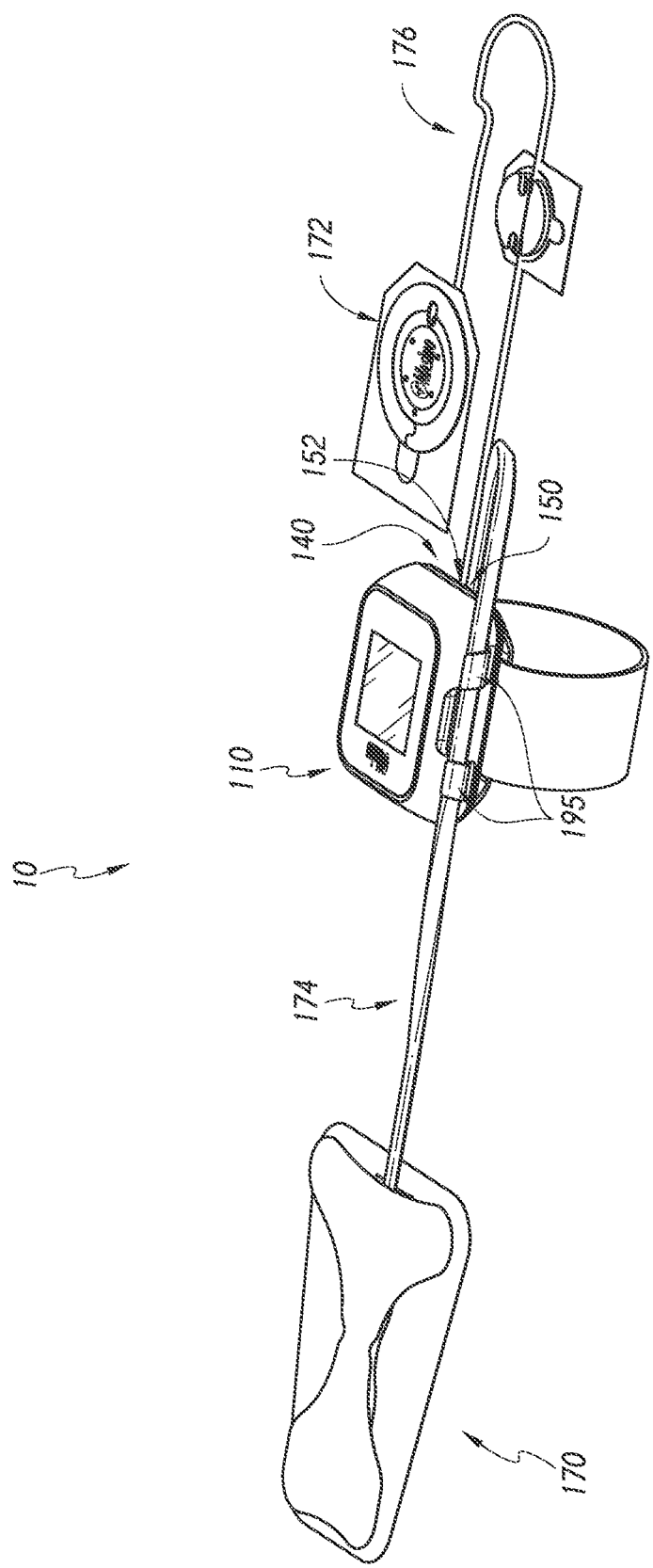
Figure 11:
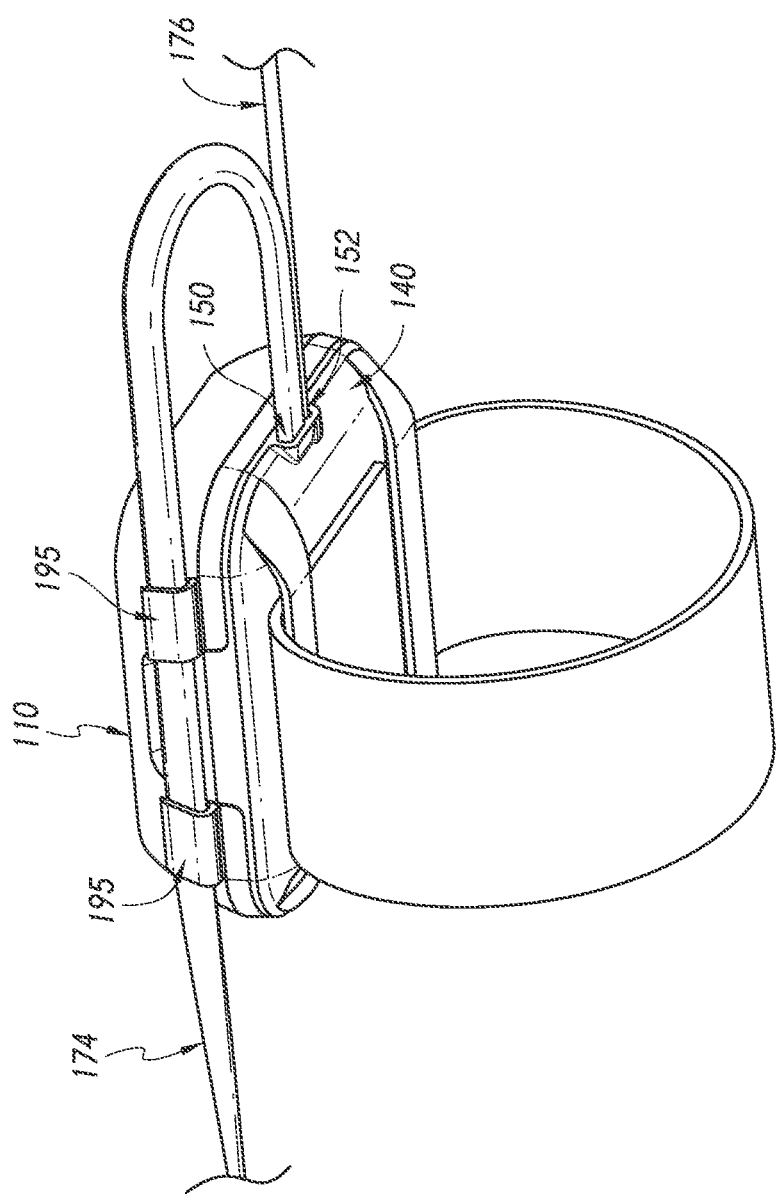
FIGS. 11A-D illustrate another embodiment of the wireless patient monitoring device.

As shown in FIGS. 1D-1F, the cable management system 195 can be a slidable cord-snap component configured to slide along the first cable 174 and be snapped onto a slot 196 on the monitor instrument 110 to retain the first cable 174 relative to the monitor instrument 110. As shown in FIGS. 1G-1H, the cable management system 195 can be one or more cord snap features attached to, or be an integral part of the monitor instrument 110 or the base 140. In some embodiments, two or more cable management systems 195 can be located on the monitor instrument 110 or the base 140 to retain the first cable 174. In some embodiments, additional cable management systems can be available to retain both of the first and second cables 174, 176 and make the cable lengths between the patient monitoring device 10 and both the first and second sensors 170, 172 adjustable. A skilled artisan will recognize that the cable management systems can be located on any suitable locations of the wireless patient monitoring device 10.

Electrical connections of the sensor(s) to the monitor instrument 110 will now be described. With continued reference to FIGS. 2A-2B, the anterior surface 142 of the base 140 can include a pad 146 having a plurality of electrical contacts 147 on one side of the pad 146. The pad 146 can be a PCB. In some embodiments, the pad 146 can have one or more EEPROMs or other electronic components. Each EEPROM can store identification information of a sensor, schemes for validating the authenticity of the sensor, and other information relating to the sensor. The one or more EEPROMs or other electronic components can be on the same side or reverse side of the pad 146 that has the plurality of electrical contacts 147. FIGS. 2D-E illustrate some non-limiting examples of the pads. The pad 146 can be molded onto the anterior surface 142 of the base 140. The pad 146 can be disposable with the rest of the base 140. The electrical contacts 147 can be electrically connected to at least one electrical connector. The electrical connector(s) can include electronics configured for connecting to one or more of the sensors 170, 172. Specifically, the electrical contacts 147 can be electrically connected to the cables 174, 176 by soldering one or more wires of each cable to a group of soldering points on the pad 146. The group of soldering points can be on the same side or reverse side of the pad 146 that has the plurality of electrical contacts 147. Thus, the PCB advantageously facilitates electrical communication between conductors of the cables 174, 174 and the processing device(s) of the instrument 110. Specifically, in an embodiment, the processor communicates with pogo style electrical pins housed in the instrument 110. When seated or otherwise fixed to the base 140, the pogo pins form an electrical connection with the electrical contacts 147. The electrical contacts 147 are in electrical communication with soldering points 254, 256 (shown in FIG. 2E), and in some embodiments, one or more information elements like an EEPROM, which are in turn in electrical communication with conductors of one or more of the cables 174, 176. In an embodiment, this electrical pathway electrically bridges the instrument 110 to one or more of the sensors through the base 140.

FIG. 2D shows a pad 200 having one group of soldering points 204 on a first side 208 of the pad 200. The pad 200 can have a second side 212 opposite the first side 208 The second side 212 can include a plurality of electrical contacts 216 configured to contact the pins 117, for example, as shown in FIG. 2A. The second side 212 can have one or more EEPROMs or other electronic components 220. The plurality of electrical contacts 216 can be on a recessed surface due to a thickness of the one or more EEPROMs or other electronic components 220. The pins 117 can be configured to have a length suitable for contacted the electrical contacts 216 on the recessed surface. The pins 117 and the electrical contacts 216 can be surrounded by common projections to establish electrical connection between the pins 117 and the electrical contacts 216. In some embodiments, the one or more EEPROMs or other electronic components 220 can be located on the first side 208 so that the electrical contacts 216 can be flush with a surface of the second side 212 of the pad 200. Having the electrical contacts 216 flush with the surface of the second side 212 of the pad 200 can ensure adequate contacts between the pins 117 and the electrical contacts 216. In addition, soldering of the one or more EEPROMs or other electronic components 220 and the cable wires to the pad 200 can be done on the same side of the pad 200

FIG. 2E shows another pad 250 having two groups of soldering points 254, 256 on a first side 258 of the pad 250. The two groups of soldering points 254, 256 can be configured to each accommodate wires from a sensor cable. The first side 258 can have at least two EEPROMs or other electronic components 270 located between the two groups of soldering points 254, 256. The pad 250 can have a second side 262 opposite the first side 258. The second side 262 can include a plurality of electrical contacts 266 configured to contact the pins 117, for example, as shown in FIG. 2A. The electrical contacts 266 are flush with a surface of the second side 262 of the pad. As described above, having the electrical contacts 266 flush with the surface of the second side 262 of the pad 250 can ensure adequate contacts between the pins 117 and the electrical contacts 266. One advantage of soldering two sensor cables to the pad 250 to establish electrical connection between the sensor(s) and the monitor instrument is that the cable wires can flex in all directions, making it easy to position the sensor(s) relative to the monitoring device.

In some embodiments, the electrical connection of the sensors and the monitor instrument can include a hybrid connector to accommodate one sensor cable and one flex-circuit. One of the sensors, such as the sensor 170, can include a flex-circuit instead of being connected to conducting wires of a sensor cable. The plurality of electrical contacts for contacting the pins can be located on or an integral part of the flex circuit, which incorporates, for example, conductive traces instead of conductive wires. The flex circuit can include a stiffening part, such as a flat board, behind the electrical contacts. Stiffening the electrical contacts portion of the flex circuit can increase the rigidity of the electrical contacts, thereby ensuring adequate contact between the pins and the electrical contacts. The flex-circuit can include an extension having a group of soldering points. Cable wires of the sensor cable for connecting to a second sensor, such as the sensor 172, can be soldered onto the group of soldering points. The extension can optionally be supported by a stiffening board. Because of the flexibility of the flex-circuit, the extension having the group of soldering points can be folded under the electrical contacts or at other locations to expose the electrical contacts for contacting the pins. Additional details of the flex-circuit are described in U.S. application Ser. No. 13/951,313, filed on Jul. 25, 2013 and entitled "AUTOMATED ASSEMBLY SENSOR CABLE," which is expressly bodily incorporated in its entirety and is part of this disclosure. An artisan will recognize from the disclosure herein that one or more cables, individual cables, or all cables could advantageously include one or more flex circuits.

In the illustrated embodiment, the plurality of electrical contacts 147 can be arranged in two rows and located in a center of the anterior surface 142 of the base 140 so as to be able to overlap with the pad 116 on the posterior surface 114 of the monitor instrument 110 as shown in FIG. 2A. One of ordinary skill in the art will appreciate from the disclosure herein that the number and arrangement of the pad 146 with the plurality of electrical contacts 147 are not limiting. For example and not by way of limiting, the anterior surface 142 of the base 140 can have four pads 146 with a plurality of electrical contacts 147, one on each corner of the substantially rectangular anterior surface 142 of the base 140, and the posterior surface 114 of the monitor instrument 110 can have four corresponding covers 116 with a plurality of pogo pins 117 on the four corners of the posterior surface 114 of the monitor instrument 110.

As described above, the cables 174, 176 can extend outside the base 140 at the outlets 150, 152, respectively. In some embodiments, the outlets 150, 152 can include the electrical connectors, such as mechanical plugs that are electrically connected to the electrical contacts 147. The first and second sensor cables 174, 176 can be plugged into the mechanical plugs. In some embodiments, the mechanical plug can include a phone plug or the like. Although two separate outlets are shown in the illustrative example, the wireless patient monitoring device 10 can include a single outlet with two plugs, or a multi-port connector configured for connecting to a plurality of sensors of different types and/or sizes.

When the monitor instrument 110 is removably engaged with the base 140, the posterior surface 114 of the monitor instrument 110 can overlap with the anterior surface 142 of the base 140. The pogo pins 117 on the monitor instrument 110 can come into contact with the electrical contacts 147 on the base 140, thereby establishing electrical connections between the printed circuit boards inside the monitor instrument 110 and the sensors 170, 172. In some embodiments, when the posterior surface 114 of the monitor instrument 110 comes into close proximity with the anterior surface 142 of the base 140, the pogo pins 117 can retract into the pogo pin holes while still maintaining electrical connection with the electrical contacts 147. The electrical connection between the monitor instrument 110 and the sensors 170, 172 can allow the sensors 170, 172 connected to the base 140 to communicate with and send sensor data to the monitor instrument 110. Having the electrical contacts for the pogo pins on the base can advantageously reduce a size of a connector between a sensor and a monitor, or between a sensor and a sensor cable, and make the connecting structures less bulky. The less bulky connecting structures can advantageously provide more comfort to the patient. One of ordinary skill in the art will also appreciate from the disclosure herein that types of electrical connectors other than pogo pin connectors can be used to electrically connect monitor instrument 110 and the base 140.

Figure 2F:
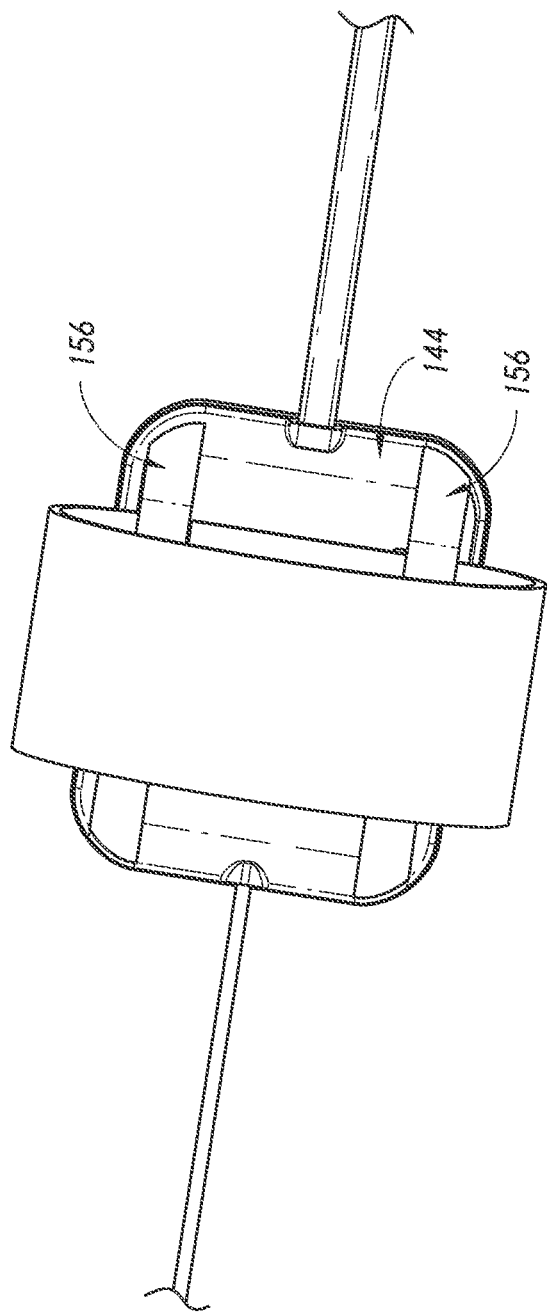
FIG. 2F illustrates back views of a base and a strap of an embodiment of the wireless patient monitoring device.

As shown in FIGS. 1F, 2F, and 3A, the base 140 can include one or more strap connectors 156 for engaging the strap 160. The strap connector 156 can be an integral portion of the base 140 or a separately formed component secured to the base 140 mechanically, or via adhesives or welding, or the like. The strap connector 156 can form an opening 157 with the posterior surface of the base 140. The strap 160 can pass through the opening 157 to be secured to the base 140. As shown in FIGS. 1F and 2F, the base 140 can have two strap connectors 156 on opposite ends across a width of the base 140.

The strap 160 can include any fabric, elastic, or otherwise flexible material. In certain embodiments, the strap 160 can be waterproof. One or both ends of the strap 160 can be tapered. One or both ends of the strap 160 can include a covering to protect the strap ends. The strap 160 can be secured to the patient's wrist as a wristband, or in any other configuration. A portion of the strap 160 can be secured to another portion of the strap 160 using Velcro, clasps, adhesive, snap-fits, or any other connector. The strap 160 can include any or all of the features of the strap described in U.S. application Ser. No. 13/762,270, filed Feb. 7, 2013, titled "Wireless Patient Monitoring Device," the disclosure of which is hereby incorporated by reference in its entirety. In an embodiment, the strap can include a foam or posy wrap type material common in securing mechanisms for patient sensor, such as neonate or infant sensors. Each physiological sensor, such as one of the sensors 170, 172, can include its own sensor attachment mechanism separate from the base 140 and the strap 160. The sensor attachment mechanism can be configured to removably secure the physiological sensor to a measurement site on the patient. Each sensor can include a sensor positioner configured to position the sensor with respect to the measurement site on the patient. In an embodiment, the sensor attaches using an adhesive layer.

Other embodiments will be known to an artisan from the disclosure herein, including, for example, a Posey wrap, Velcro, tape, mechanical couplings generally having a closed bias to grip or otherwise stick to a measurement site, or other commercially available attachments.

Providing the patient monitoring device 10 wearable on the wrist can advantageously allow the patient to easily check the patient's physiological state or parameters by looking at the display screen of the monitor. Other advantages of the wearable patient monitoring device 10 include reducing clutter of cables, improving patient mobility by eliminating some or all of the cables.

In some embodiments, the patient monitoring device can removably connect to a sensor via a sensor cable connector. Examples of such patient monitoring devices are shown in FIGS. 5A-11D. In these embodiments, the sensor cable connector can extend from the reusable monitor instrument and the disposable base can include no electrical components. As shown in FIGS. 5A-7E, the patient monitoring device 50 can have features of the patient monitoring device 10 of FIGS. 1A-2B except as described below. Accordingly, features of the patient monitoring device 50 can be incorporated into features of patient monitoring device 10 and features of the patient monitoring device 10 can be incorporated into features of patient monitoring device 50. The monitor instrument 510, the base 540, and the strap 560 can operate in the same or similar manner to the operation of the monitor instrument 110, the base 140, and the strap 160 described above.

Figure 5A:
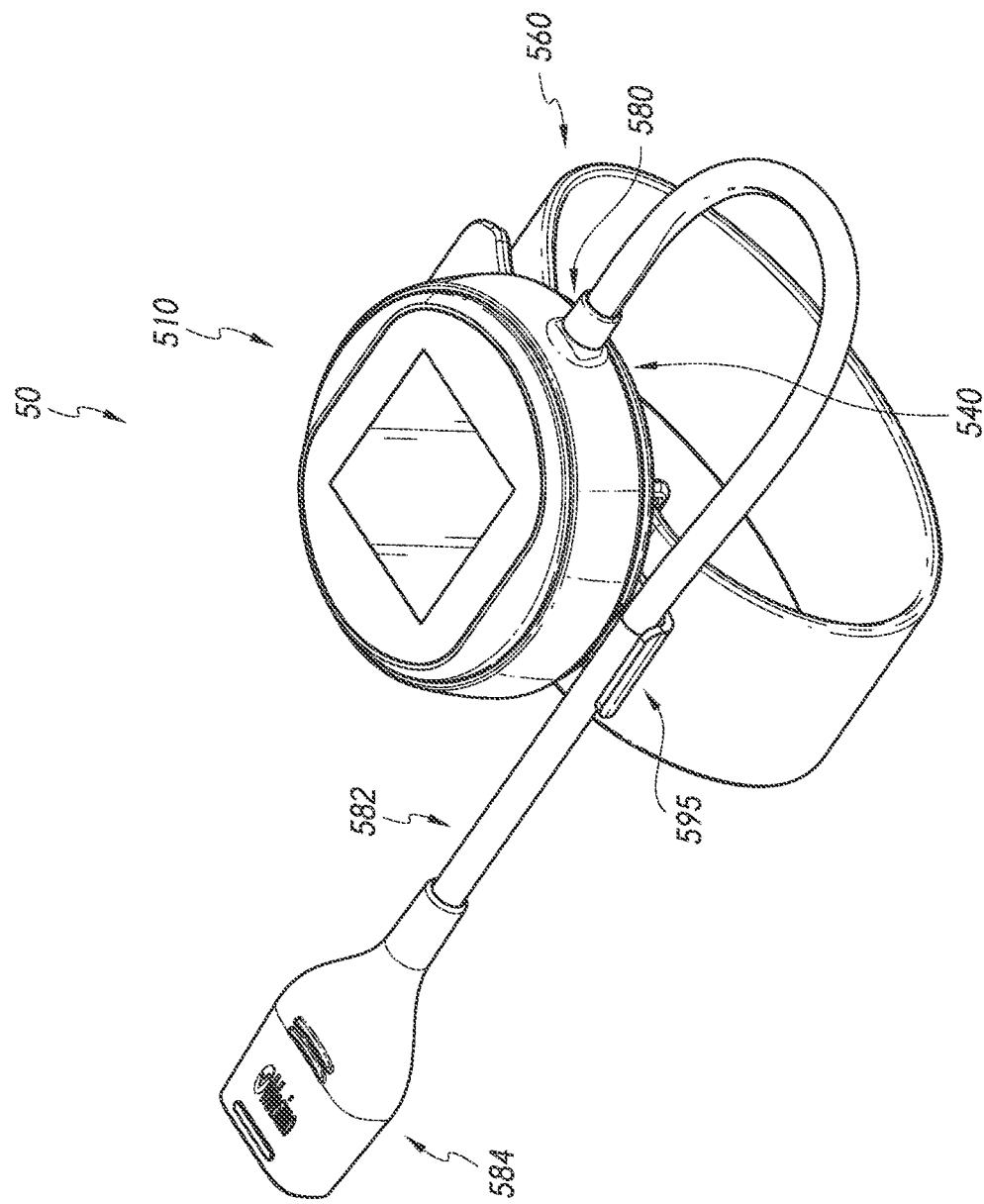
FIGS. 5A-D illustrate perspective, left, front, and bottom views of another embodiment of the wireless patient monitoring device.
Figure 5C:
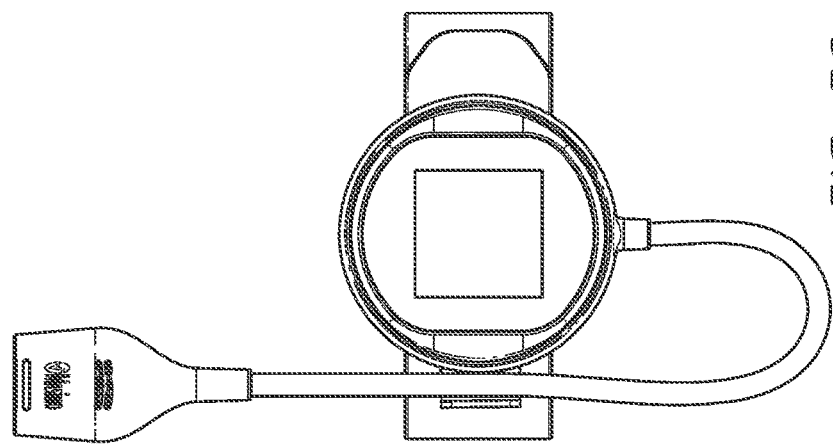
Figure 5D:
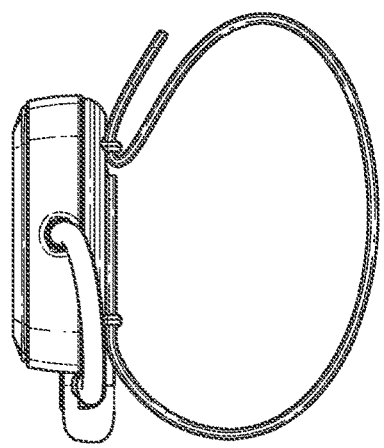
Figure 5B:
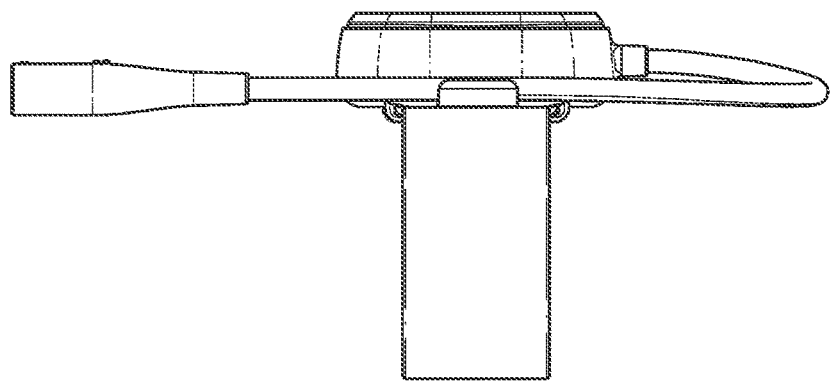
Figure 5E:
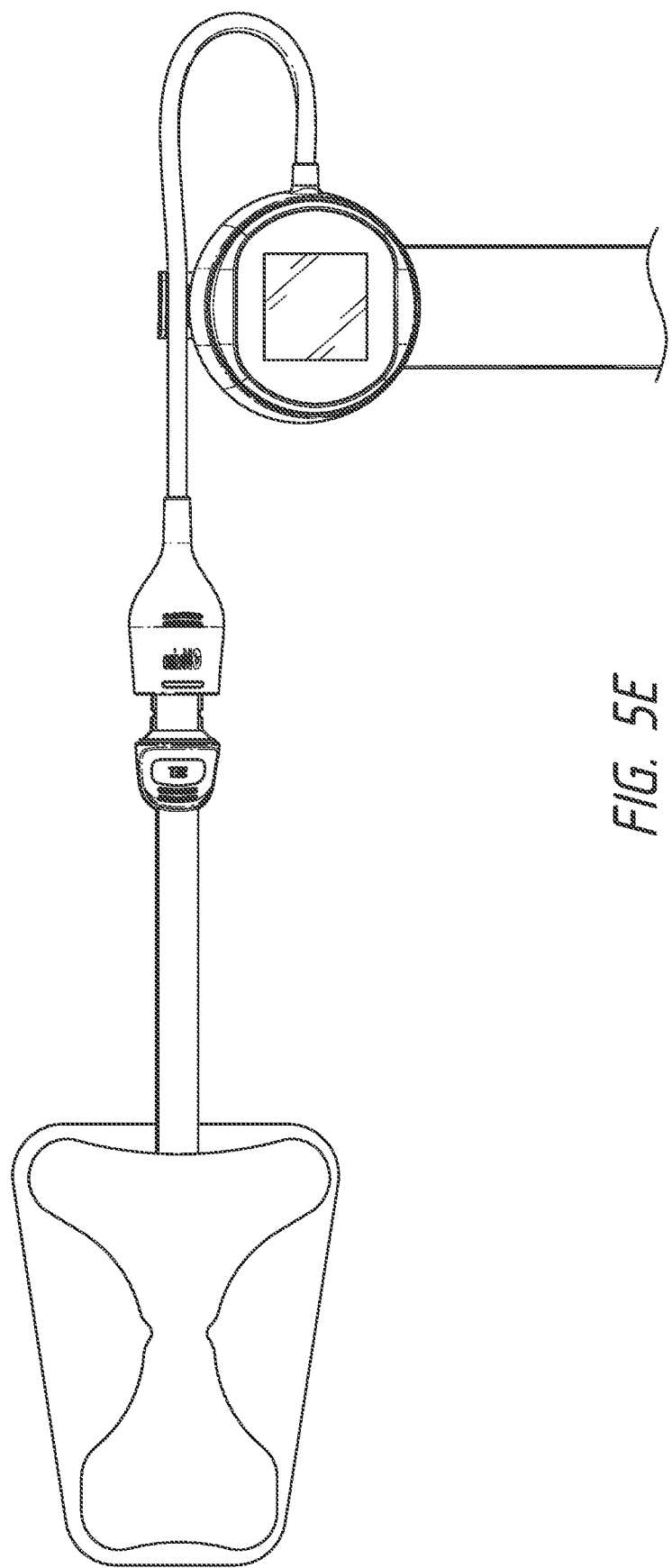
FIG. 5E illustrates the embodiment of the wireless patient monitoring device of FIGS. 5A-D connecting to a physiological sensor.
Figure 5F:
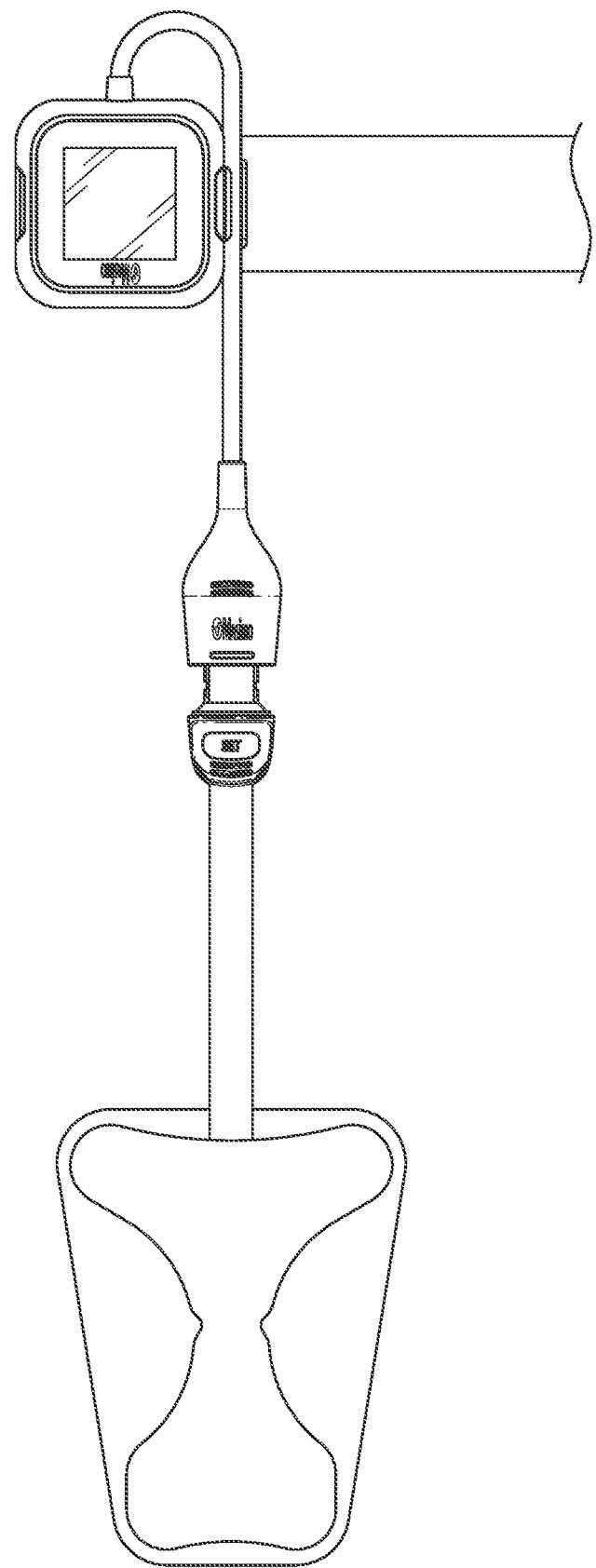
FIG. 5F illustrates another embodiment of the wireless patient monitoring device connecting to a physiological sensor.
Figure 6A:
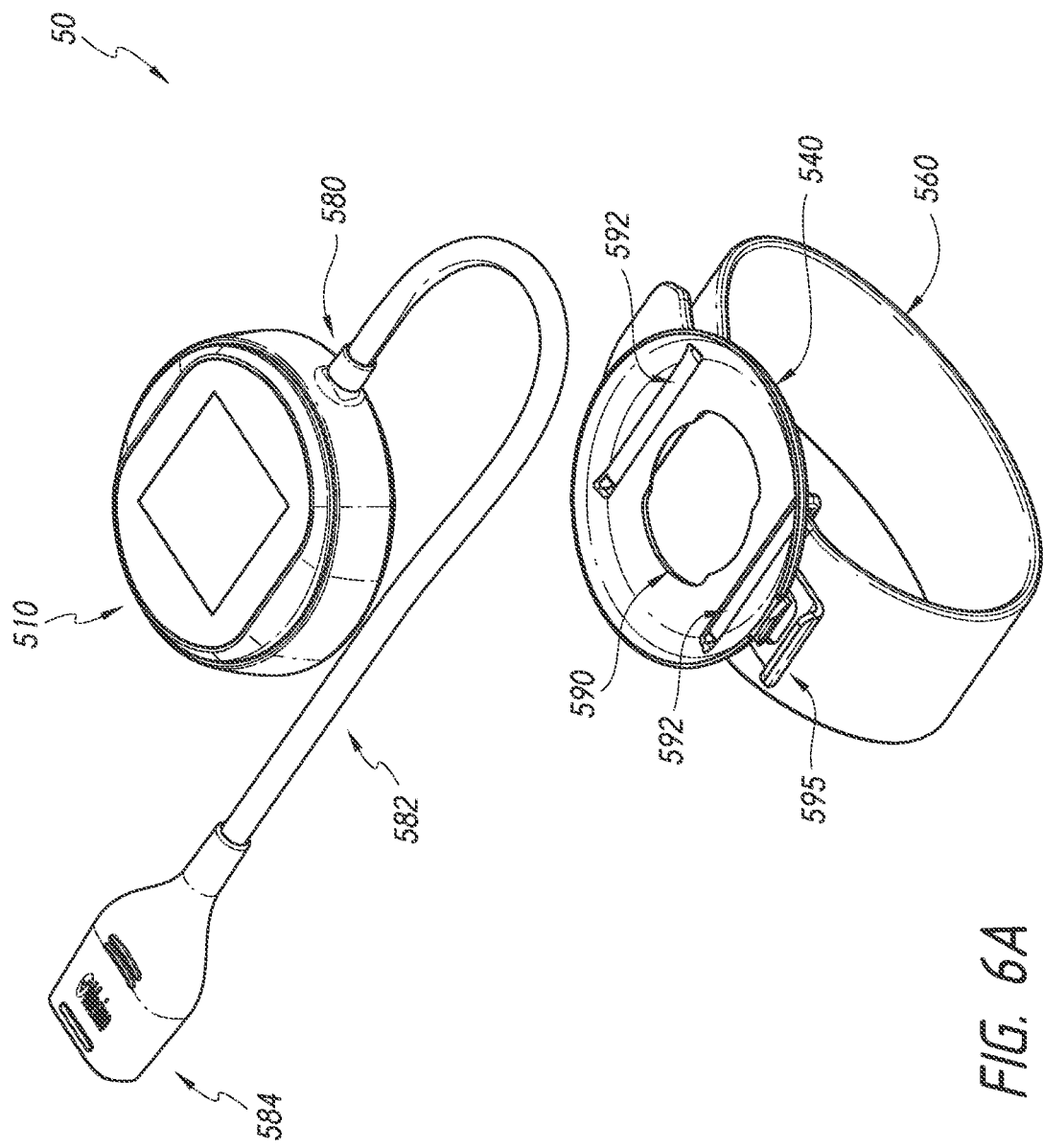
FIG. 6A illustrates a partial exploded view of the embodiment of the wireless patient monitoring device of FIGS. 5A-D.
Figure 6F:
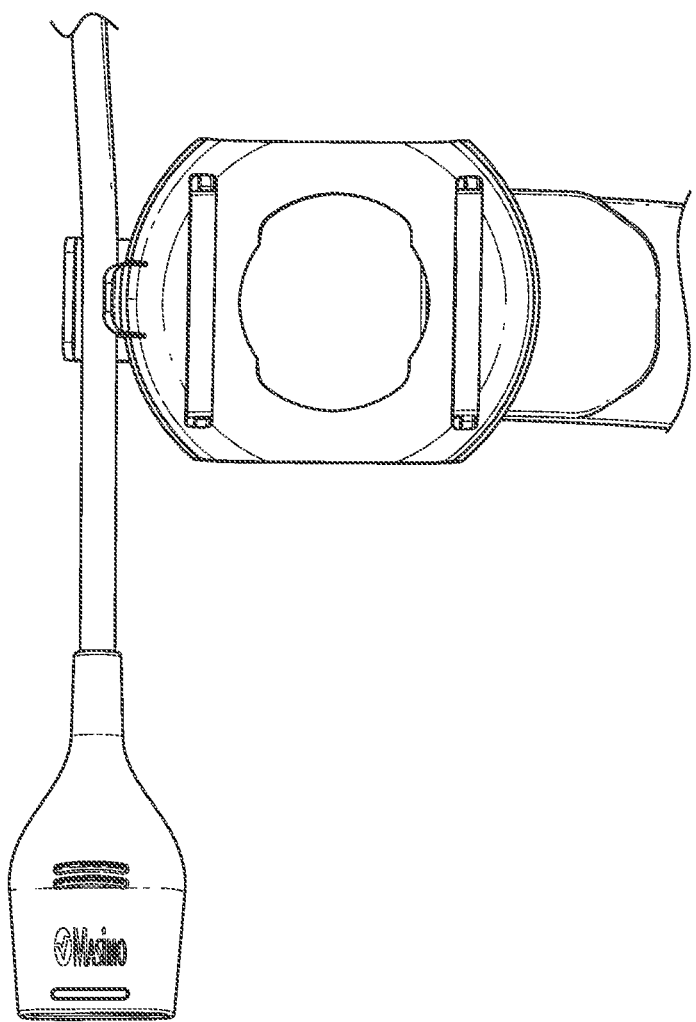
FIG. 6F illustrates front views of a base, a strap and a sensor cable of another embodiment of the wireless patient monitoring device.
Figure 7B:
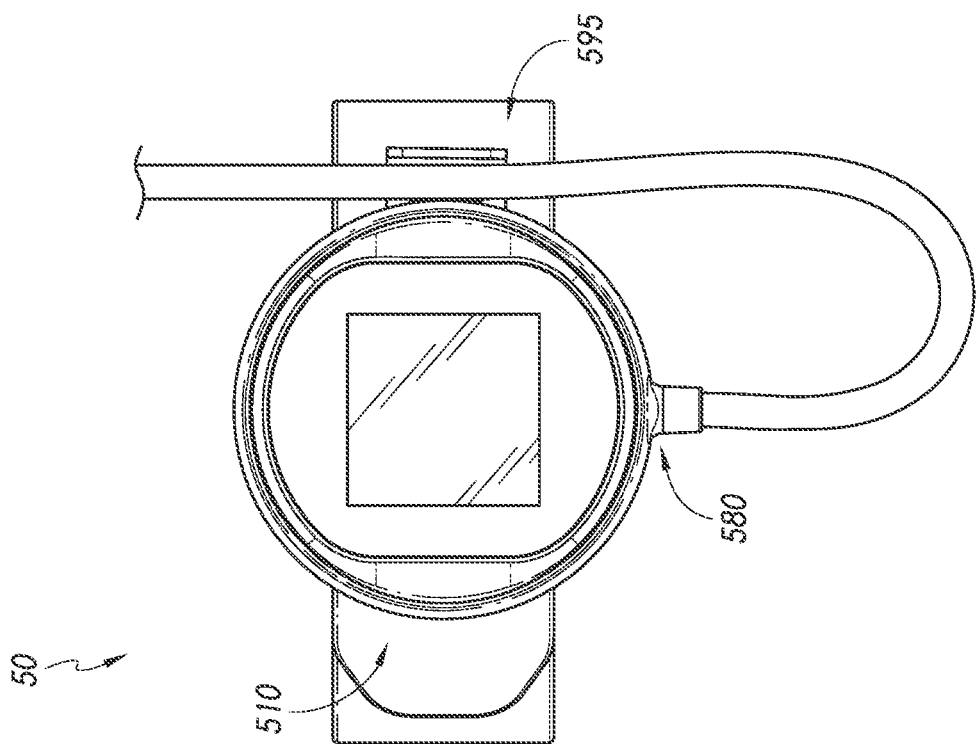
FIGS. 7A-E illustrate embodiments of the wireless patient monitoring device suitable for wearing on both the patient's left and right wrists.
Figure 7A:
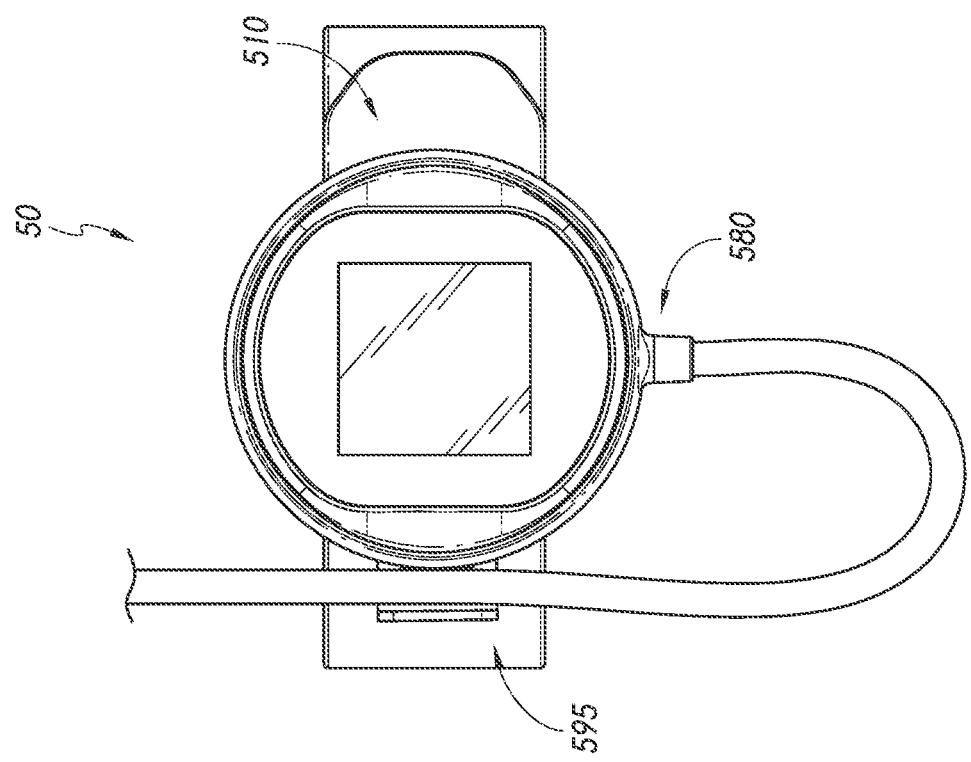
Figure 7D:
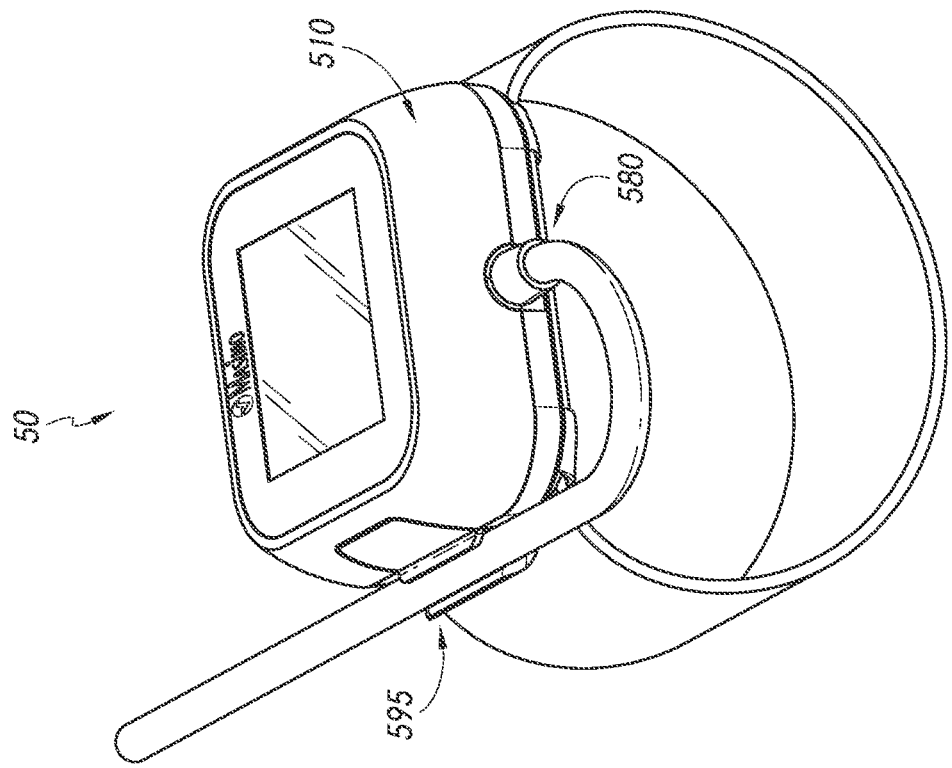
Figure 7C:
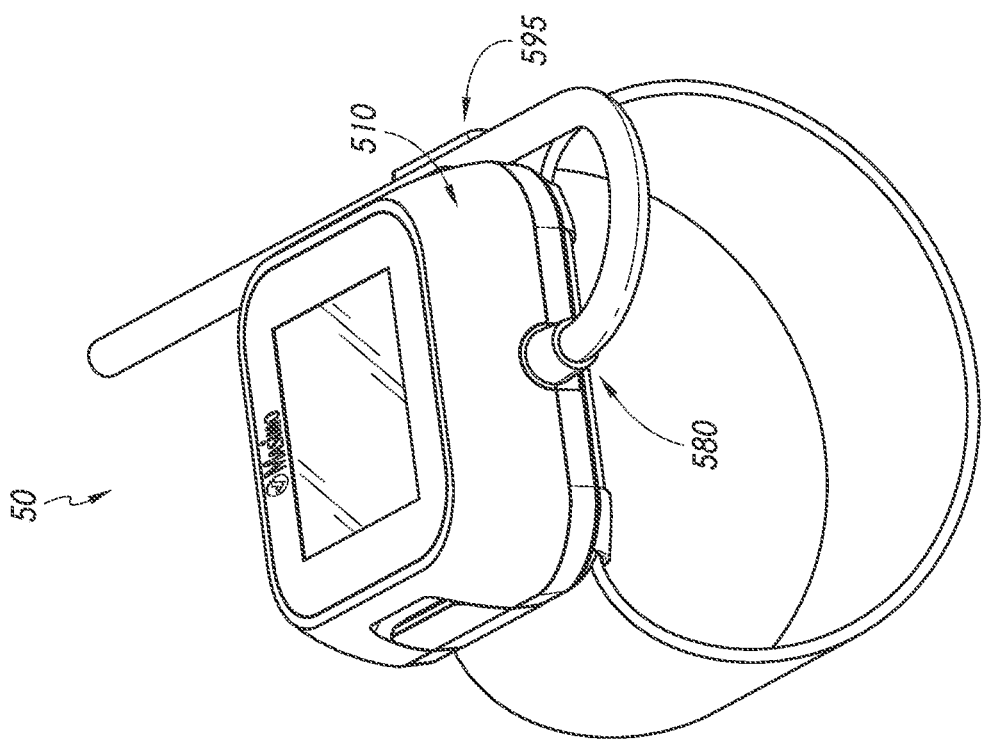
Figure 7E:
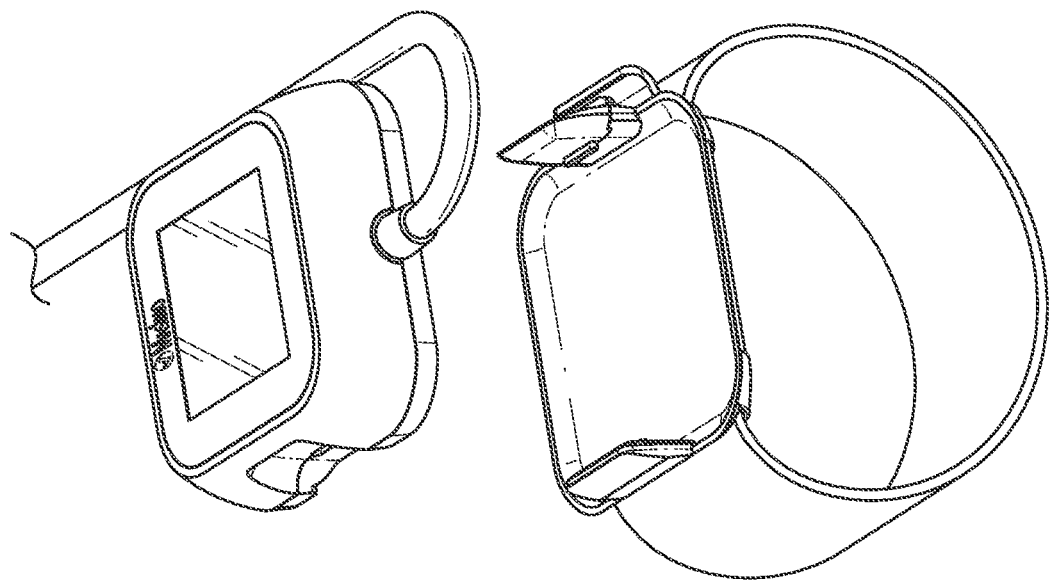

As shown in FIGS. 5A and 6A, the monitor instrument 510 and the base 540 can both have round outer shapes. The base can have a corresponding round outer shape. In some embodiments, such as shown in FIG. 6F, the base can have a corresponding round outer shape with two flat sides along a length of the strap. The two flat sides can reduce a foot print of the base when the device is worn by the patient, thereby making the device more comfortable to wear. In other embodiments, such as shown in FIGS. 5F and 7E, the monitor instrument 510 and the base 540 can have a square or rectangular outer shape. The monitor instrument 510 can have a cable outlet 580 on a side wall of the monitor instrument 510. A sensor connector cable 582 can extend from the cable outlet 580. In some embodiments, the sensor connector cable 582 can be permanently coupled to the cable outlet 580. The sensor connector cable 582 can be electrically connected to an electrical circuit in the monitor instrument 510. The sensor connector cable 582 can terminate on a free end at a sensor cable connector 584. In some embodiments, the sensor cable connector 584 can comprise pogo pin connectors. Types and methods of electrically connecting the sensor cable connector 584 and a sensor are not limiting. A sensor (shown in FIGS. 10A-B) removably connected to the sensor cable connector 584 can send sensor data to the monitor instrument 510.

Also as shown in FIGS. 5A and 6A, the base 540 can have an opening 590 for engaging, and mechanically and removably mating with a complementary protruding portion on the posterior surface of the monitor instrument 510. The opening 590 can have an irregular shape configured for rotationally retaining the monitor instrument 510. In the illustrated embodiment, the opening 590 can have an outer shape of two substantially rectangular shapes overlapping with each other, one of the substantially rectangular shapes being generally perpendicular with the other one of the substantially rectangular shapes. The base 540 can optionally have one or more open slots 592 to aid the positioning and engagement between the base 540 and the monitor instrument 510. The complementary protruding portion on the monitor instrument 510 can pass through the opening 590 when a length of the protruding portion aligns with the length of the open 590 and a width of the protruding portion aligns with the width of the opening 590. The monitor instrument 510 can then be turned clockwise or anticlockwise about a quarter of a turn to secure the monitor instrument 510 to the base 540. As shown in FIG. 5A, when the monitor instrument 510 is engaged with the base 540, the cable outlet 580 can be pointing away from the strap 560 and substantially parallel to a width of the strap 560. This configuration of the cable outlet 580 can advantageously prevent the sensor connector cable 582 from contacting the strap 560 near the cable outlet 580, which can cause stress to and early failure of the sensor connector cable 582. This configuration can also allow the patient's wrist to move freely without being hindered by the sensor connector cable 582 extending from the cable outlet 580. FIGS. 6B-E illustrate reverse steps for removing the monitor instrument 510 from the base 540, such as by rotating the monitor instrument 510 anticlockwise or clockwise about a quarter of a turn so that a length of the protruding portion can align with the length of the open 590 and a width of the protruding portion can align with the width of the opening 590.

With continued reference to FIGS. 5A-6E, the base 540 can have a cord snap feature 595 similar to the cord snap feature 195 described above. The cord snap feature can be on a circumference of the base 540. The cord snap feature 595 can retain a portion of the sensor connector cable 582 and prevent the sensor connector cable 582 from dangling about the patient's wrist or arm. In the illustrated embodiment, the cord snap feature 595 can retain a portion of the sensor connector cable 582 by a snap fit, although methods of retaining the sensor connector cable 582 are not limiting. As shown in FIGS. 5A-6E, the cord snap feature 595 can be located along the width of the strap 560. The cord snap feature 595 can also be located substantially 90° from the cable outlet 580 when the monitor instrument 510 engages the base 540. The configuration of the cord snap feature 595 can advantageously allow the sensor connector cable 582 to be snapped on the cord snap feature 595 without having to make sharp turns. The configuration of the cord snap feature 595 can also advantageously allow the sensor connector cable 582 to run substantially parallel to the patient's arm when the patient wears the patient monitoring device 50 on her wrist.

As shown in FIGS. 7A-E, the cord snap feature 595 can be about 90° clockwise from the cable outlet 580 or about 90° counterclockwise from the cable outlet 580 when the monitor instrument 510 engages the base 540. These alternative configurations of the cord snap feature 595 can advantageously aid in the ergonomics of the device and cable management, and can accommodate both patients who prefer to wear the monitoring device 50 on the left wrist and patients who prefer to wear the monitoring device 50 on the right wrist. However, an artisan will recognize from the disclosure herein that the snap feature 595 can be in virtually any position with respect to the outlet 580 that provides for reduced clutter, better positioning of the sensor, reduced mechanical stress on the cable or cable connectors, or reduces pinching of the cable, or any other advantageous.

Figure 8A:
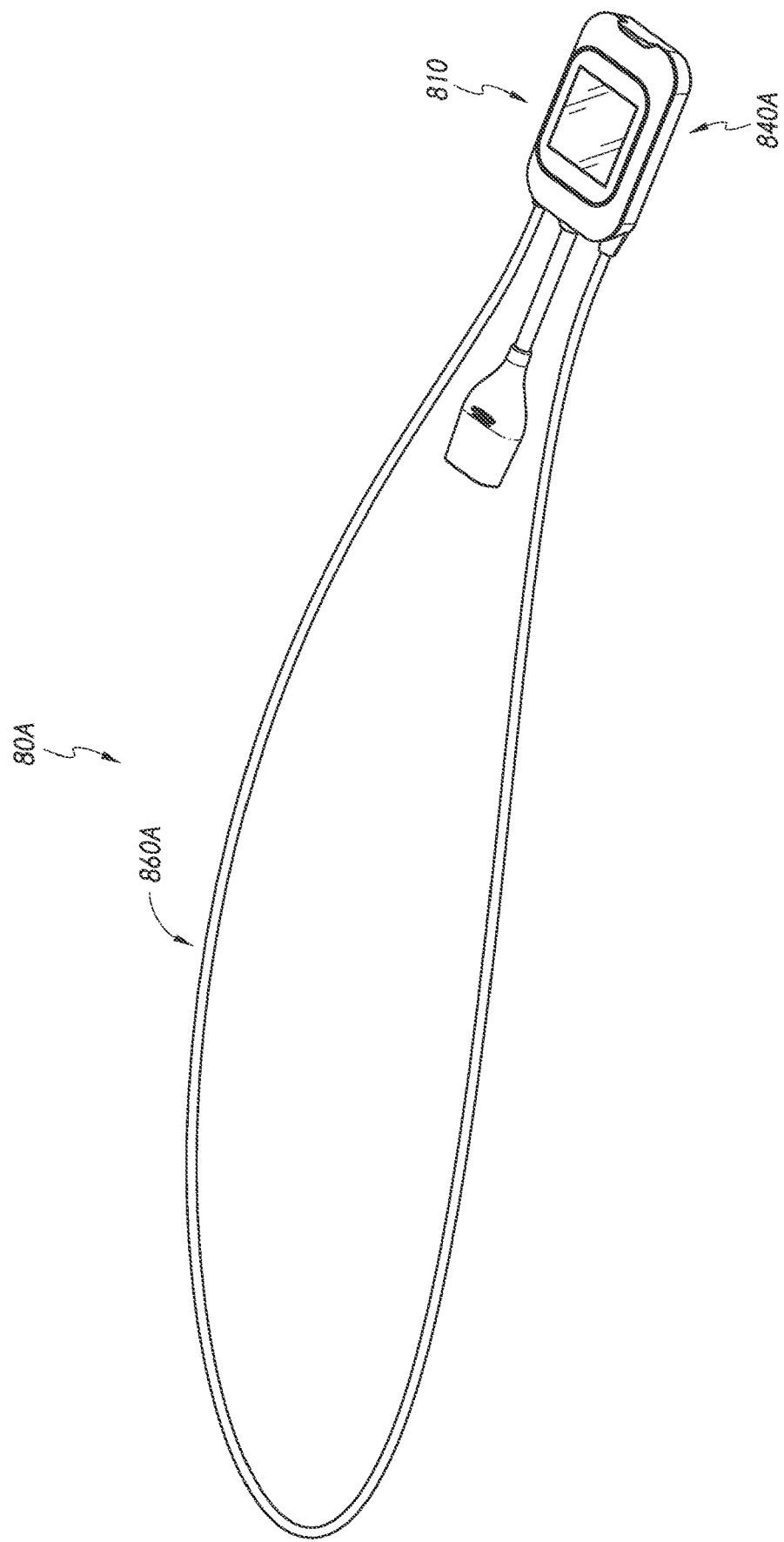
FIGS. 8A-B illustrate another embodiment of the wireless patient monitoring device that can be worn around a patient's neck.
Figure 8B:
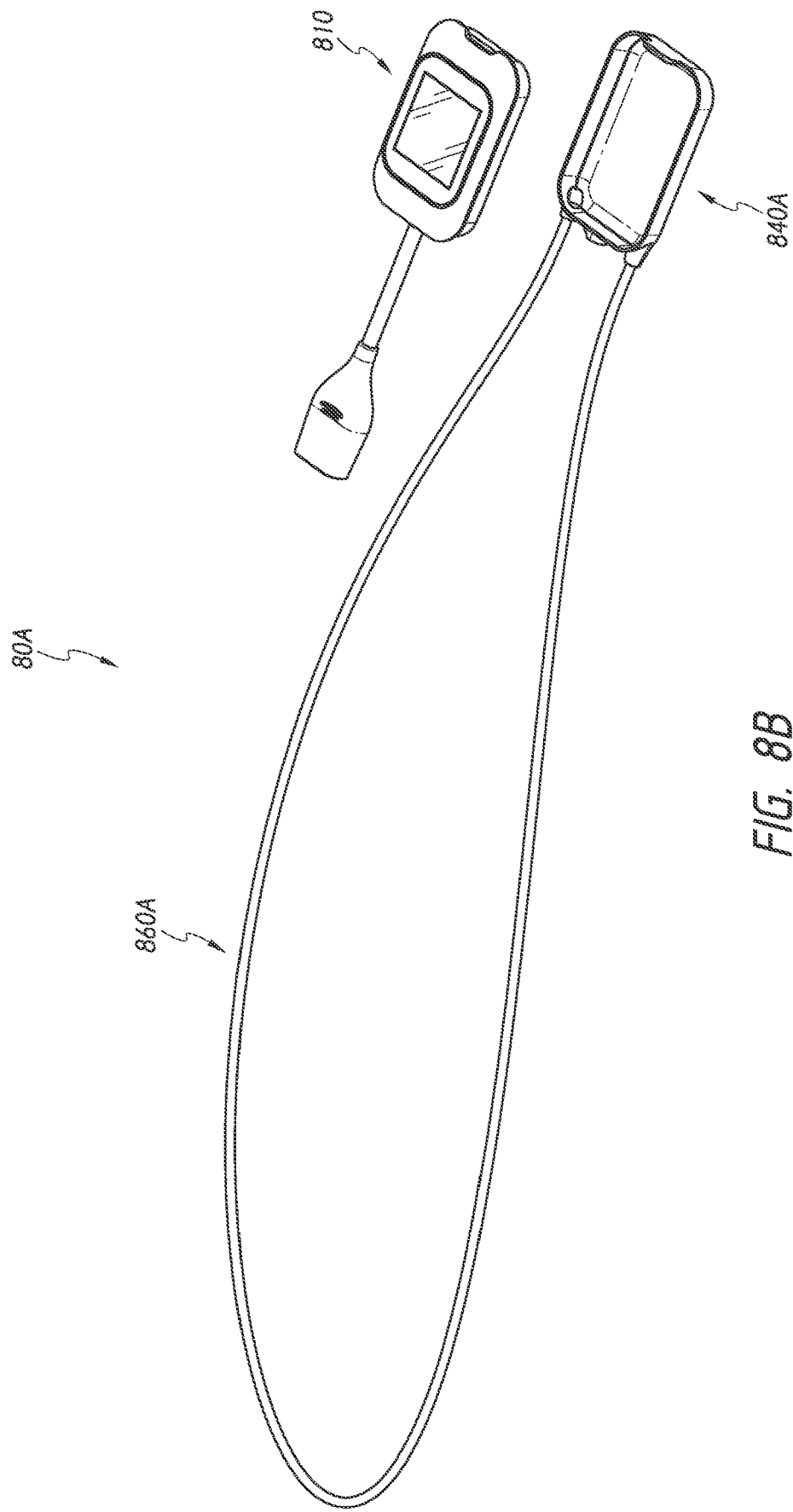
Figure 9A:
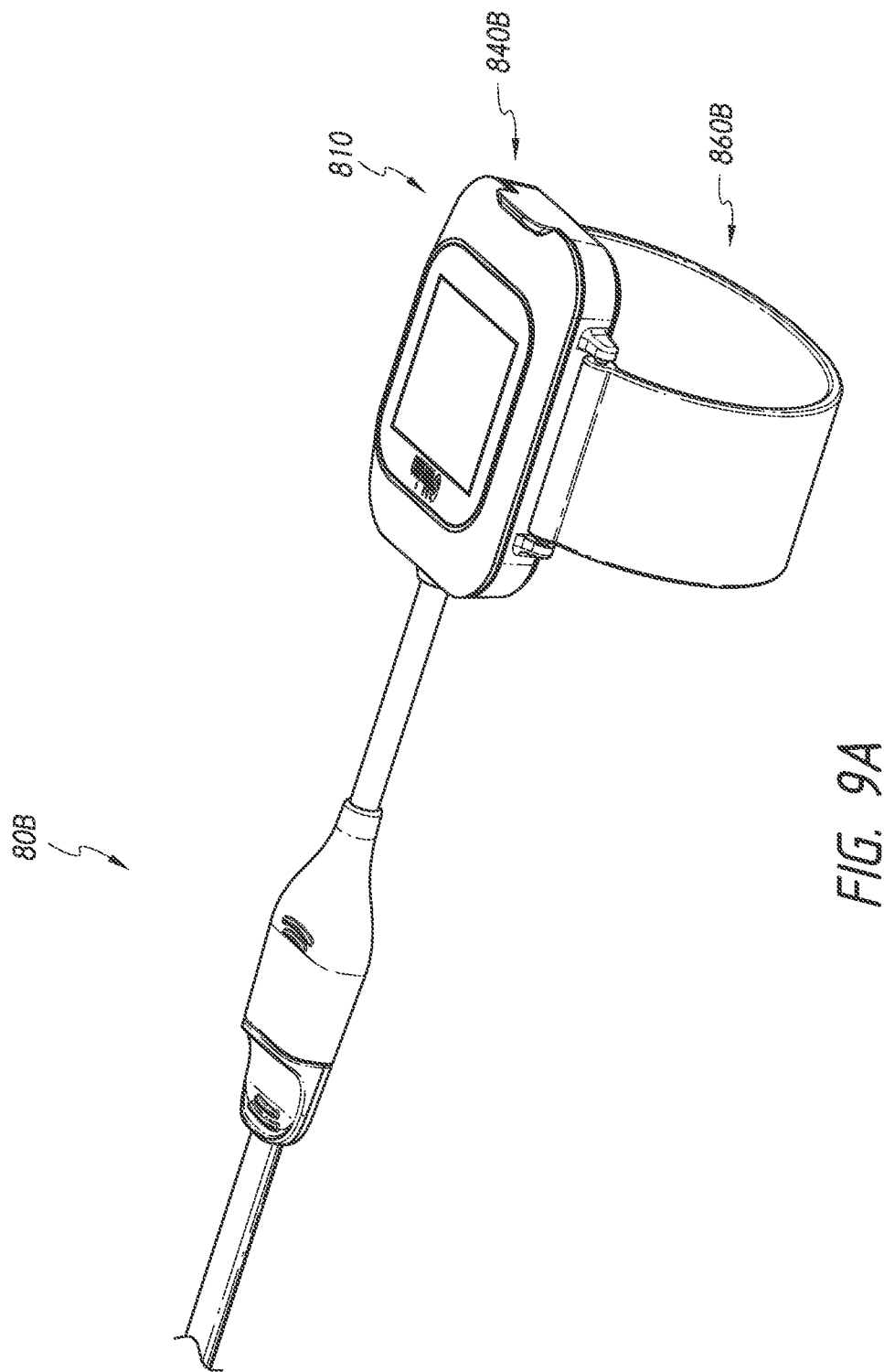
FIGS. 9A-B illustrate another embodiment of the wireless patient monitoring device that can be worn on the patient's wrist.
Figure 9B:
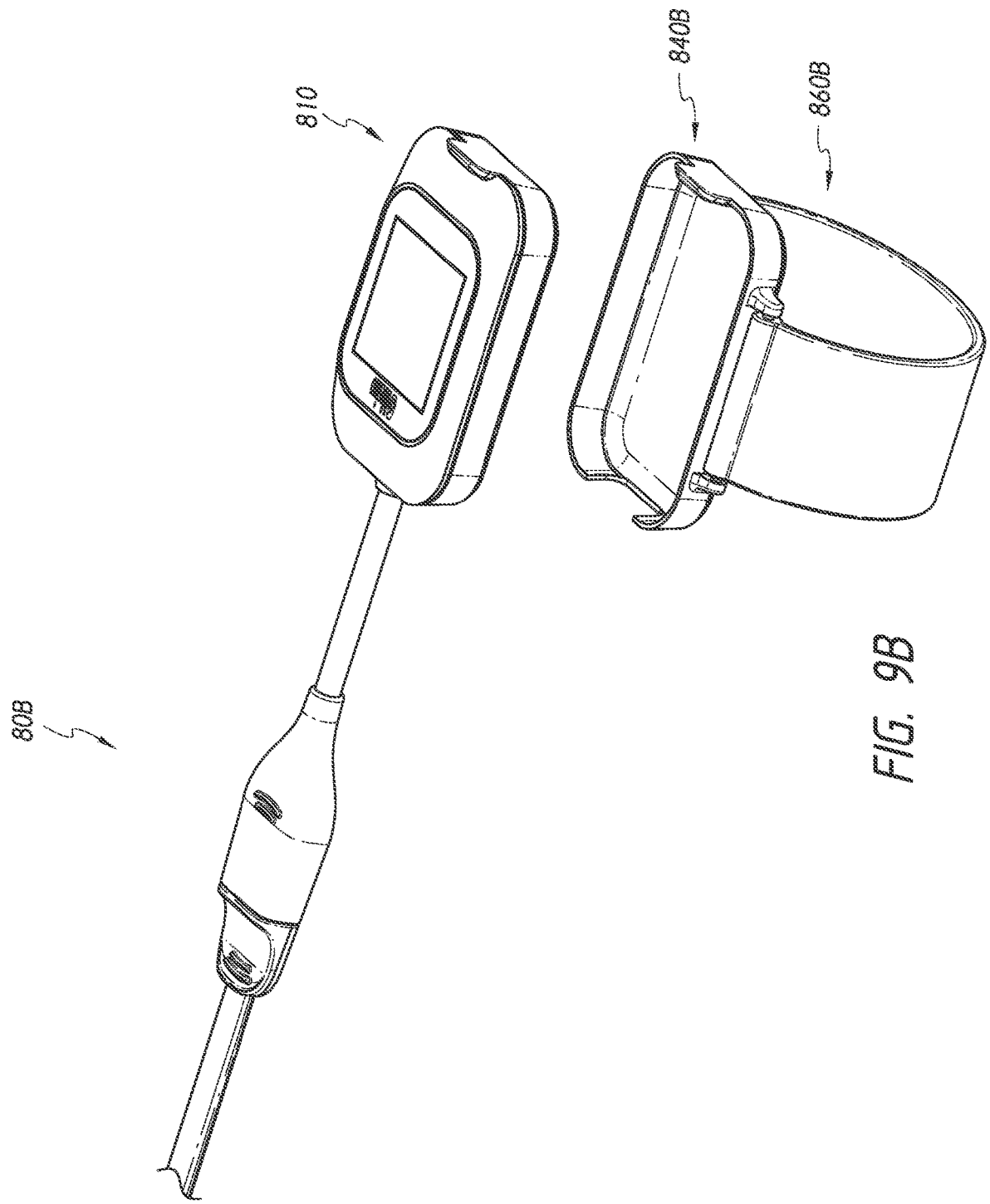

FIGS. 8A-9B illustrate embodiments of the patient monitoring device 80A, 80B. The patient monitoring devices 80A, 80B can have features of the patient monitoring device 50 except as described below. Accordingly, features of the patient monitoring devices 80A, 80B can be incorporated into features of patient monitoring device 50 and features of the patient monitoring device 50 can be incorporated into features of patient monitoring devices 80A, 80B. The monitor instrument 810, the bases 840B, and the strap 560B as shown in FIGS. 9A-B can operate in the same or similar manner to the operation of the monitor instrument 510, the base 540, and the strap 560 described above. The monitor instrument 810 can be configured to be compatible with both the bases 840A, 840B such that the patient can choose between wearing the device 80A around the neck, or wearing the device 80B on a wrist or arm.

As shown in FIGS. 8A-B, the base 840A of the patient monitoring device 80A can be connected to a cord 860A instead of the strap 860B. The cord 860A can be worn around the patient's neck. The cord 860A can advantageously allow the patient monitoring device 80A to be coupled with an in-ear and/or nose sensor (not shown) without requiring a long cable connecting the in-ear and/or nose sensor and the base 860A. Although the cord is described in connection with embodiments of the monitor instrument including a sensor cable connector, the cord can also be incorporated into embodiments of the patient monitoring device 10 described above such that the base 140 can be connected to a cord instead of being connected to the strap 160.

Figure 10A:
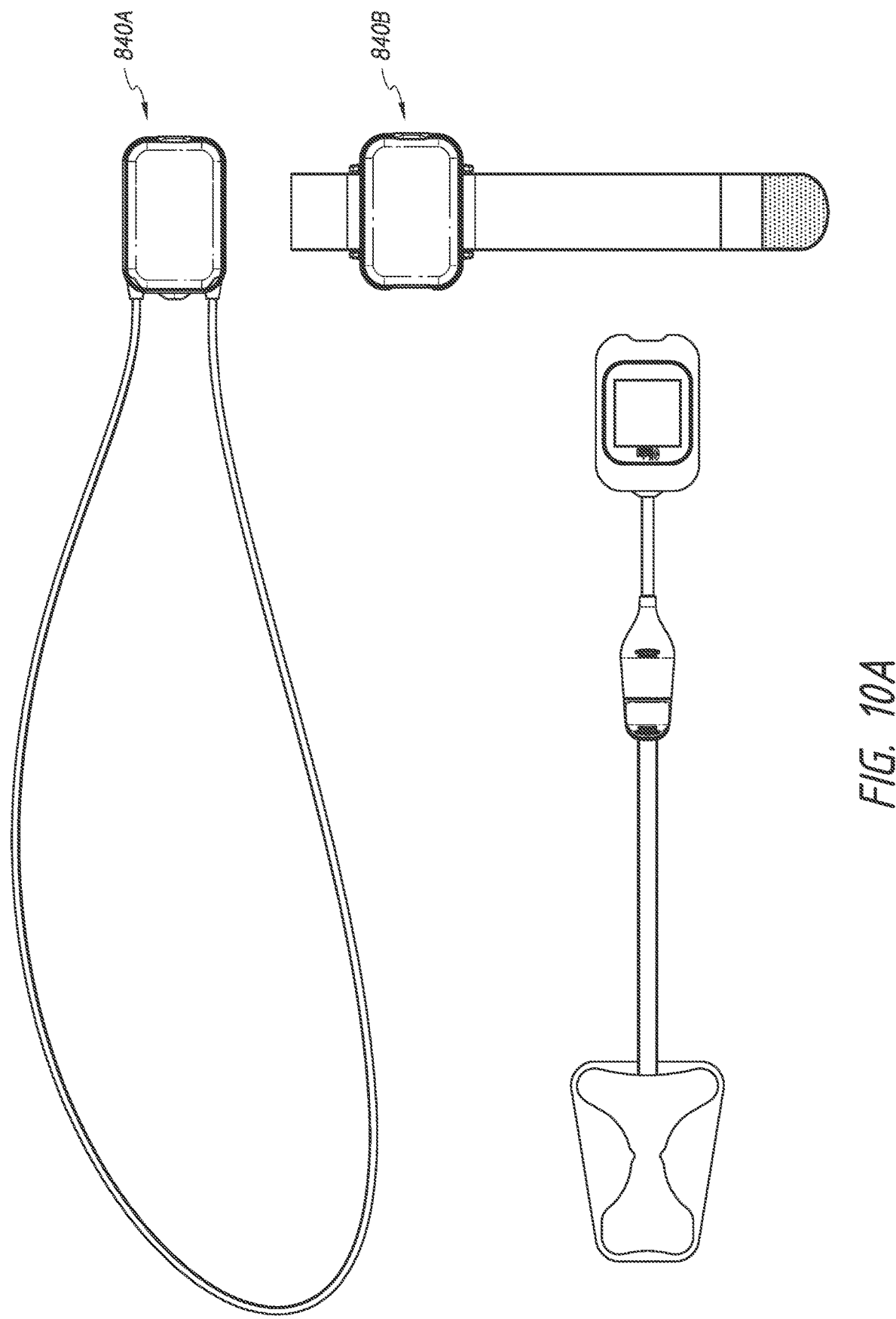
FIGS. 10A-B illustrate the embodiments of the wireless patient monitoring device of FIGS. 8A-B and 9A-B attached to a physiological sensor, with the monitor instrument detached from the bases.
Figure 10B:
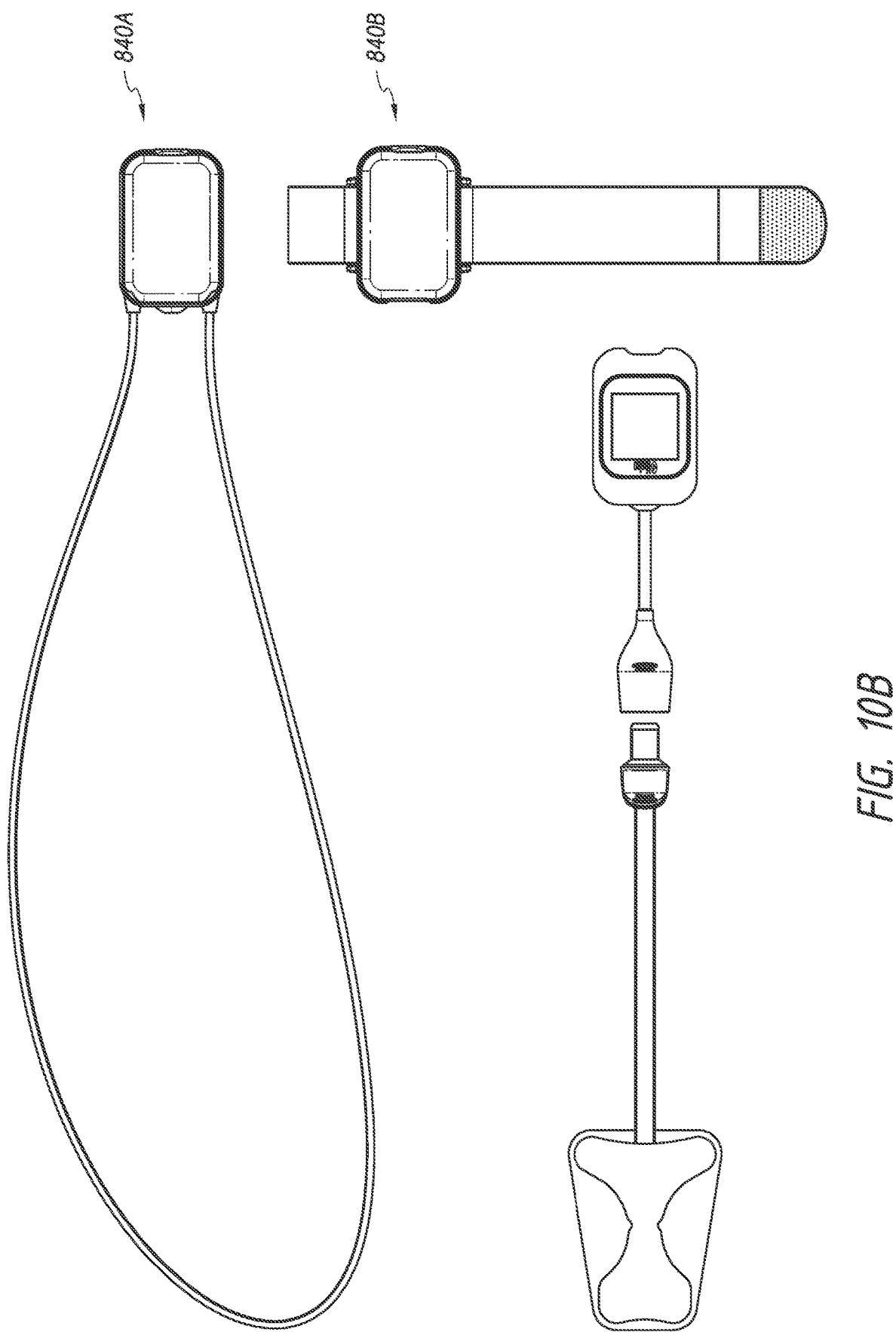

As shown in FIG. 10A-B, the bases 840A, 840B can both be compatible with the monitor instrument 810. For example, the bases 840A, 840B can have the same coupling features for engaging the monitor instrument 810 as described above. Accordingly, the same monitor instrument 810 can removably engage either the base 840B for wearing the patient monitoring device 80B on the wrist or the base 840A for wearing the patient monitoring device 80A around the neck. Interchangeability between the bases 840A, 840B can advantageously allow the monitor instrument 810 to be used with various types of the sensors depending on where the sensors need to be located on the patient's body.

Turning to FIGS. 11A-D, another embodiment of the patient monitoring device 100 is shown. The patient monitoring device 100 can have features of the patient monitoring device 50 except as described below. Accordingly, features of the patient monitoring device 100 can be incorporated into features of patient monitoring device 50 and features of the patient monitoring device 50 can be incorporated into features of patient monitoring device 100. The monitor instrument 1010, the bases 1040, and the strap 1060 as shown in FIGS. 11A-D can operate in the same or similar manner to the operation of the monitor instrument 510, the base 540, and the strap 560 described above.

As shown in FIG. 11A, the monitor instrument 1010 of the patient monitoring device 100 can have four sides. There can be two sliding channels 1090 on two opposing sides. In the illustrated embodiment, the sliding channels 1090 can be located on the sides that do not have a cable outlet or other types of connection features. The base 1040 can have corresponding protrusions (not shown) along two opposing sides of the base 1040. The sliding channels 1090 can accommodate the protrusions on the base 1040 so that the monitor instrument 1010 can slide onto the base 1040. FIGS. 11B-D show that the monitor instrument 1010 and the base 1040 can slide relative to each other in two directions as indicated by the arrows. In some embodiments, the sliding channels 1090 and the protrusions can have a friction fit or other types of tolerances so that the monitor instrument 1010 stays on the base 1040 without an external force along the directions of sliding shown in FIGS. 11B-D. This sliding configuration can advantageously prevent inadvertent rotation of the monitor instrument 1010 during use. In some embodiments, the protrusions on the base 1040 can be snap-fitted into the sliding channels and the sliding channels 1090 can have two closed ends to prevent the protrusions on the base 1040 from disengaging the sliding channels 1090. The protrusions can be configured to slide along the sliding channels 1090 during use such that when the patient rotates her wrist or arm, the monitor instrument 1010 can slide back and forth along the sliding channels. The slidable monitor instrument 1010 can increase the ergonomics of the device. A skilled artisan will recognize from the disclosure herein that other types of sliding mechanisms can be used, such as a sliding rail/channel on the monitor instrument 1010 or the base 1040 with two closed ends and one or more corresponding mushroom tabs on the base 1040 or the monitor instrument 1010.

Although this disclosure has been disclosed in the context of certain preferred embodiments and examples, it will be understood by those skilled in the art that the present disclosure extends beyond the specifically disclosed embodiments to other alternative embodiments and/or uses of the disclosure and obvious modifications and equivalents thereof. In addition, while a number of variations of the disclosure have been shown and described in detail, other modifications, which are within the scope of this disclosure, will be readily apparent to those of skill in the art based upon this disclosure. It is also contemplated that various combinations or sub-combinations of the specific features and aspects of the embodiments may be made and still fall within the scope of the disclosure. Accordingly, it should be understood that various features and aspects of the disclosed embodiments can be combined with or substituted for one another in order to form varying modes of the disclosed.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. Additionally, as used herein, "gradually" has its ordinary meaning (e.g., differs from a non-continuous, such as a step-like, change).

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive. For example, the scope of the present disclosure is not limited to parameters measurable by a pulse oximeter sensor and an acoustic sensor. The wireless patient monitoring system described herein can include sensor additions or substitutions to these sensors. The sensor additions or substitutions can be configured to monitor one or more of capnography, blood pressure, ECG, EEG, electrolytes, brain function/activity, patient turning, patient fall detection, patient location, and the like. The wireless patient monitoring system can also output to a multi-parameter monitor, or a regular patient monitor, or be configured to control signals for other devices, such as infusion pumps, oxygen supply, respiratory apparatuses, and the like. Connection between the wireless patient monitoring system and the multi-parameter monitor, regular patient monitor, or other devices can be via cable, via wireless technology, or both.

What is claimed is:

1. A patient monitoring device configured to be removably secured to a patient, the patient monitoring device comprising:
    a physiological sensor configured to be removably coupled to a finger of the patient;
    a cable comprising a first end coupled to the physiological sensor and a second end opposite the first end;
    a strap configured to secure to a wrist of the patient;
    a base coupled to the strap, the base comprising:
        a first side, a second side opposite the first side, a third side, a fourth side opposite the third side, a bottom surface positioned adjacent said strap and configured to face toward the patient's wrist, and a top surface configured to face away from the patient's wrist, wherein the first side is positioned closer to the patient's finger than the second side when the base and strap are secured to the patient's wrist, and wherein the second end of the cable is integrally formed with and extends outward from the second side of the base;
        one or more electrical contacts operably positioned by or near the top surface of the base; and
        a cable retainer arranged along the third side of the base and configured to at least partially surround and secure a portion of the cable; and
    a monitor instrument configured to removably couple to the base and receive one or more signals from the physiological sensor via the base;
    wherein, when the monitor instrument is coupled to the base, the strap and base are secured to the patient's wrist, the cable is secured within the cable retainer, and the physiological sensor is coupled to the patient's finger, the cable: extends away from the second side towards an elbow of the patient; loops 180 degrees towards the patient's finger; and extends to the physiological sensor coupled to the patient's finger.

2. The patient monitoring device of claim 1, wherein the physiological sensor is configured to measure a plurality of physiological parameters.

3. The patient monitoring device of claim 1, wherein the physiological sensor is configured to measure a blood oxygen saturation of the patient.

4. The patient monitoring device of claim 1, wherein the monitor instrument is configured to wirelessly communicate with a display device.

5. The patient monitoring device of claim 1, wherein the monitor instrument comprises a display screen.

6. The patient monitoring device of claim 1, wherein the monitor instrument is configured to process said one or more signals received from the physiological sensor to determine a blood oxygen saturation value of the patient.

7. The patient monitoring device of claim 1, wherein the physiological sensor includes an optical sensor comprising:
    one or more emitters configured to emit optical radiation into tissue of the patient's finger; and one or more detectors configured to detect at least a portion of the optical radiation emitted from the one or more emitters after passing through the tissue of the patient's finger and output at least one signal responsive to the detected optical radiation;

wherein said one or more signals received from the physiological sensor include said at least one signal responsive to the detected optical radiation outputted by said one or more detectors.

8. The patient monitoring device of claim 7, wherein the physiological sensor is configured to operably position said one or more emitters and said one or more detectors at opposite sides of the patient's finger.

9. The patient monitoring device of claim 1, wherein the monitor instrument is configured to wirelessly communicate with an external device.

10. The patient monitoring device of claim 1, wherein the physiological sensor comprises an adhesive layer configured to removably couple the physiological sensor to the finger of the patient.

11. The patient monitoring device of claim 1, wherein the base comprises one or more strap connectors configured to couple the base to the strap.

12. The patient monitoring device of claim 11, wherein each of said one or more strap connectors forms an opening with the bottom surface of the base, said opening configured to receive a portion of the strap therethrough.

13. The patient monitoring device of claim 1, wherein the monitor instrument comprises one or more recesses and the base comprises one or more tabs, said one or more recesses configured to removably engage said one or more tabs when the monitor instrument removably couples to the base.

14. The patient monitoring device of claim 13, wherein each of said one or more recesses comprises an indent and each of said one or more tabs comprises a protrusion, said indent configured to receive said protrusion when said one or more recesses removably engage said one or more tabs.

15. The patient monitoring device of claim 1, wherein the monitor instrument comprises one or more electrical contacts operably positioned by or near a bottom surface thereof, said bottom surface of the monitor instrument configured to face toward the top surface of the base.

16. The patient monitoring device of claim 15, wherein the one or more electrical contacts of the monitor instrument comprise a plurality of pogo pins configured to electrically couple with the one or more electrical contacts of the base when the monitor instrument is coupled to the base.

* * * * *